United States Patent
Lee et al.

(10) Patent No.: US 12,144,241 B2
(45) Date of Patent: Nov. 12, 2024

(54) ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

(71) Applicant: Samsung Electronics Co., Ltd., Suwon-si (KR)

(72) Inventors: Sunyoung Lee, Seoul (KR); Hyun Koo, Seongnam-si (KR); Soyeon Kim, Seoul (KR); Jungin Lee, Seoul (KR); Hyeonho Choi, Seoul (KR); Kyuyoung Hwang, Anyang-si (KR); Yoonhyun Kwak, Seoul (KR); Ohyun Kwon, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 991 days.

(21) Appl. No.: 16/120,961

(22) Filed: Sep. 4, 2018

(65) Prior Publication Data

US 2019/0074458 A1 Mar. 7, 2019

(30) Foreign Application Priority Data

Sep. 5, 2017 (KR) .................. 10-2017-0113559
Sep. 3, 2018 (KR) .................. 10-2018-0104723

(51) Int. Cl.
*H10K 85/30* (2023.01)
*A61K 33/24* (2019.01)
(Continued)

(52) U.S. Cl.
CPC .......... *H10K 85/346* (2023.02); *A61K 33/24* (2013.01); *A61K 33/242* (2019.01);
(Continued)

(58) Field of Classification Search
CPC ...... C07F 5/00; C07F 5/003; C07F 5/06–069; C07F 7/00; C07F 7/003; C07F 7/22–28;
(Continued)

(56) References Cited

U.S. PATENT DOCUMENTS

| 7,771,845 B2 | 8/2010 | Sano et al. |
| 8,153,278 B2 | 4/2012 | Kinoshita et al. |

(Continued)

FOREIGN PATENT DOCUMENTS

| EP | 2113548 A1 | 11/2009 |
| JP | 2007-099962 A | 4/2007 |

(Continued)

OTHER PUBLICATIONS

Blondel, B.; Delarue, F.; Lopes, M.; Ladeira-Mallet, S.; Alary, F.; Renaud, C.; Sasaki, I., 2017, Investigation of a sterically hindered Pt(II) complex to avoid aggregation-induced quenching: Applications in deep red electroluminescent and electrical switching devices, Synthetic Metals, 227, 106-116 (Year: 2017).*

(Continued)

*Primary Examiner* — Marla D McConnell
*Assistant Examiner* — Rachel Simbana
(74) *Attorney, Agent, or Firm* — CANTOR COLBURN LLP

(57) ABSTRACT

An organometallic compound represented by Formula 1,

Formula 1

(Continued)

wherein in Formula 1, groups and variables are the same as described in the specification.

20 Claims, 1 Drawing Sheet

(51) Int. Cl.

| | |
|---|---|
| *A61K 33/242* | (2019.01) |
| *A61K 33/243* | (2019.01) |
| *C07F 15/00* | (2006.01) |
| *C09K 11/06* | (2006.01) |
| *H10K 50/00* | (2023.01) |
| *H10K 50/11* | (2023.01) |
| *H10K 50/15* | (2023.01) |
| *H10K 50/16* | (2023.01) |
| *H10K 50/17* | (2023.01) |
| *H10K 50/18* | (2023.01) |
| *H10K 101/10* | (2023.01) |

(52) U.S. Cl.
CPC ........ *A61K 33/243* (2019.01); *C07F 15/0086* (2013.01); *C09K 11/06* (2013.01); *H10K 50/00* (2023.02); *C09K 2211/1044* (2013.01); *C09K 2211/185* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02)

(58) Field of Classification Search
CPC ........ C07F 9/00; C07F 9/005; C07F 15/0086; C07D 231/54; C07D 231/56; H01L 51/0087; H01L 51/0077–0089; H01L 51/0091–0092; H10K 85/346; H10K 85/341; C09K 2211/185; C09K 11/06; C09K 2211/182–188

See application file for complete search history.

(56) References Cited

U.S. PATENT DOCUMENTS

| | | | |
|---|---|---|---|
| 9,614,165 B2 | 4/2017 | Watanabe et al. | |
| 2005/0123792 A1* | 6/2005 | Deaton | H01L 51/0085 |
| | | | 313/506 |
| 2006/0060842 A1 | 3/2006 | Sano et al. | |
| 2006/0204787 A1* | 9/2006 | Sano | H01L 51/5012 |
| | | | 428/917 |
| 2007/0072003 A1 | 3/2007 | Ise et al. | |
| 2008/0036373 A1* | 2/2008 | Itoh | H10K 85/346 |
| | | | 546/88 |
| 2008/0145526 A1* | 6/2008 | Mao | G01N 33/6839 |
| | | | 546/10 |
| 2010/0140605 A1* | 6/2010 | Shibata | H01L 51/0087 |
| | | | 257/40 |
| 2015/0194615 A1* | 7/2015 | Lin | C07D 209/82 |
| | | | 546/4 |
| 2016/0240800 A1 | 8/2016 | Ma et al. | |
| 2018/0013078 A1 | 1/2018 | Lee et al. | |
| 2018/0254418 A1* | 9/2018 | Yoon | C09K 11/06 |

FOREIGN PATENT DOCUMENTS

| | | |
|---|---|---|
| JP | 2007096255 A | 4/2007 |
| JP | 2009283913 A | 12/2009 |
| KR | 20080014608 A | 2/2008 |
| WO | 2014-098045 A1 | 6/2014 |

OTHER PUBLICATIONS

Extended European Search Report issued by the European Patent Office on Jan. 31, 2019, in the examination of the European Patent Application No. 18192399.6-1109.

Office Action issued Oct. 16, 2023 of KR Patent Application No. 10-2018-0104723.

* cited by examiner

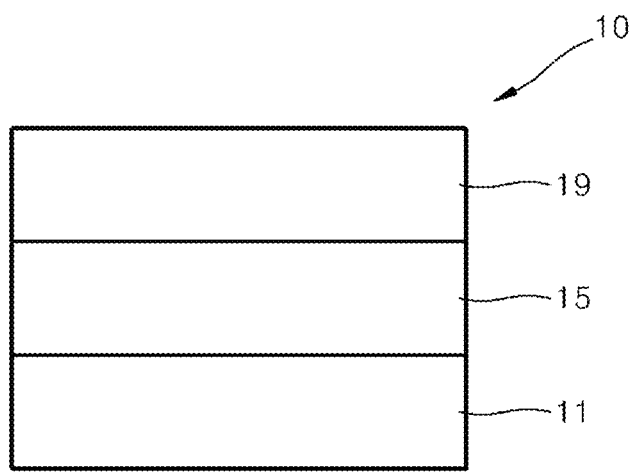

ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

CROSS-REFERENCE TO RELATED APPLICATION

This application claims priority to Korean Patent Applications Nos. 10-2017-0113559, filed on Sep. 5, 2017, and 10-2018-0104723, filed on Sep. 3, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to an organometallic compound, an organic light-emitting device including the organometallic compound, and a diagnostic composition including the organometallic compound.

2. Description of the Related Art

Organic light-emitting devices (OLEDs) are self-emission devices, which have superior characteristics in terms of a viewing angle, a response time, a brightness, a driving voltage, and a response speed, and which produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Meanwhile, luminescent compounds may be used to monitor, sense, or detect a variety of biological materials including cells and proteins. An example of the luminescent compounds includes a phosphorescent luminescent compound.

Various types of organic light emitting devices are known. However, there still remains a need in OLEDs having low driving voltage, high efficiency, high brightness, and long lifespan.

SUMMARY

Aspects of the present disclosure provide an organometallic compound, an organic light-emitting device including the organometallic compound, and a diagnostic composition including the organometallic compound.

Additional aspects will be set forth in part in the description which follows and, in part, will be apparent from the description, or may be learned by practice of the presented embodiments.

An aspect of the present disclosure provides an organometallic compound represented by Formula 1 below:

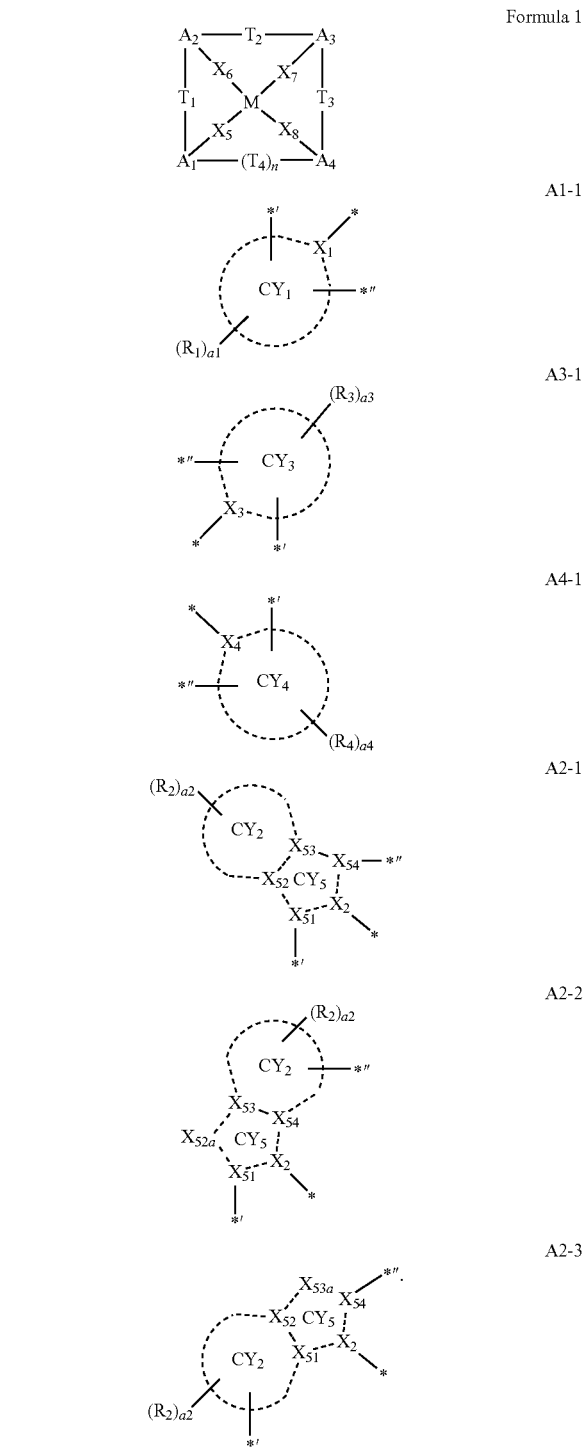

In Formula 1,
M may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), in Formula 1, two bonds selected from a bond between $A_1$ or $X_5$ and M, a bond between $A_2$ or $X_6$ and M, a bond between $A_3$ or $X_7$ and M, and a bond between $A_4$ or $X_8$ and M may each be a covalent bond, and the others thereof may each be a coordinate bond, in Formula 1, $A_1$ may be a ring represented by Formula A1-1, and in Formula A1-1, * indicates a binding site to M in Formula 1, *' indicates a binding site to $T_1$ in Formula 1, and *'' indicates a binding site to $T_4$ in Formula 1, in Formula 1, $A_2$ may be a ring represented by one selected from Formulae A2-1 to A2-3, and in Formulae A2-1 to A2-3, * indicates a binding site to M in Formula 1, *' indicates a binding site to $T_1$ in Formula 1, and *'' indicates a binding site to $T_2$ in Formula 1, in Formula 1, $A_3$ may be a ring represented by Formula A3-1, and in Formula A3-1, * indicates a binding site to M in Formula 1, *'' indicates a binding site to $T_2$ in Formula 1, and *' indicates a binding site to $T_3$ in Formula 1, in Formula 1, $A_4$ may be a first atom linked to $X_8$ or M, a non-cyclic moiety including the first atom linked to $X_8$ or M, or a ring represented by Formula A4-1, and in Formula A4-1, * indicates a binding site to M in Formula 1, *' indicates a binding site to $T_3$ in Formula 1, and *''' indicates a binding site to $T_4$ in Formula 1, the first atom may be B, P, N, C, Si, O, or S, in Formulae A1-1, A2-1 to A2-3, A3-1, and A4-1, $X_1$, $X_3$, $X_4$, and $X_{51}$ to $X_{54}$ may each independently be N or C, wherein at least one of $X_{51}$ and $X_{54}$ is N, $X_2$ may be N, $X_{52a}$ and $X_{53a}$ may each independently be N or C(R'), ring $CY_1$ to ring $CY_4$ may each independently be selected from a $C_5$-$C_{30}$ carbocyclic group and a $C_1$-$C_{30}$ heterocyclic group, ring $CY_5$ may be a $C_1$-$C_3$ heterocyclic group, in Formula 1, $X_5$ to $X_8$ may each independently be a single bond, O, S, B($R_5$), N($R_5$), P($R_5$), C($R_5$)($R_6$), Si($R_5$)($R_6$), Ge($R_5$)($R_6$), C(=O), B($R_5$)($R_6$), N($R_5$)($R_6$), or P($R_5$)($R_6$), $T_1$ to $T_4$ may each independently be selected from a single bond, a double bond, *—N($R_7$)—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—O—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', and * and *' each indicate a binding site to a neighboring atom, $R_7$ and $R_8$ may optionally be linked via a single bond, a double bond, or a first linking group to form a substituted or unsubstituted $C_5$-$C_{30}$ carbocyclic group or a substituted or unsubstituted $C_1$-$C_{30}$ heterocyclic group, n may be 0 or 1, wherein, when n is 0, $T_4$ does not exist and $CY_1$ and $CY_4$ are not linked, $R_1$ to $R_8$ and R' may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), a1 to a4 may each independently be 0, 1, 2, 3, 4, or 5, at least two neighboring groups selected from $R_1$ to $R_8$ and R' may optionally be linked to form a substituted or unsubstituted $C_5$-$C_{30}$ carbocyclic group or a substituted or unsubstituted $C_1$-$C_{30}$ heterocyclic group, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, Cl, —Br, —I, —CD$_3$, —CD$_2$H, —CDH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —CD$_3$, —CD$_2$H, —CDH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), and Q$_1$ to Q$_9$, Q$_{11}$ to Q$_{19}$, Q$_{21}$ to Q$_{29}$, and Q$_{31}$ to Q$_{39}$ may each independently be selected from hydrogen, deuterium, —F, —Cl, —Br, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryl group substituted with at least one selected from a C$_1$-C$_{60}$ alkyl group and a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group.

Another aspect of the present disclosure provides an organic light-emitting device including:

a first electrode;

a second electrode; and an organic layer disposed between the first electrode and the second electrode, wherein the organic layer includes an emission layer, and wherein the organic layer further includes at least one organometallic compound.

The organometallic compound in the organic layer may act as a dopant.

Another aspect of the present disclosure provides a diagnostic composition including at least one organometallic compound represented by Formula 1.

BRIEF DESCRIPTION OF THE DRAWING

These and/or other aspects will become apparent and more readily appreciated from the following description of the embodiments, taken in conjunction with FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment is represented by Formula 1 below:

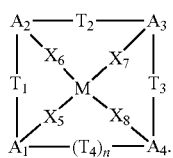

Formula 1

In Formula 1,

M may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au).

In an embodiment, M may be Pd or Pt, but embodiments of the present disclosure are not limited thereto.

In Formula 1, two bonds selected from a bond between $A_1$ or $X_5$ and M, a bond between $A_2$ or $X_6$ and M, a bond between $A_3$ or $X_7$ and M, and a bond between $A_4$ or $X_8$ and M may each be a covalent bond, and the others thereof may each be a coordinate bond. Therefore, the organometallic compound represented by Formula 1 may be electrically neutral.

In Formula 1, $A_1$ may be a ring represented by Formula A1-1, and in Formula A1-1, * indicates a binding site to M in Formula 1, *' indicates a binding site to $T_1$ in Formula 1, and *" indicates a binding site to $T_4$ in Formula 1, in Formula 1, $A_2$ may be a ring represented by one selected from Formulae A2-1 to A2-3, and in Formulae A2-1 to A2-3, * indicates a binding site to M in Formula 1, *' indicates a binding site to $T_1$ in Formula 1, and *" indicates a binding site $T_2$ in Formula 1, in Formula 1, $A_3$ may be a ring represented by Formula A3-1, and in Formula A3-1, * indicates a binding site to M in Formula 1, *" indicates a binding site to $T_2$ in Formula 1, and *' indicates a binding site to $T_3$ in Formula 1, and in Formula 1, $A_4$ may be a first atom linked to $X_8$ or M, a non-cyclic moiety including the first atom linked to $X_8$ or M, or a ring represented by Formula A4-1, and in Formula A4-1, * indicates a binding site to M in Formula 1, *' indicates a binding site to $T_3$ in Formula 1, and *" indicates a binding site to $T_4$ in Formula 1:

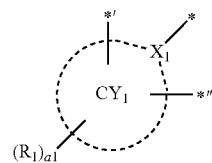

A1-1

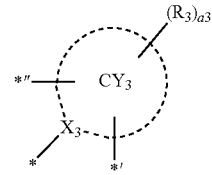

A3-1

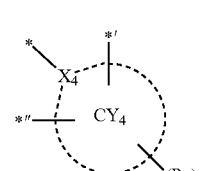

A4-1

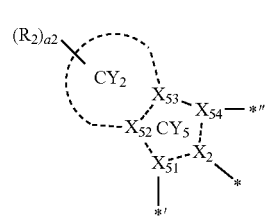

A2-1

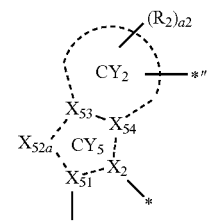

A2-2

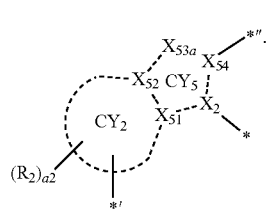

A2-3

The first atom may be B, P, N, C, Si, O, or S.

In an embodiment, the first atom may be O, but embodiments of the present disclosure are not limited thereto.

The non-cyclic moiety including the first atom linked to $X_8$ or M may be *—B($R_{41}$)—*', *—P($R_{41}$)—*', *—N ($R_{41}$)—*', *—C($R_{41}$)($R_{42}$)—*', *—S i($R_{41}$)($R_{42}$)—*', *—B ($R_{41}$)—C(=O)—*', *—P($R_{41}$)—C(=O)—*', *—N($R_{41}$)—C(=O)—*', *—C($R_{41}$)($R_{42}$)—C(=O)—*', *—Si($R_{41}$) ($R_{42}$)—C(=O)—*', *—O—C(=O)—*', or *—S—C (=O)—*' (wherein $R_{41}$ and $R_{42}$ are the same as described in connection with $R_4$, * indicates a binding site to M in Formula 1, and *' indicates a binding site to $T_3$ in Formula 1), but embodiments of the present disclosure are not limited thereto.

In Formulae A1-1, A2-1 to A2-3, A3-1, and A4-1, $X_1$, $X_3$, and $X_4$ may each independently be N or C, and $X_2$ may be N.

For example, $X_1$ may be C, $X_2$ may be N, $X_3$ may be C, and $X_4$ may be N; $X_1$ may be C, $X_2$ may be N, $X_3$ may be N, and $X_4$ may be C; $X_1$ may be C, $X_2$ may be N, $X_3$ may be N, and $X_4$ may be N; $X_1$ may be N, $X_2$ may be N, $X_3$ may be C, and $X_4$ may be N; may be N, $X_2$ may be N, $X_3$ may be N, and $X_4$ may be C; or $X_1$ may be N, $X_2$ may be N, $X_3$ may be N, and $X_4$ may be N, but embodiments of the present disclosure are not limited thereto.

In Formulae A2-1 to A2-3, $X_{51}$ to $X_{54}$ may each independently be N or C, wherein at least one of $X_{51}$ and $X_{54}$ is N, and $X_{52a}$ and $X_{53a}$ are each independently N or C(R'). R' will be described below.

For example, $X_{51}$ may be C, and $X_{54}$ may be N; or $X_{51}$ may be N, and $X_{54}$ may be C.

In an embodiment, in Formula A2-1, $X_{51}$ may be C, $X_{52}$ may be C, $X_{53}$ may be C, and $X_{54}$ may be N; or $X_{51}$ may be N, $X_{52}$ may be C, $X_{53}$ may be C, and $X_{54}$ may be C.

In an embodiment, in Formula A2-2, $X_{51}$ may be C, $X_{52a}$ may be C(R'), $X_{53}$ may be C, and $X_{54}$ may be N; or $X_{51}$ may be N, $X_{52a}$ may be C(R'), $X_{53}$ may be C, and $X_{54}$ may be C.

In an embodiment, in Formula A2-3, $X_{51}$ may be C, $X_{52}$ may be C, $X_{53a}$ may be C(R'), and $X_{54}$ may be N; or $X_{51}$ may be N, $X_{52}$ may be C, $X_{53a}$ may be C(R'), and $X_{54}$ may be C, but embodiments of the present disclosure are not limited thereto.

In Formulae A1-1, A2-1 to A2-3, A3-1, and A4-1, ring $CY_1$ to ring $CY_4$ may each independently be selected from a $C_5$-$C_{30}$ carbocyclic group and a $C_1$-$C_{30}$ heterocyclic group.

For example, ring $CY_1$ to ring $CY_4$ may each independently be selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a pyrrole group, a thiophene group, a furan group, an indole group, an isoindole group, a benzoborole group, a benzophosphole group, an indene group, a benzosilole group, a benzogermole group, a benzothiophene group, a benzoselenophene group, a benzofuran group, a carbazole group, a benzocarbazole group, a dibenzocarbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, an acridine group, a quinoxaline group, a quinazoline group, a phenanthroline group, a pyrazole group, an imidazole group, a triazole group, a tetrazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group.

In some embodiments, ring $CY_1$ to ring $CY_4$ may each independently be selected from: i) a first ring, ii) a second ring, iii) a condensed ring in which at least two second rings are condensed, and iv) a condensed ring in which at least one first ring and at least one second ring are condensed, wherein the first ring may be selected from a cyclopentadiene group, a furan group, a thiophene group, a pyrrole group, a silole group, an oxazole group, an isoxazole group, an oxadiazole group, an isozadiazole group, an oxatriazole group, an isoxatriazole group, a thiazole group, an isothiazole group, a thiadiazole group, an isothiadiazole group, a thiatriazole group, an isothiatriazole group, a pyrazole group, an imidazole group, a triazole group, a tetrazole group, an azasilole group, a diazasilole group, and a triazasilole group, and the second ring may be selected from a cyclohexane group, a cyclohexene group, an adamantane group, a norbornane group, a norbornene group, a benzene group, a pyridine group, a pyrimidine group, a pyrazine group, a pyridazine group, and a triazine group.

In an embodiment, ring $CY_1$ to ring $CY_4$ may each independently be selected from a benzene group, a naphthalene group, an anthracene group, a cyclopentadiene group, a 1,2,3,4-tetrahydronaphthalene group, a pyrrole group, a thiophene group, a furan group, an indole group, an isoindole group, an indene group, a benzosilole group, a benzothiophene group, a benzoselenophene group, a benzofuran group, a carbazole group, a benzocarbazole group, a benzocarbazole group, a dibenzocarbazole group, a fluorene group, a dibenzosilole group, a dibenzothiophene group, a dibenzoselenophene group, a dibenzofuran group, a pyridine group, a pyrimidine group, a pyrazine group, a pyridazine group, a triazine group, a quinoline group, an isoquinoline group, an acridine group, a quinoxaline group, a quinazoline group, a phenanthroline group, a pyrazole group, an imidazole group, a triazole group, a tetrazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, and a benzothiadiazole group.

In one or more embodiments, ring $CY_1$ to ring $CY_4$ may each independently be selected from a benzene group, a naphthalene group, a cyclopentadiene group, a pyrrole group, an indole group, an isoindole group, an indene group, a benzothiophene group, a benzofuran group, a carbazole group, a benzocarbazole group, a dibenzocarbazole group, a pyridine group, a quinoline group, an isoquinoline group, an acridine group, an imidazole group, a benzopyrazole group, and a benzimidazole group, but embodiments of the present disclosure are not limited thereto.

In Formula 1, $X_5$ to $X_8$ may each independently be a single bond, O, S, B($R_5$), N($R_5$), P($R_5$), C($R_5$)($R_6$), Si($R_5$)($R_6$), Ge($R_5$)($R_6$), C(=O), B($R_5$)($R_6$), N($R_5$)($R_6$), or P($R_5$)($R_6$).

For example, $X_5$, $X_7$, and $X_8$ may each independently be a single bond, O, S, or N($R_5$), and $X_6$ may be a single bond.

In an embodiment, $X_5$, $X_7$, and $X_8$ may each independently be a single bond or O, and $X_6$ may be a single bond.

In one or more embodiments, $X_5$ and $X_8$ may each independently be a single bond or O, and $X_6$ and $X_7$ may each independently be a single bond. However, embodiments of the present disclosure are not limited thereto.

In Formula 1, $T_1$ to $T_4$ may each independently be selected from a single bond, a double bond, *—N($R_7$)—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', wherein * and *' each independently indicate a binding site to a neighboring atom. $R_7$ and $R_8$ are the same as described above, and may optionally be linked each other via a single bond, a double bond, or a first linking group so that a substituted or unsubstituted $C_5$-$C_{30}$ carbocyclic group or a substituted or unsubstituted $C_1$-$C_{30}$ heterocyclic group may be formed.

The first linking group may be selected from *—N($R_9$)—*', *—B($R_9$)—*', *—P($R_9$)—*', *—C($R_9$)($R_{10}$)—*', *—Si($R_9$)($R_{10}$)—*', *—Ge($R_9$)($R_{10}$)—*', *—Se—*', *—O—*', *—C(=O)—*', *—S(=O)—*', *—S(=O)$_2$—*', *—C($R_9$)=*', *=C($R_9$)—*', *—C($R_9$)=C($R_{10}$)—*', *—C(=S)—*', and *—C≡C—*', wherein $R_9$ and $R_{10}$ may each independently have the same definition as $R_7$, and * and *' each independently indicate a binding site to a neighboring atom.

In an embodiment, $T_1$ to $T_4$ may each independently be a single bond, *—N($R_7$)—*' or *—C(=O)—*'.

In one or more embodiments, $T_1$ may be a single bond. For example, $T_1$ may be a single bond, and $T_2$ to $T_4$ may each independently be a single bond, *—N($R_7$)—*' or *—C(=O)—*', but embodiments of the present disclosure are not limited thereto.

In Formula 1, n may be 0 or 1, wherein, when n is 0, $T_4$ does not exist so that ring $CY_1$ and ring $CY_4$ are not linked each other.

In an embodiment, n may not be. In this case, the organometallic compound represented by Formula 1 may have three cyclometallated rings sharing M. When n is not 0, Formula 1 may be represented by Formula 1':

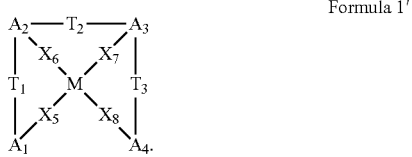

Formula 1'

In Formula 1', $A_1$ may be a ring represented by Formula A1-1', wherein, in Formula A1-1', * indicates a binding site to M in Formula 1', and *' indicates a binding site to $T_1$ in Formula 1', in Formula 1', $A_2$ and $A_3$ may respectively have the same definition as $A_2$ and $A_3$ in Formula 1, and in Formula 1', $A_4$ may be a first atom linked with $X_8$ or M, a non-cyclic moiety including the first atom, or a ring represented by Formula A4-1', wherein, in Formula A4-1', * indicates a binding site to M in Formula 1', and *' indicates a binding site to $T_3$ in Formula 1':

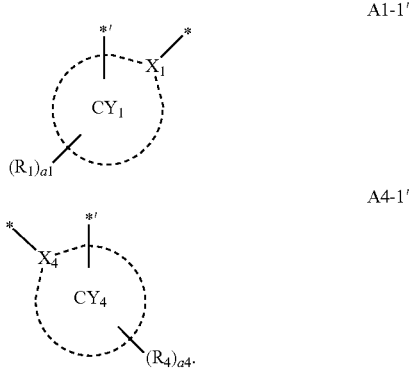

In Formula 1, $R_1$ to $R_8$ and R' may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$).

For example, $R_1$ to $R_8$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group, and a $C_1$-$C_{20}$ alkoxy group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, and —Si(Q$_{33}$)(Q$_{34}$)(Q$_{35}$); and —N(Q$_1$)(Q$_2$), —Si(Q$_3$)(Q$_4$)(Q$_5$), —B(Q$_6$)(Q$_7$), and —P(=O)(Q$_8$)(Q$_9$), and Q$_1$ to Q$_9$ and Q$_{33}$ to Q$_{35}$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group.

In an embodiment, R$_1$ to R$_8$ and R' may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-22, groups represented by Formulae 10-1 to 10-143, and —Si(Q$_3$)(Q$_4$)(Q$_5$), but embodiments of the present disclosure are not limited thereto:

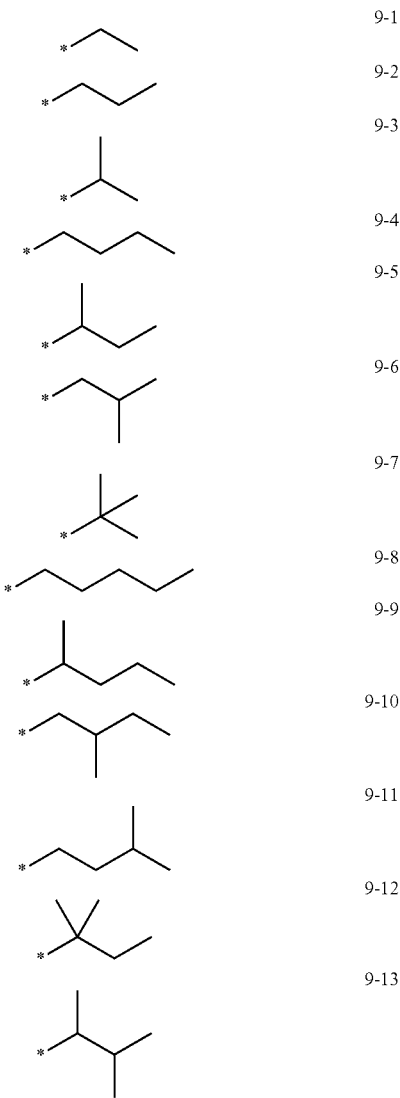

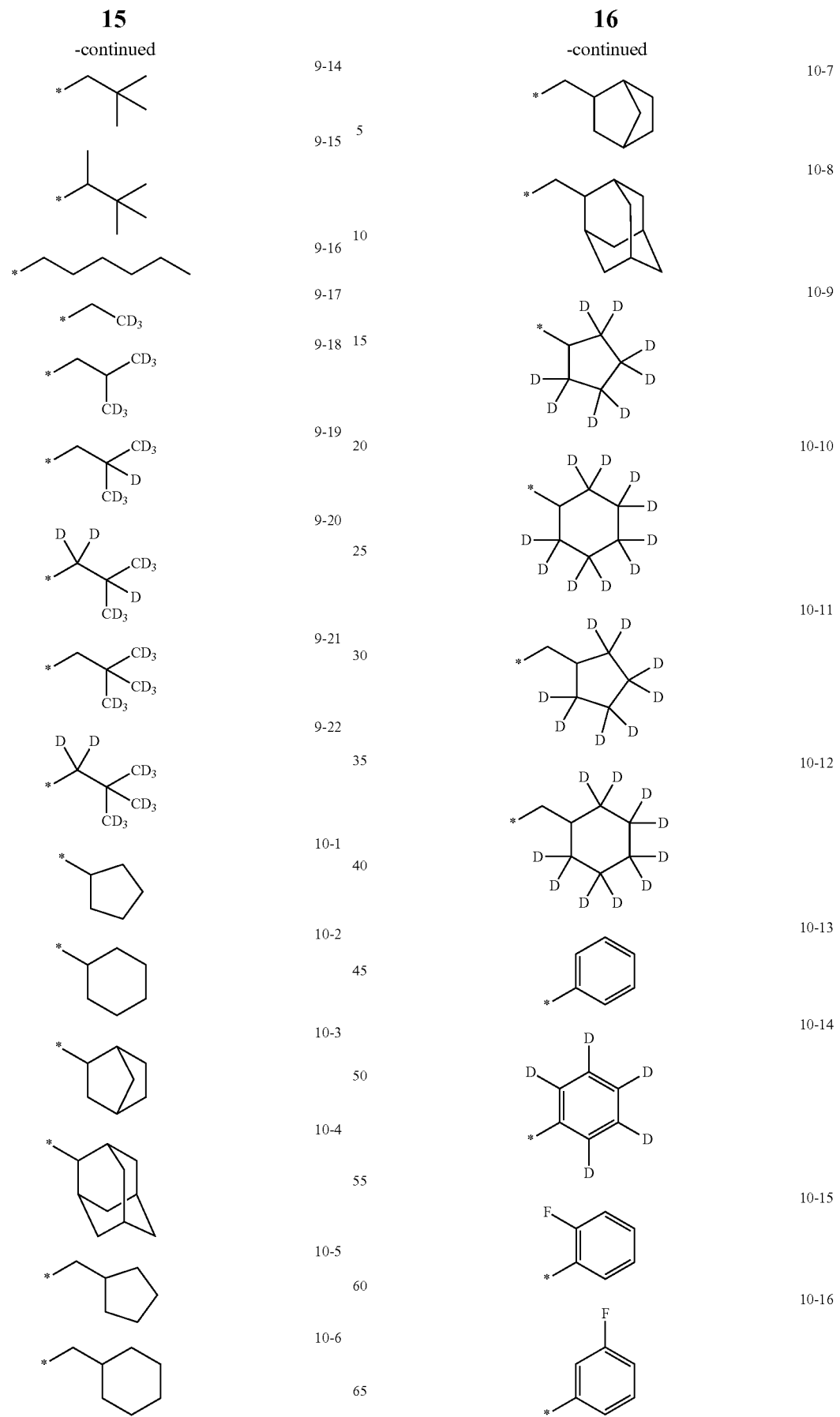

-continued
| | | |
|---|---|---|
| 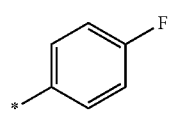 | 10-17 | |
| 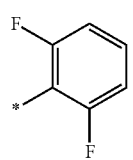 | 10-18 | |
| 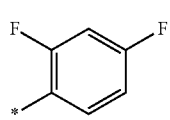 | 10-19 | |
| 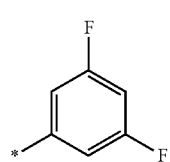 | 10-20 | |
| 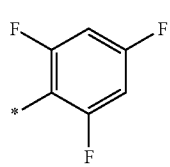 | 10-21 | |
| 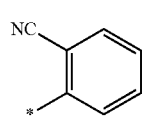 | 10-22 | |
| 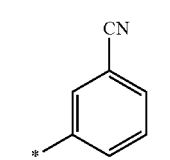 | 10-23 | |
| 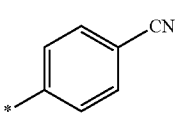 | 10-24 | |
| 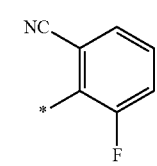 | 10-25 | |
| 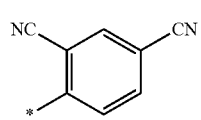 | 10-26 | |
| 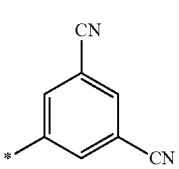 | 10-27 | |
-continued
| | | |
|---|---|---|
| 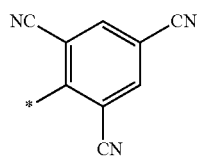 | 10-28 | |
| 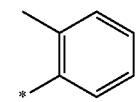 | 10-29 | |
| 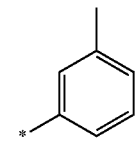 | 10-30 | |
| 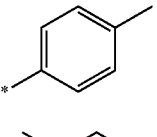 | 10-31 | |
| 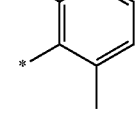 | 10-32 | |
| 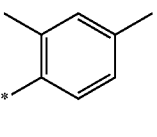 | 10-33 | |
| 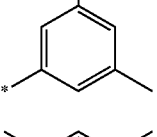 | 10-34 | |
| 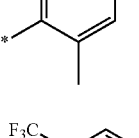 | 10-35 | |
| 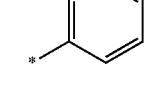 | 10-36 | |
| 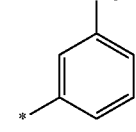 | 10-37 | |
| 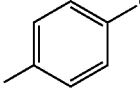 | 10-38 | |

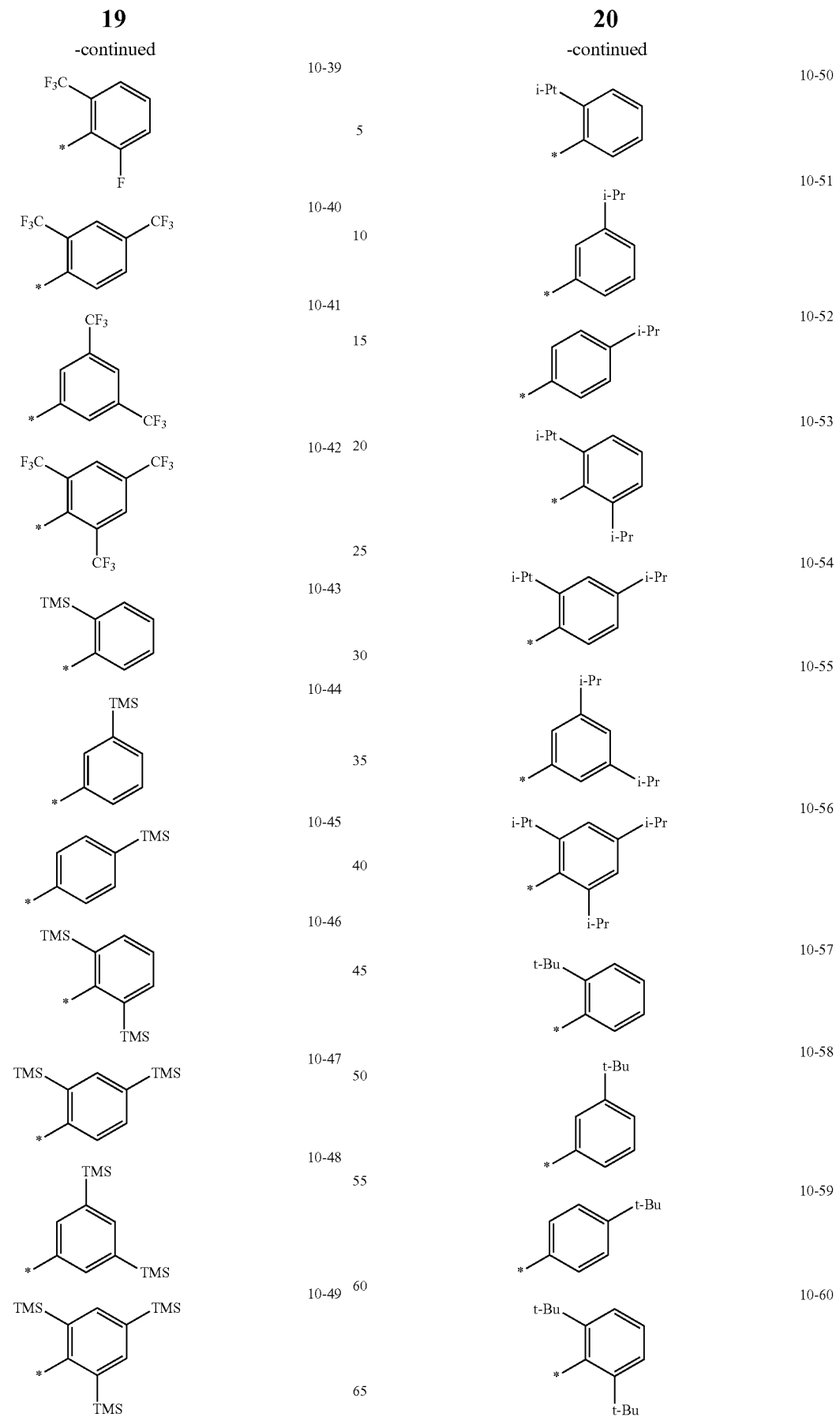

-continued
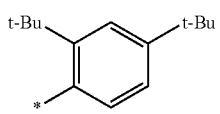 10-61
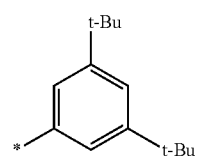 10-62
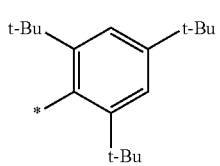 10-63
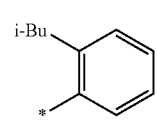 10-64
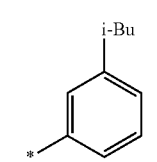 10-65
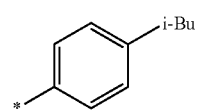 10-66
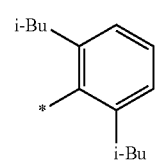 10-67
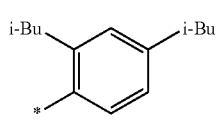 10-68
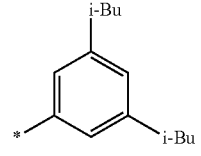 10-69
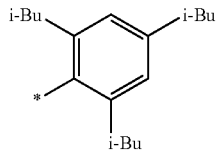 10-70
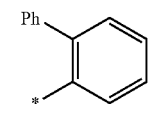 10-71
-continued
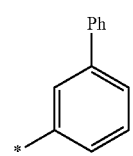 10-72
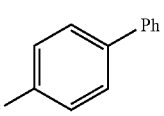 10-73
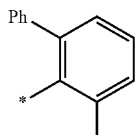 10-74
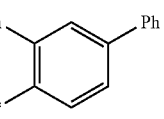 10-75
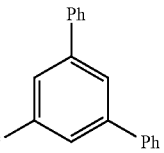 10-76
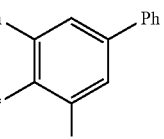 10-77
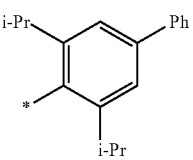 10-78
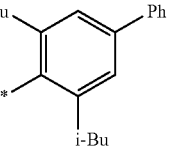 10-79
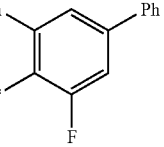 10-80
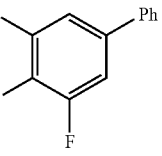 10-81

10-82 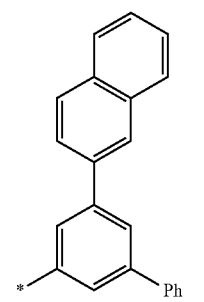
10-83 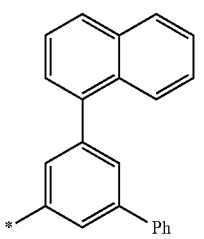
10-84 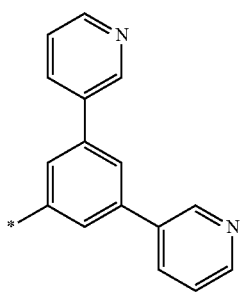
10-85 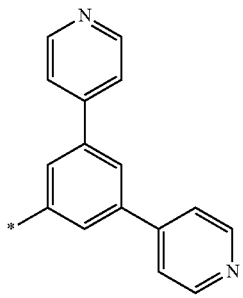
10-86 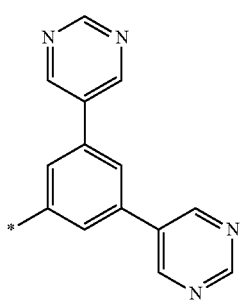
10-87 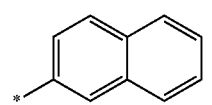
10-88 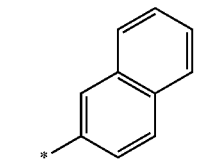
10-89 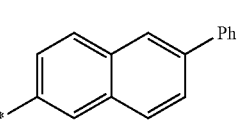
10-90
10-91
10-92 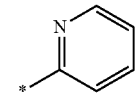
10-93 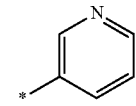
10-94 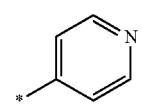
10-95 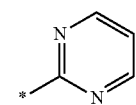
10-96 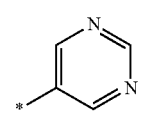
10-97 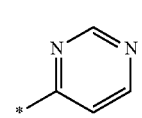
10-98 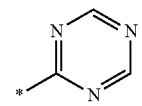
10-99
10-100

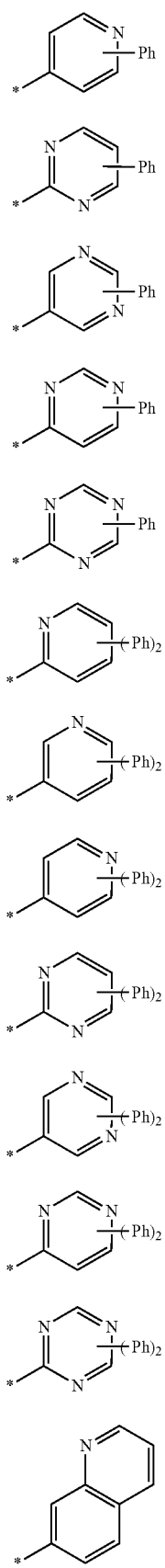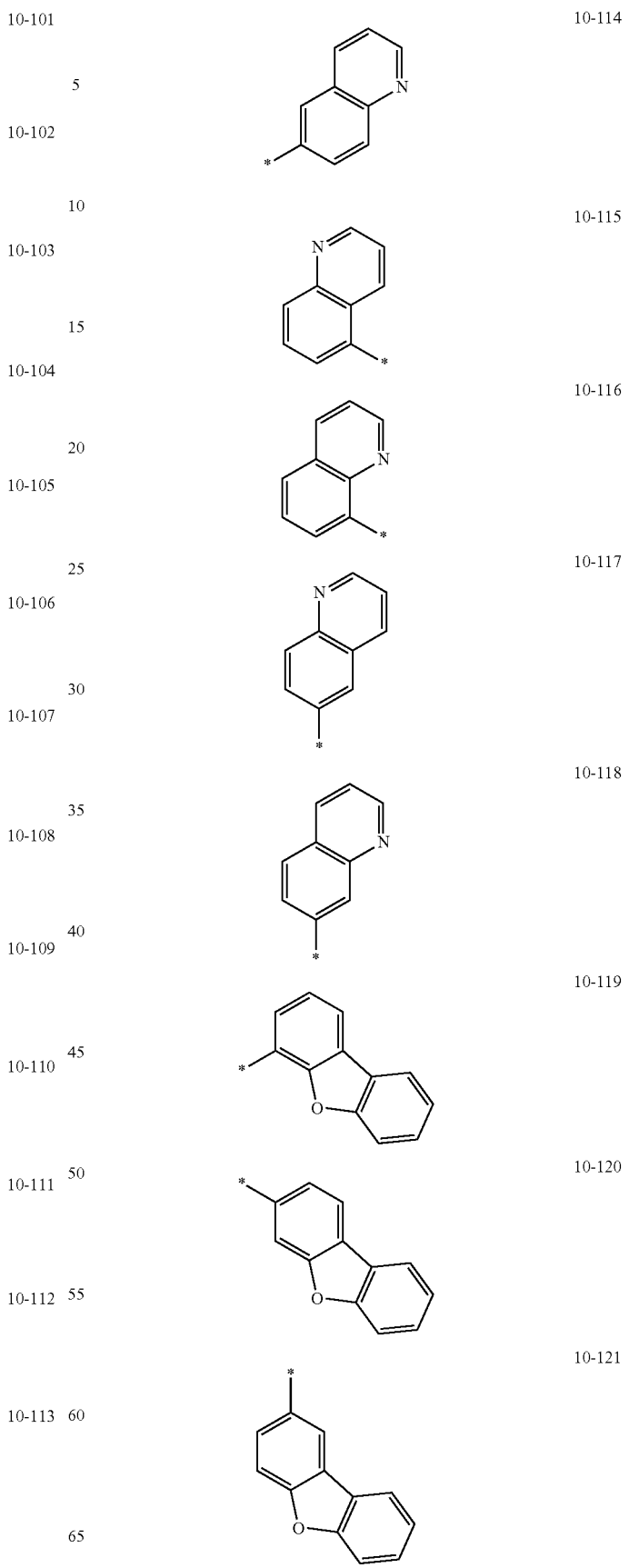

10-122 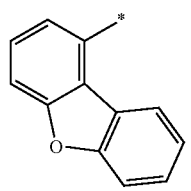
10-123 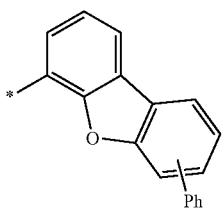
10-124 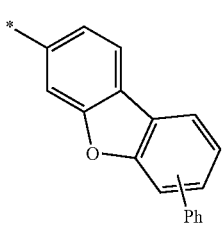
10-125 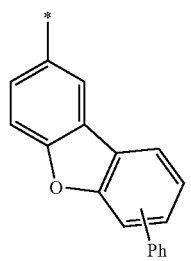
10-126 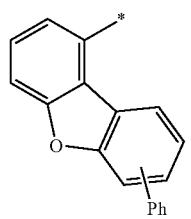
10-127 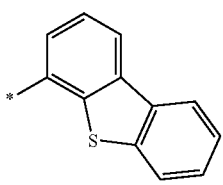
10-128 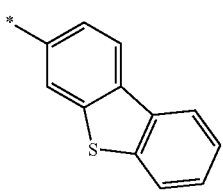
10-129 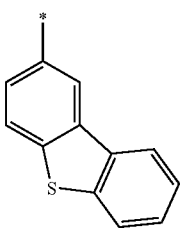
10-130 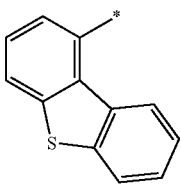
10-131 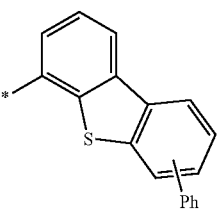
10-132 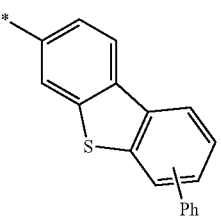
10-133 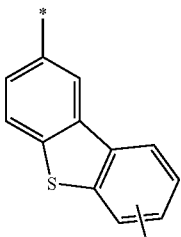
10-134 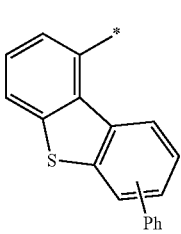
10-135 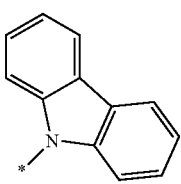

-continued

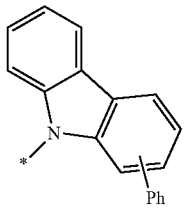
10-136

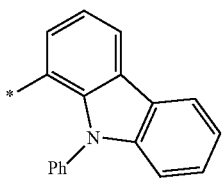
10-137

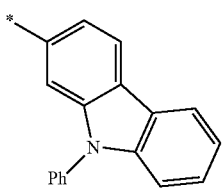
10-138

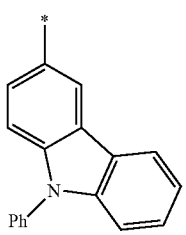
10-139

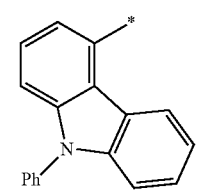
10-140

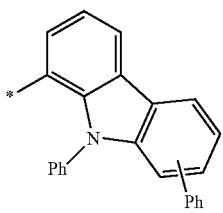
10-141

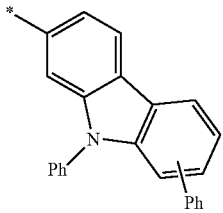
10-142

-continued

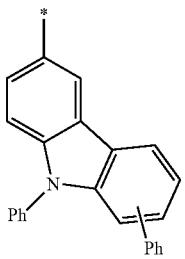
10-143

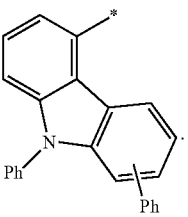
10-144

In Formulae 9-1 to 9-22 and 10-1 to 10-143, i-Pr indicates an iso-propyl group, i-Bu indicates an iso-butyl group, t-Bu indicates a tert-butyl group, TMS indicates a trimethylsilyl group, Ph indicates a phenyl group, and * indicates a binding site to a neighboring atom.

In Formulae A1-1, A2-1 to A2-3, A3-1, and A4-1, a1 to a4 respectively indicate the number of groups $R_1$ to $R_4$, and may each independently be 0, 1, 2, 3, 4, or 5 (for example, 0, 1, 2, or 3). When a1 is two or more, two or more groups $R_1$ may be identical to or different from each other, when a2 is two or more, two or more groups $R_2$ may be identical to or different from each other, when a3 is two or more, two or more groups $R_3$ may be identical to or different from each other, and when a4 is two or more, two or more groups $R_4$ may be identical to or different from each other.

In Formulae A1-1, A2-1 to A2-3, A3-1, and A4-1, at least two neighboring groups selected from $R_1$ to $R_4$ may optionally be linked to form a substituted or unsubstituted $C_5$-$C_{30}$ carbocyclic group or a substituted or unsubstituted $C_1$-$C_{30}$ heterocyclic group.

For example, i) a substituted or unsubstituted $C_5$-$C_{30}$ carbocyclic group or a substituted or unsubstituted $C_1$-$C_{30}$ heterocyclic group, formed by linking two of a plurality of neighboring groups $R_1$ in Formula A1-1, ii) a substituted or unsubstituted $C_5$-$C_{30}$ carbocyclic group or a substituted or unsubstituted $C_1$-$C_{30}$ heterocyclic group, formed by linking two of a plurality of neighboring groups $R_2$ in Formulae A2-1 to A2-3, iii) a substituted or unsubstituted $C_5$-$C_{30}$ carbocyclic group or a substituted or unsubstituted $C_1$-$C_{30}$ heterocyclic group, formed by linking two of a plurality of neighboring groups $R_3$ in Formula A3-1, iv) a substituted or unsubstituted $C_5$-$C_{30}$ carbocyclic group or a substituted or unsubstituted $C_1$-$C_{30}$ heterocyclic group, formed by linking two of a plurality of neighboring groups $R_4$ in Formula A4-1, v) a substituted or unsubstituted $C_5$-$C_{30}$ carbocyclic group or a substituted or unsubstituted $C_1$-$C_{30}$ heterocyclic group, formed by linking two of at least one neighboring $R_1$ and at least one neighboring $R_2$ in Formulae A1-1 and A2-1 to A2-3, vi) a substituted or unsubstituted $C_5$-$C_{30}$ carbocyclic group or a substituted or unsubstituted $C_1$-$C_{30}$ heterocyclic group, formed by linking two of at least one neighboring $R_2$ and at least one $R_3$ in Formulae A2-1 to A2-3 and A3-1, vii) a substituted or unsubstituted $C_5$-$C_{30}$ carbocyclic group or a substituted or unsubstituted $C_1$-$C_{30}$ heterocyclic group, formed by linking two of at least one neighboring $R_3$ and at least one group R₄ in Formulae A3-1 and A4-1, and viii) a substituted or unsubstituted $C_5$-$C_{30}$ carbocyclic group or a substituted or unsubstituted $C_1$-$C_{30}$ heterocyclic group, formed by at least one neighboring R₁ and at least one group R₄ in Formulae A1-1 and A4-1 may each independently be selected from:

- a cyclopentadiene group, a cyclohexadiene group, a cyclohexane group, a cycloheptane group, an adamantane group, a bicycle-heptane group, a bicycle-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group; and
- a cyclopentadiene group, a cyclohexadiene group, a cyclohexane group, a cycloheptane group, an adamantane group, a bicycle-heptane group, a bicycle-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group, each substituted with at least one $R_{10a}$, but embodiments of the present disclosure are not limited thereto.

$R_{10a}$ is the same as described in connection with $R_1$.

In the present disclosure, "an azabenzothiophene, an azabenzofuran, an azaindene, an azaindole, an azabenzosilole, an azadibenzothiophene, an azadibenzofuran, an azafluorene, an azacarbazole, and an azadibenzosilole" as used herein each refer to a hetero ring having the same backbone as "a benzothiophene, a benzofuran, an indene, an indole, a benzosilole, a dibenzothiophene, a dibenzofuran, a fluorene, a carbazole, and a dibenzosilole", in which at least one carbon constituting rings thereof is substituted with nitrogen.

In one or more embodiments, in Formula 1,
i) n may be 0, and A₁ may be represented by one selected from Formulae CY1-1 to CY1-34, or
ii) n may be 1, and A₁ may be represented by one selected from Formulae CY1-101 to CY1-123:

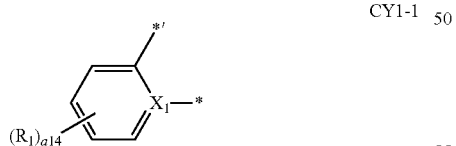

CY1-1

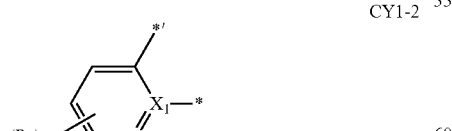

CY1-2

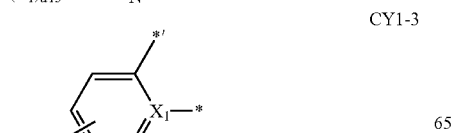

CY1-3

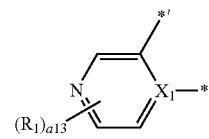

CY1-4

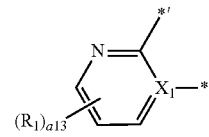

CY1-5

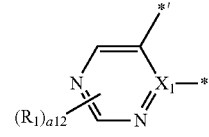

CY1-6

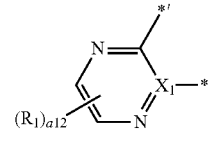

CY1-7

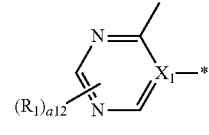

CY1-8

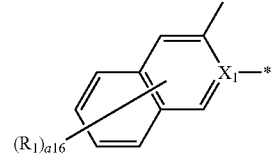

CY1-9

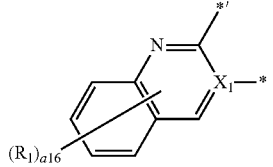

CY1-10

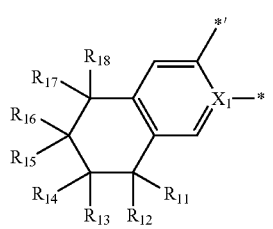

CY1-11

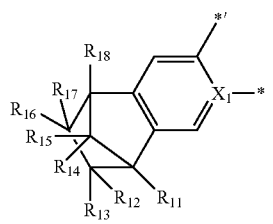

CY1-12

-continued
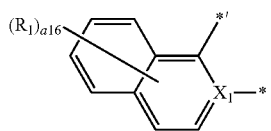  CY1-13
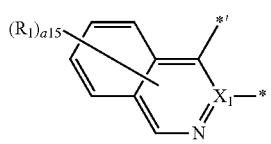  CY1-14
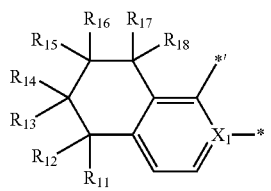  CY1-15
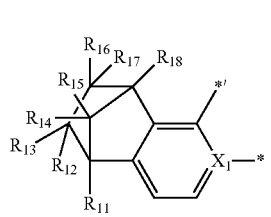  CY1-16
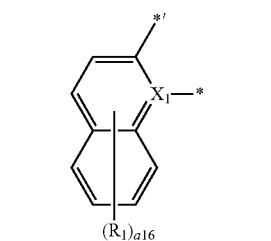  CY1-17
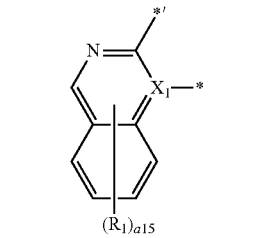  CY1-18
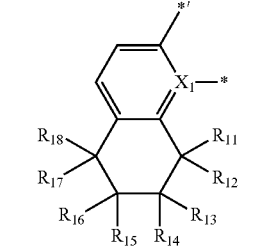  CY1-19
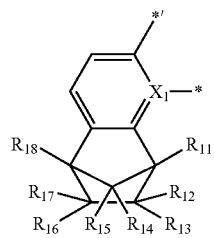  CY1-20
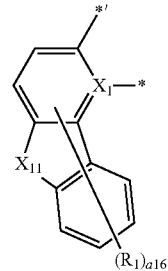  CY1-21
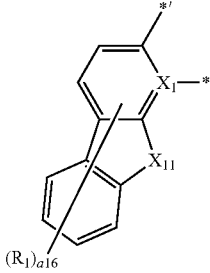  CY1-22
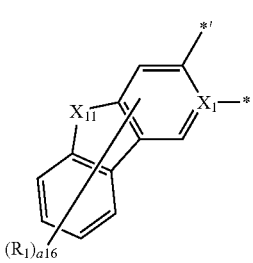  CY1-23
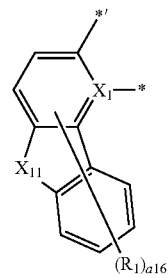  CY1-24
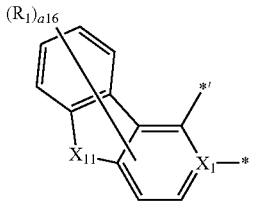  CY1-25

-continued
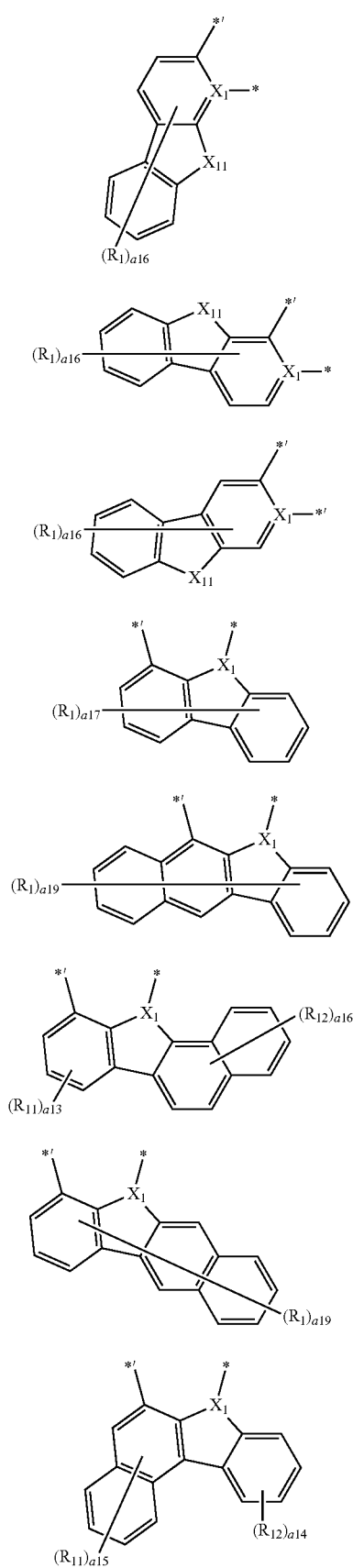
CY1-26
CY1-27
CY1-28
CY1-29
CY1-30
CY1-31
CY1-32
CY1-33
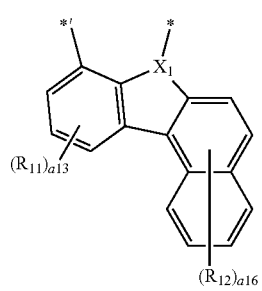
CY1-34
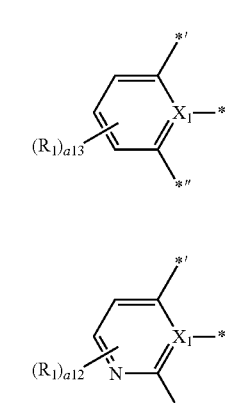
CY1-101
CY1-102
CY1-103
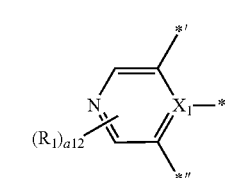
CY1-104
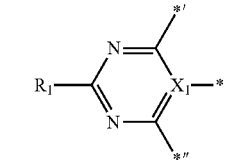
CY1-105
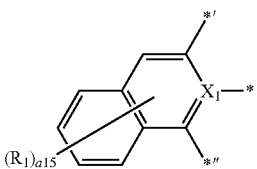
CY1-106
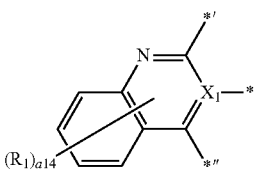
CY1-107

CY1-108 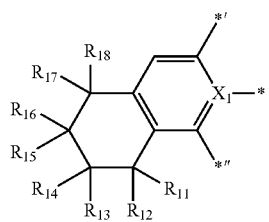
CY1-109 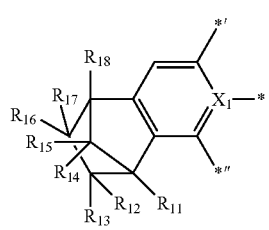
CY1-110 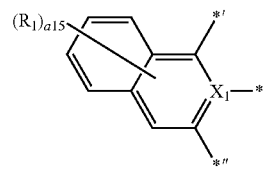
CY1-111 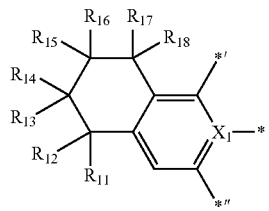
CY1-112 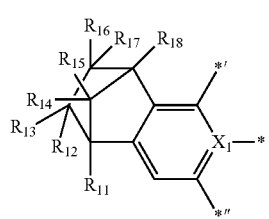
CY1-113 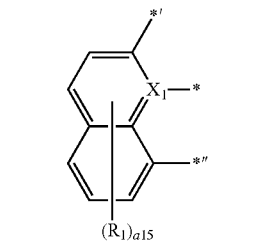
CY1-114 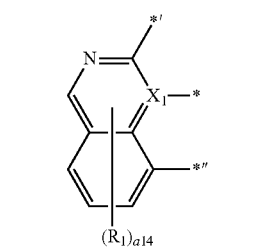
CY1-115 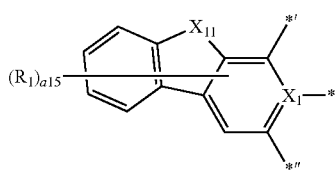
CY1-116 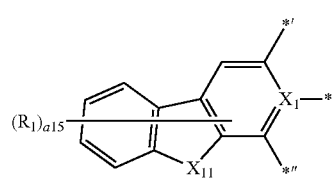
CY1-117 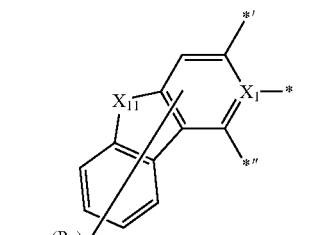
CY1-118 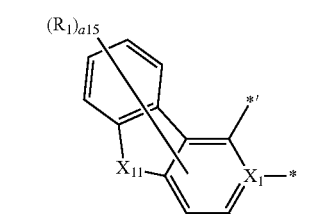
CY1-119 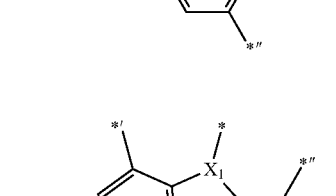
CY1-120 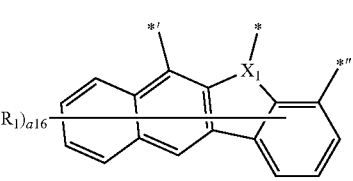
CY1-121 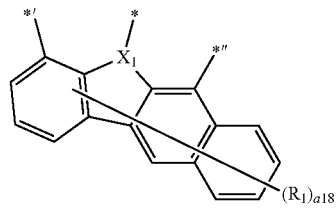

CY1-122

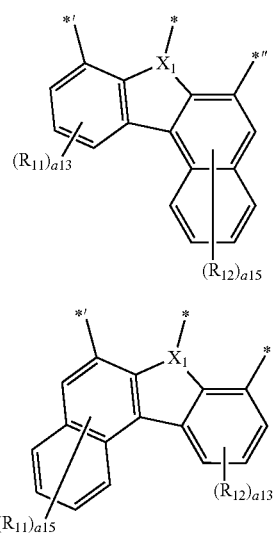

CY1-123

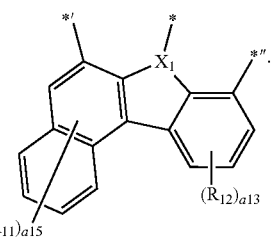

In Formulae CY1-1 to CY1-34 and CY1-101 to CY1-123,
$X_1$ and $R_1$ are each independently the same as described herein,
$X_{11}$ may be O, S, $N(R_{11})$, $C(R_{11})(R_{12})$, or $Si(R_{11})(R_{12})$,
$R_{11}$ to $R_{18}$ are each independently the same as described in connection with $R_1$,
a19 may be an integer from 0 to 9,
a18 may be an integer from 0 to 8,
a17 may be an integer from 0 to 7,
a16 may be an integer from 0 to 6,
a15 may be an integer from 0 to 5,
a14 may be an integer from 0 to 4,
a13 may be an integer from 0 to 3,
a12 may be an integer from 0 to 2,
* indicates a binding site to M in Formula 1,
*' indicates a binding site to $T_1$ in Formula 1, and
*" indicates a binding site to $T_4$ in Formula 1.

In one or more embodiments, $A_2$ in Formula 1 may be represented by one selected from Formulae CZ-1 to CZ-20:

CZ-1

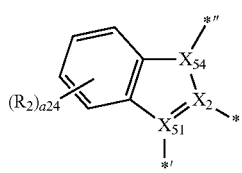

CZ-2

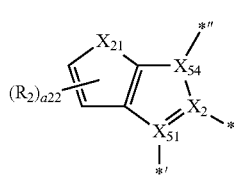

CZ-3

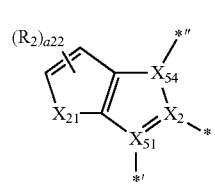

CZ-4

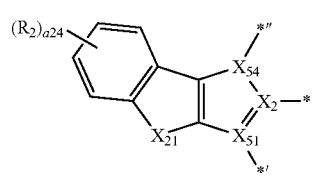

CZ-5

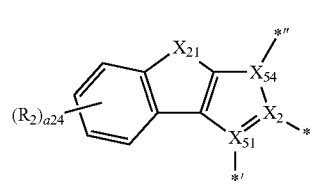

CZ-6

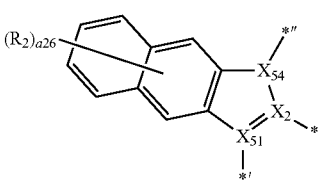

CZ-7

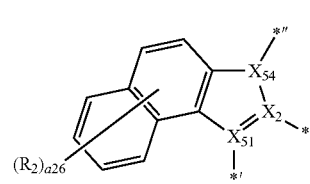

CZ-8

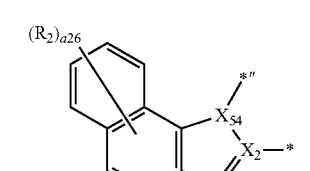

CZ-9

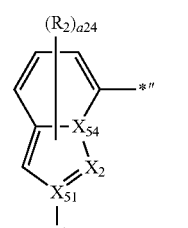

CZ-10

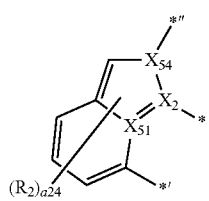

CZ-11

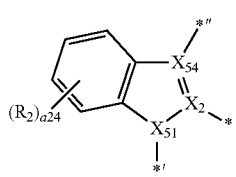

CZ-12
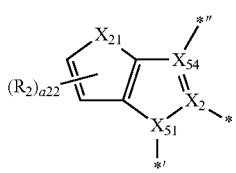

CZ-13
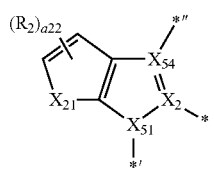

CZ-14
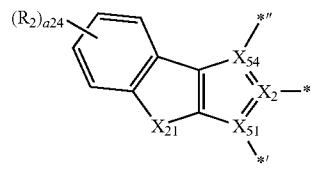

CZ-15
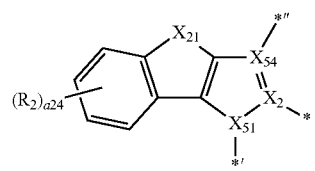

CZ-16
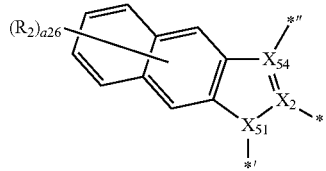

CZ-17
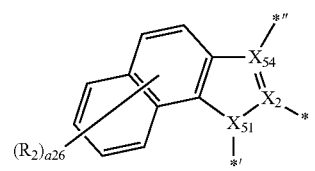

CZ-18
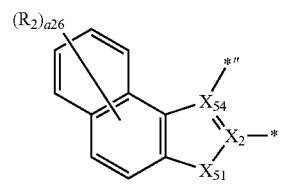

CZ-19
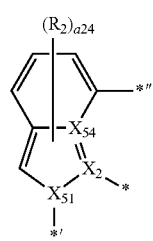

CZ-20
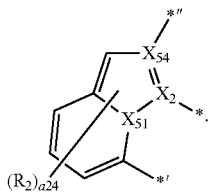

In Formulae CZ-1 to CZ-20, $X_2$, $X_{51}$, $X_{54}$, and $R_2$ are each independently the same as described herein, $X_{21}$ may be O, S, $N(R_{21})$, $C(R_{21})(R_{22})$, or $Si(R_{21})(R_{22})$, $R_{21}$ and $R_{22}$ are each independently the same as described in connection with $R_2$, a26 may be an integer from 0 to 6, a24 may be an integer from 0 to 4, a22 may be an integer from 0 to 2, \* indicates a binding site to M in Formula 1, \*' indicates a binding site to $T_1$ in Formula 1, and \*" indicates a binding site to $T_2$ in Formula 1.

In one or more embodiments, $A_3$ in Formula 1 may be represented by one selected from Formulae CY3-1 to CY3-40:

CY3-1
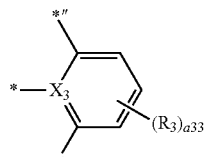

CY3-2
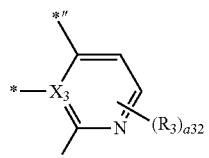

CY3-3
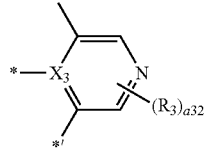

CY3-4
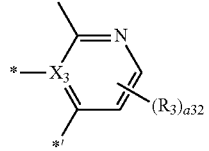

CY3-5
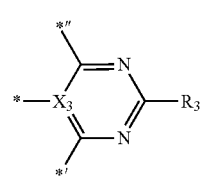

-continued
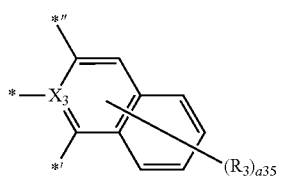 CY3-6
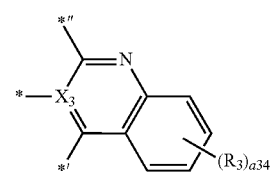 CY3-7
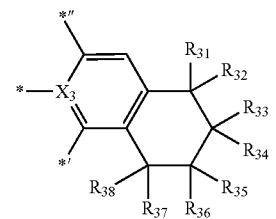 CY3-8
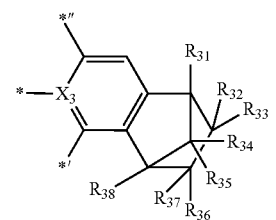 CY3-9
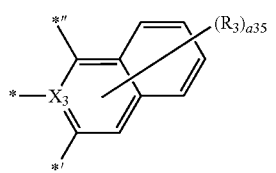 CY3-10
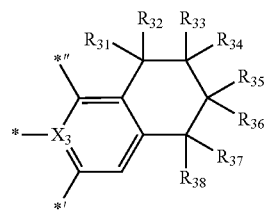 CY3-11
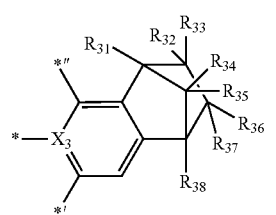 CY3-12
-continued
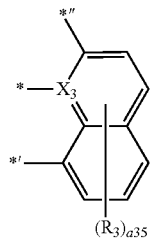 CY3-13
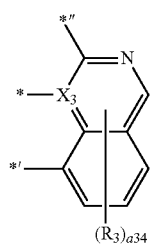 CY3-14
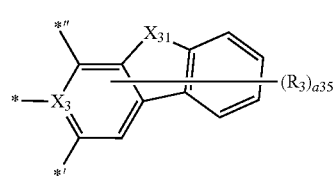 CY3-15
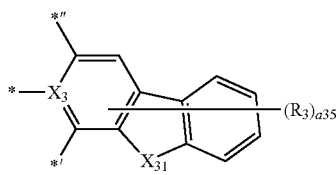 CY3-16
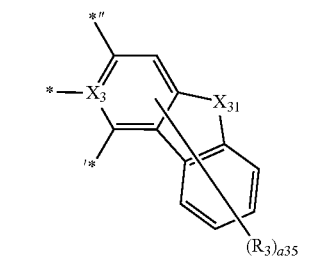 CY3-17
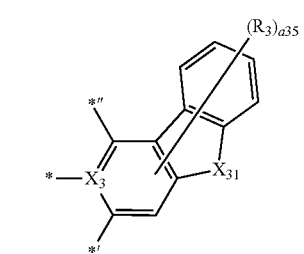 CY3-18
CY3-19

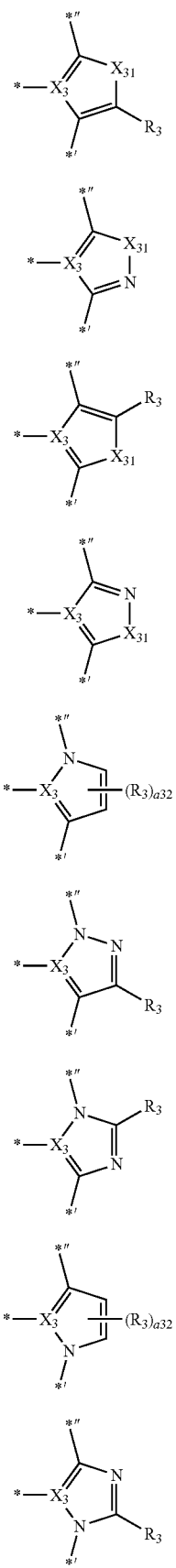
CY3-20
CY3-21
CY3-22
CY3-23
CY3-24
CY3-25
CY3-26
CY3-27
CY3-28
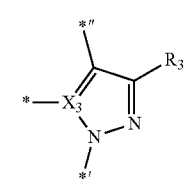
CY3-29
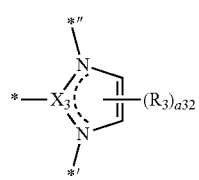
CY3-30
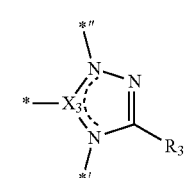
CY3-31
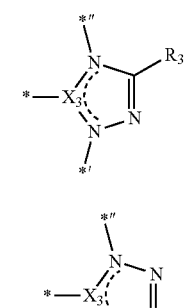
CY3-32
CY3-33
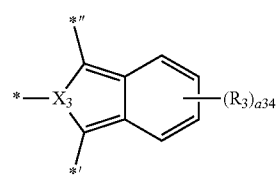
CY3-34
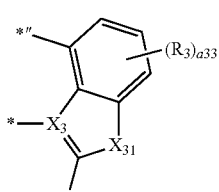
CY3-35
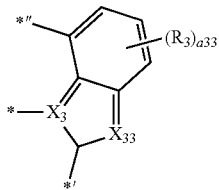
CY3-36

-continued

CY3-37
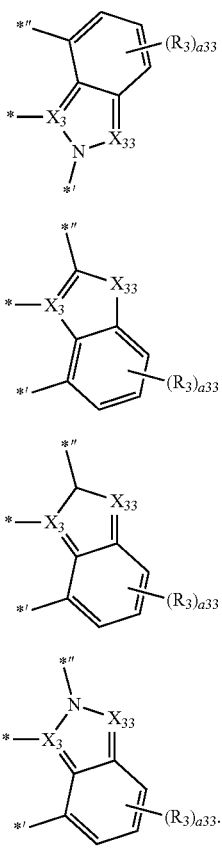

CY3-38

CY3-39

CY3-40

In Formulae CY3-1 to CY3-40,
$X_3$ and $R_3$ are each independently the same as described herein,
$X_{31}$ may be O, S, $N(R_{31})$, $C(R_{31})(R_{32})$, or $Si(R_{31})(R_{32})$,
$X_{33}$ may b N or $C(R_{31})$,
$R_{31}$ to $R_{38}$ are each independently the same as described in connection with $R_3$,
a37 may be an integer from 0 to 7,
a35 may be an integer from 0 to 5,
a34 may be an integer from 0 to 4,
a33 may be an integer from 0 to 3,
a32 may be an integer from 0 to 2,
indicates a binding site to M in Formula 1,
" indicates a binding site to $T_2$ in Formula 1, and
' indicates a binding site to $T_3$ in Formula 1.
In one or more embodiments, in Formula 1,
i) $A_4$ may be *—O—*' or *—S—*', and $T_3$ may be a single bond, *—$N(R_7)$—*', *—$B(R_7)$—*', *—$P(R_7)$—*', *—$C(R_7)(R_8)$—*', *—$Si(R_7)(R_8)$—*', *—$Ge(R_7)(R_8)$—*', or *—C(=O)—*',
ii) $A_4$ may be represented by one selected from Formulae A4(1) to A4(6), and $T_3$ may be a single bond,
iii) n may be 0, and $A_4$ may be represented by one selected from Formulae CY4-1 to CY4-35, or
iv) n may be 1, and $A_4$ may be represented by one selected from Formulae CY4-101 to CY4-124:

A4(1)
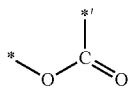

-continued

A4(2)
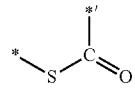

A4(3)
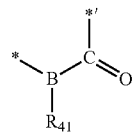

A4(4)
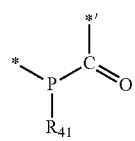

A4(5)
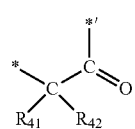

A4(6)
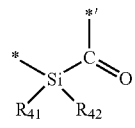

CY4-1
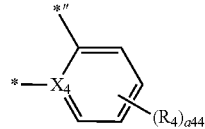

CY4-2
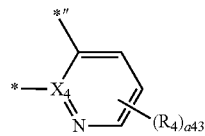

CY4-3
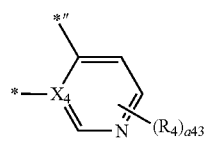

CY4-4
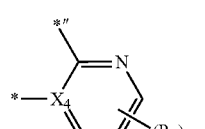

CY4-5
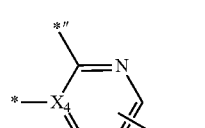

CY4-6
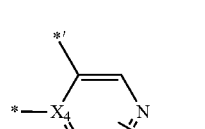

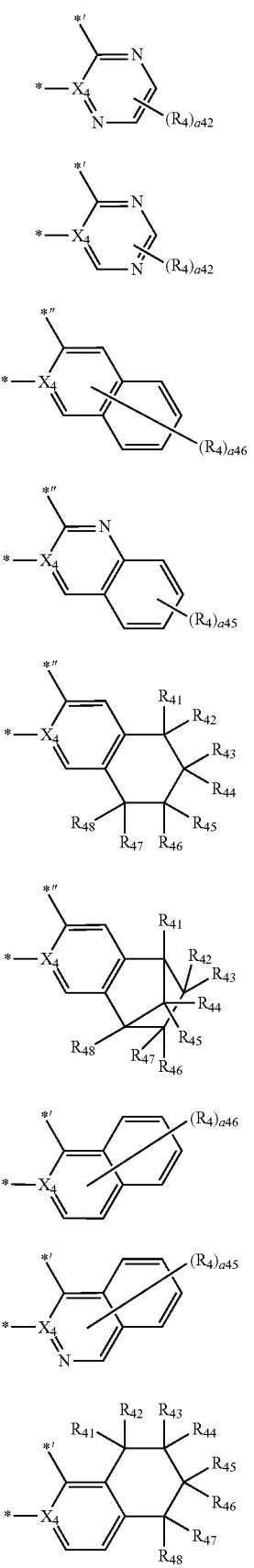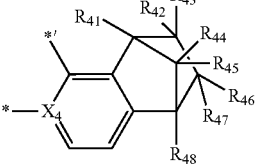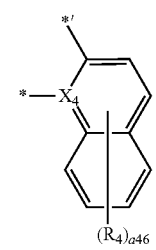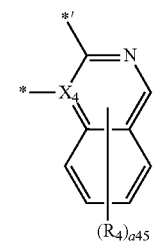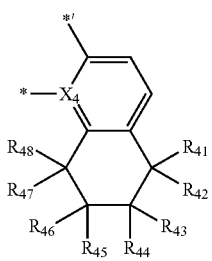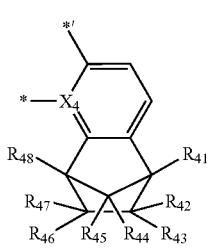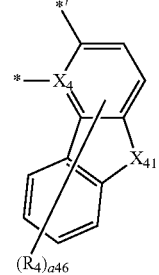

-continued
CY4-22
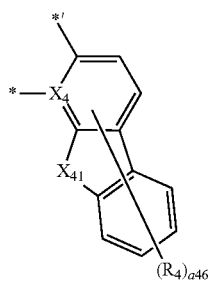
CY4-23
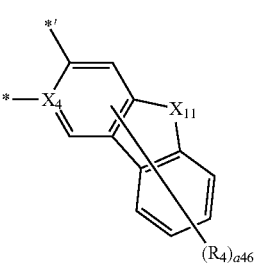
CY4-24
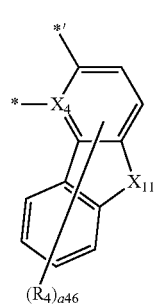
CY4-25
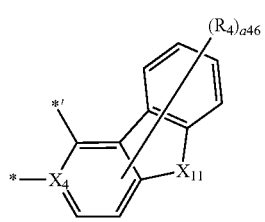
CY4-26
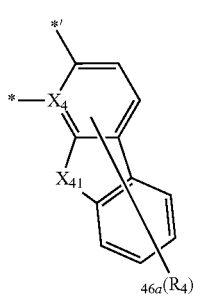
CY4-27
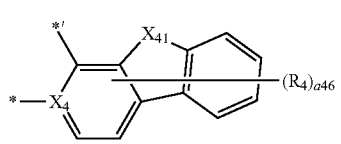
-continued
CY4-28
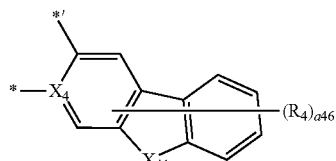
CY4-29
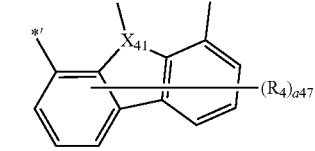
CY4-30
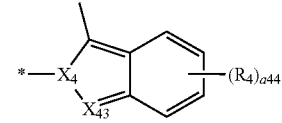
CY4-31
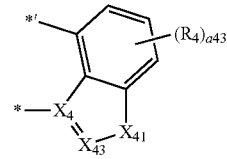
CY4-32
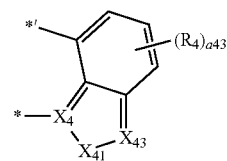
CY4-33
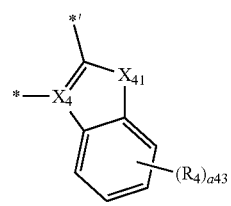
CY4-34
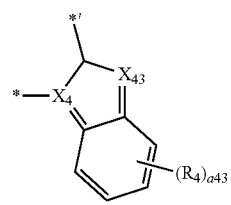
CY4-35
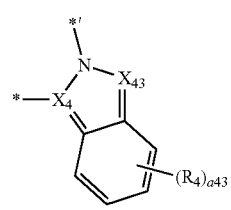
CY4-101

-continued
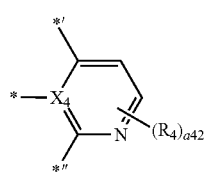
CY4-102
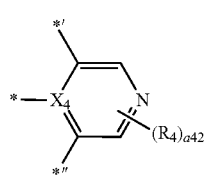
CY4-103
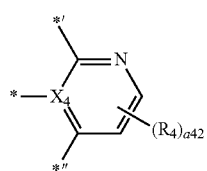
CY4-104
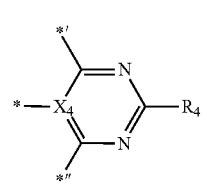
CY4-105
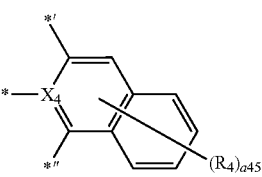
CY4-106
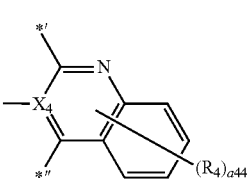
CY4-107
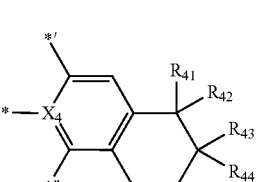
CY4-108
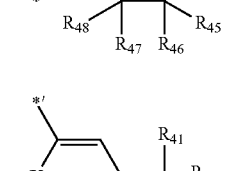
CY4-109
-continued
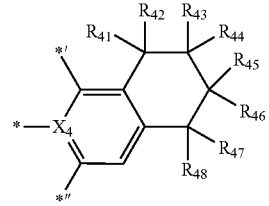
CY4-110
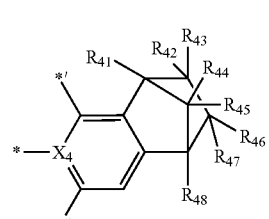
CY4-111
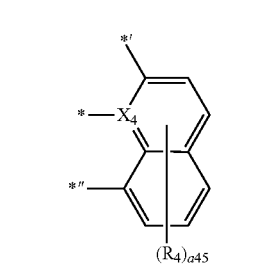
CY4-112
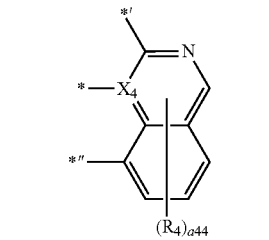
CY4-113
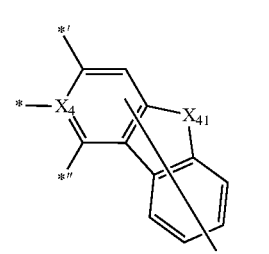
CY4-114
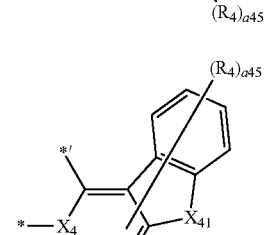
CY4-115
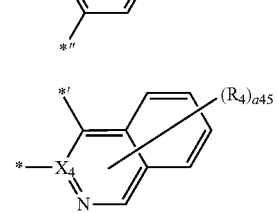
CY4-14

-continued

CY4-116
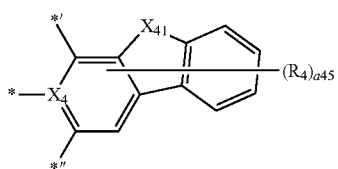

CY4-117
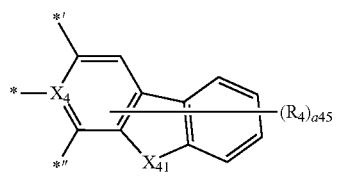

CY4-118
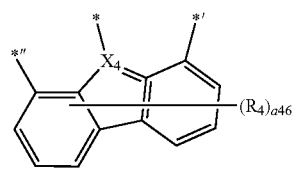

CY4-119
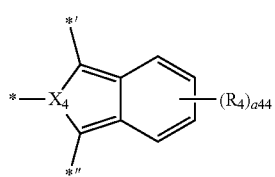

CY4-120
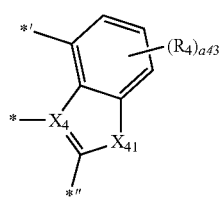

CY4-121
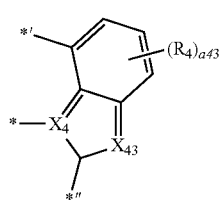

CY4-122
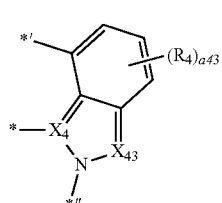

CY4-123
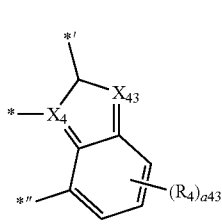

CY4-124
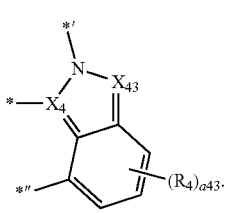

In Formulae A4(1) to A4(5), CY4-1 to CY4-35, and CY4-101 to CY4-124, $X_4$ and $R_4$ are each independently the same as described herein, $X_{41}$ may be O, S, N($R_{41}$), C($R_{41}$)($R_{42}$), or Si($R_{41}$)($R_{42}$), $X_{43}$ may be N or C($R_{41}$), $R_{41}$ to $R_{48}$ are each independently the same as described in connection with $R_4$, a47 may be an integer from 0 to 7, a46 may be an integer from 0 to 6, a45 may be an integer from 0 to 5, a44 may be an integer from 0 to 4, a43 may be an integer from 0 to 3, a42 may be an integer from 0 to 2, \* indicates a binding site to M in Formula 1, \*' indicates a binding site to $T_3$ in Formula 1, and \*" indicates a binding site to $T_4$ in Formula 1.

In one or more embodiments, in Formula 1, i) n may be 0, and a moiety represented by

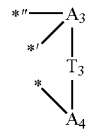

in Formula 1 may be represented by Formula CY34-1, or ii) n may be 1, a moiety represented by

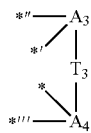

in Formula 1 may be represented by Formula CY34-2:

Formula CY34-1

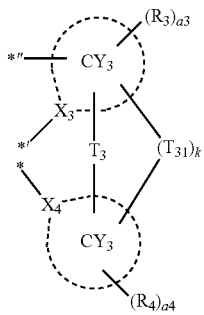

Formula CY34-2

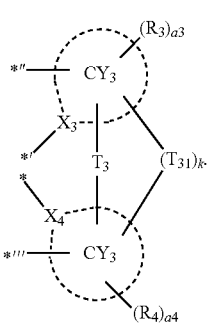

In Formulae CY34-1 and CY34-2,
$X_3$, $X_4$, $T_3$, $R_3$, $R_4$, a3, and a4 are each independently the same as described herein,
$T_{31}$ may be a single bond, O, S, $N(R_{41})$, $C(R_{41})(R_{42})$, or $Si(R_{41})(R_{42})$,
k may be 0, 1, 2, 3, 4, or 5, wherein, when k is 0, $T_{31}$ does not exist, and when k is two or more, two or more groups $T_{31}$ may be identical to or different from each other,
$R_{41}$ and $R_{42}$ are each independently the same as described in connection with $R_4$,
* and *' each indicate a binding site to M in Formula 1,
*" indicates a binding site to $T_2$ in Formula 1, and
*''' indicates a binding site to $T_4$ in Formula 1.
In Formula 1,
i) n may be 0, and a moiety represented by

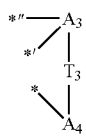

in Formula 1 may be represented by Formula CY34(1) or CY34(2), or
ii) n may be 1, and a moiety represented by

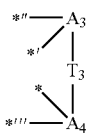

in Formula 1 may be represented by Formula CY34(3) or CY34(4), but embodiments of the present disclosure are not limited thereto:

CY34(1)

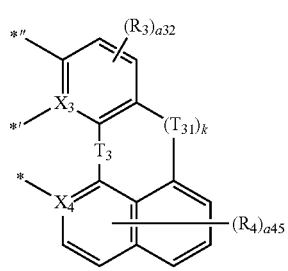

CY34(2)

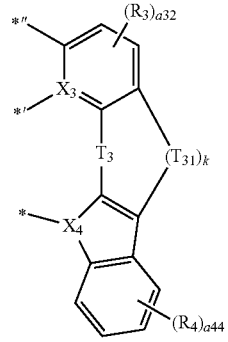

CY34(3)

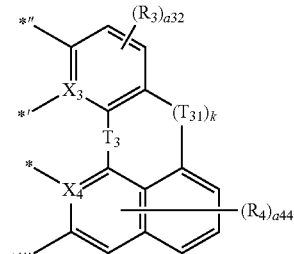

CY34(4)

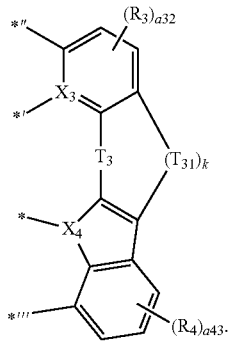

In Formulae CY34(1) to CY34(4),
$X_3$, $X_4$, $T_3$, $R_3$, and $R_4$ are each independently the same as described herein,
$T_{31}$ may be a single bond, O, S, $N(R_{41})$, $C(R_{41})(R_{42})$, or $Si(R_{41})(R_{42})$,
k may be 0, 1, 2, 3, 4, or 5, wherein, when k is 0, $T_{31}$ does not exist, and when k is two or more, two or more groups $T_{31}$ may be different from each other,
$R_{41}$ and $R_{42}$ are each independently the same as described in connection with $R_4$,
a45 may be an integer from 0 to 5,
a44 may be an integer from 0 to 4,
a43 may be an integer from 0 to 3,
a32 may be an integer from 0 to 2,
and *' each indicate a binding site to M in Formula 1,
" indicates a binding site to $T_2$ in Formula 1, and
''' indicates a binding site to $T_4$ in Formula 1.
In one or more embodiments, regarding Formula 1,
i) n may be 0, and $A_1$ may be represented by one selected from Formulae CY1(1) to CY1(24), or ii) n may be 1, and $A_1$ may be represented by one selected from Formulae CY1(101) to CY1(116),
$A_2$ may be represented by one selected from Formulae CZ(1) to CZ(24),
$A_3$ may be represented by one selected from Formulae CY3(1) to CY3(14), and/or i) n may be 0, and $A_4$ may be represented by one selected from Formulae CY4(1) to CY4(13), or ii) n may be 1, and $A_4$ may be represented by one selected from Formulae CY4(101) to CY4(110):
CY1(1)
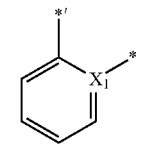
CY1(2)
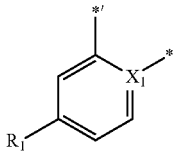
CY1(3)
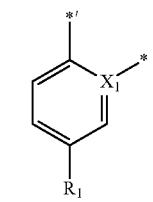
CY1(4)
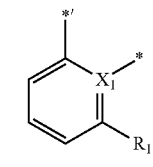
CY1(5)
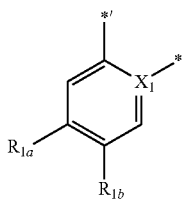
CY1(6)
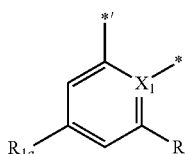
CY1(7)
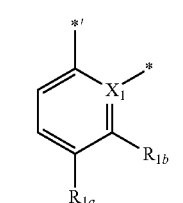
CY1(8)
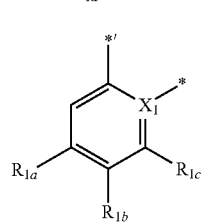
-continued
CY1(9)
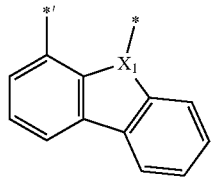
CY1(10)
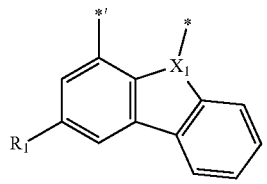
CY1(11)
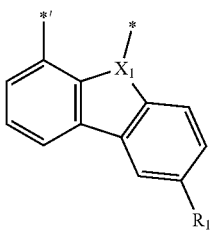
CY1(12)
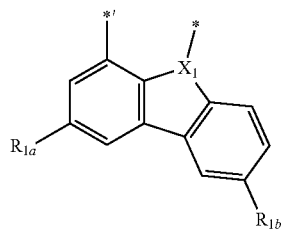
CY1(13)
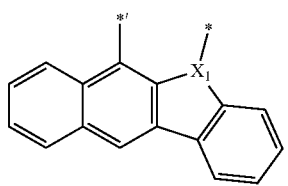
CY1(14)
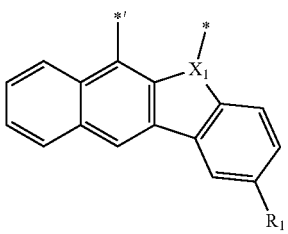
CY1(15)
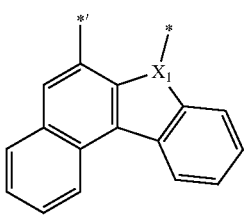

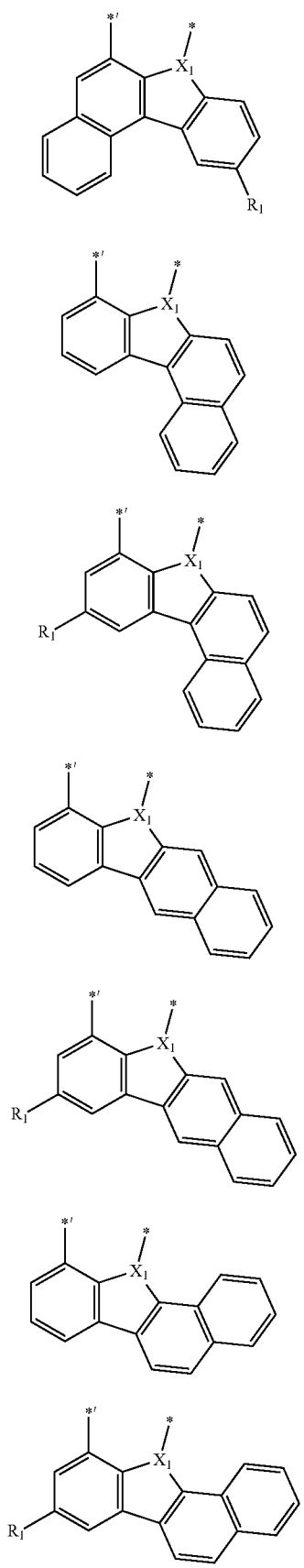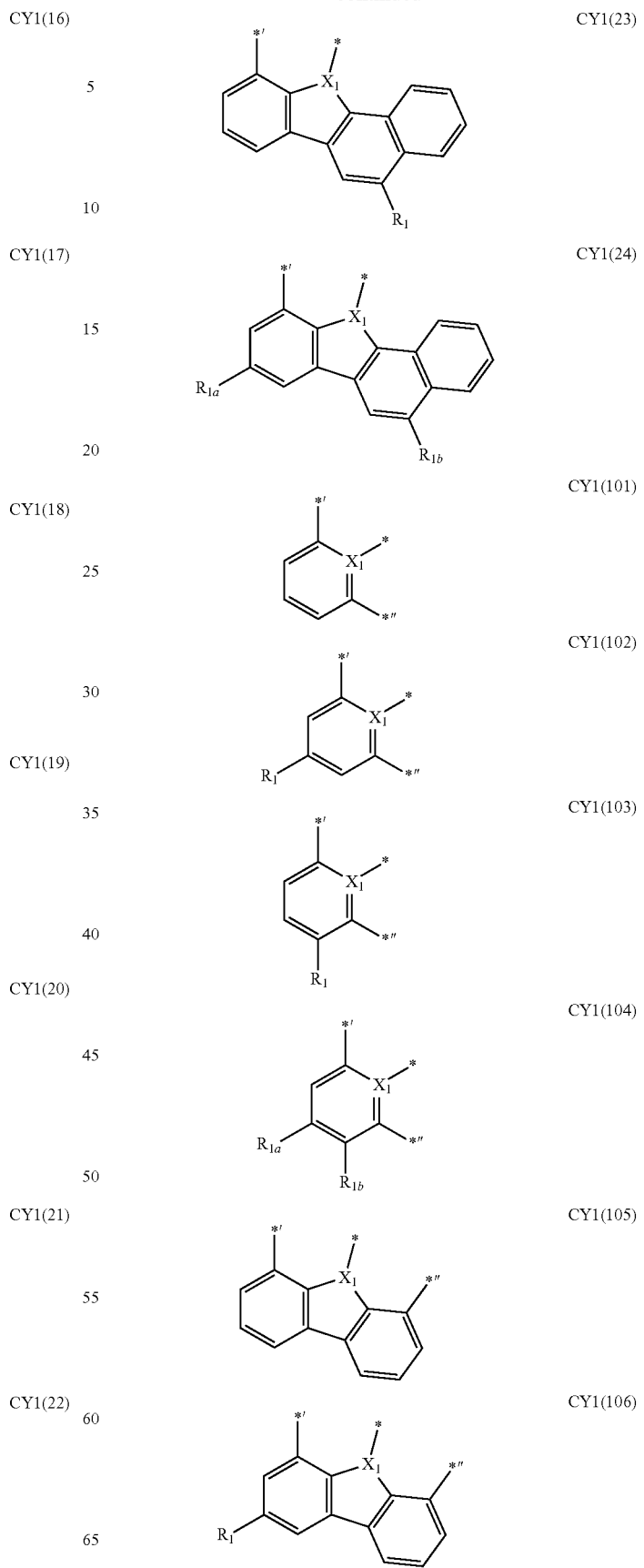

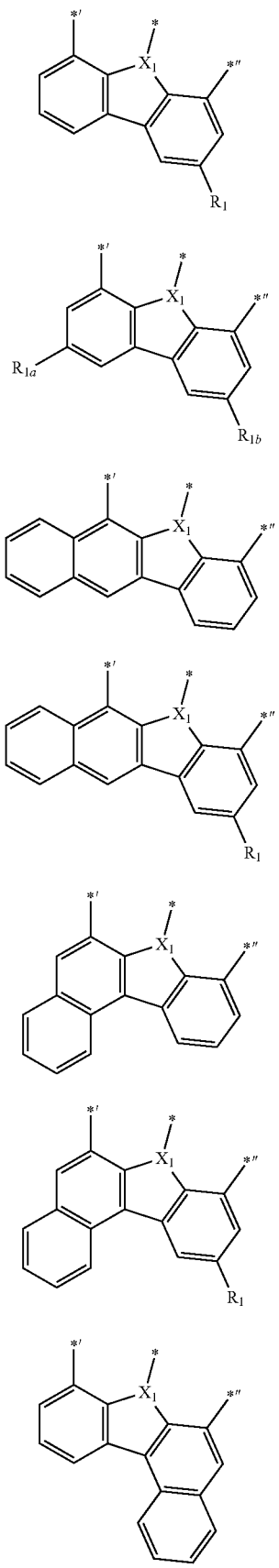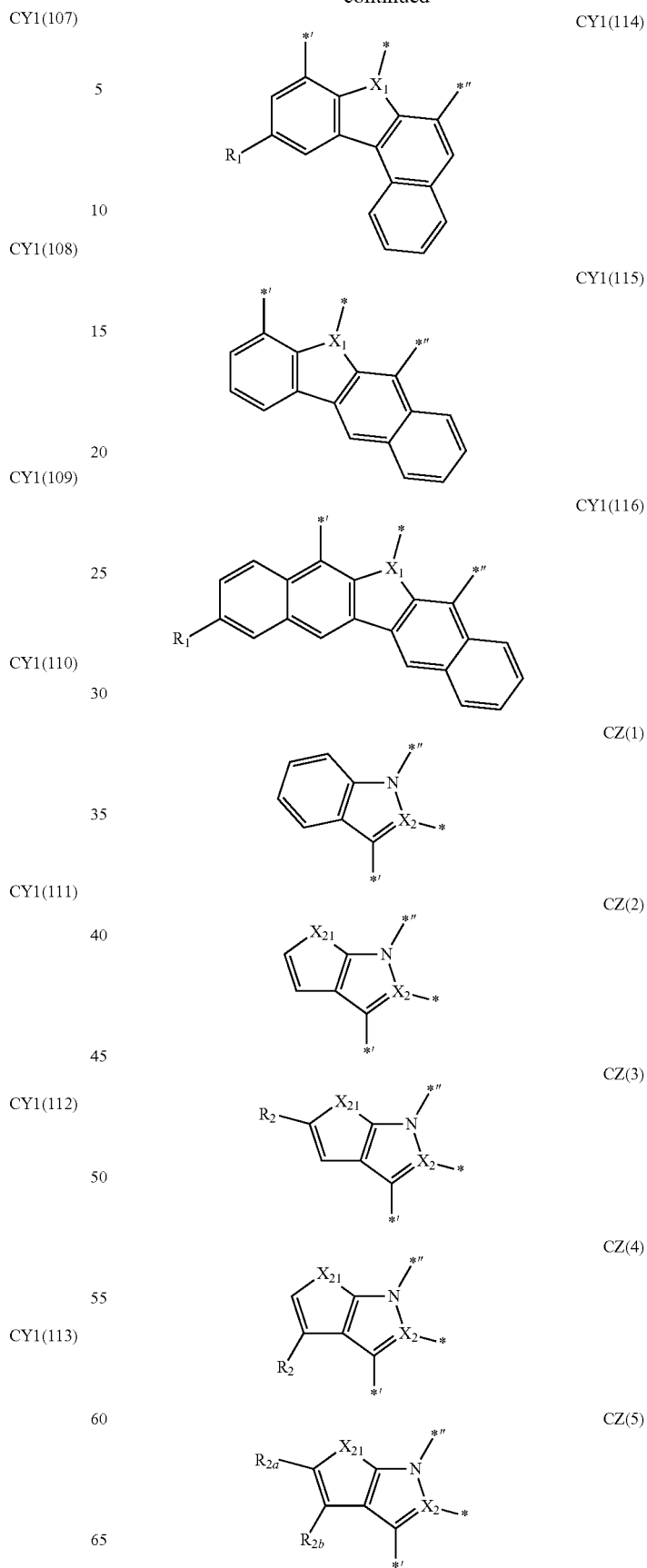

-continued

CZ(6)
CZ(7)
CZ(8)
CZ(9)
CZ(10)
CZ(11)
CZ(12)
CZ(13)

-continued

CZ(14)
CZ(15)
CZ(16)
CZ(17)
CZ(18)
CZ(19)
CZ(20)
CZ(21)
CZ(22)

-continued
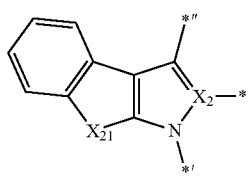 CZ(23)
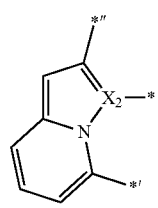 CZ(24)
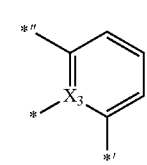 CY3(1)
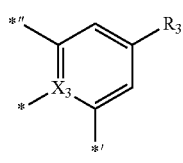 CY3(2)
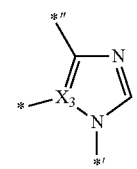 CY3(3)
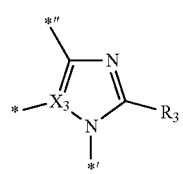 CY3(4)
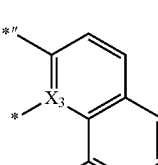 CY3(5)
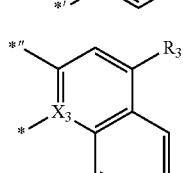 CY3(6)
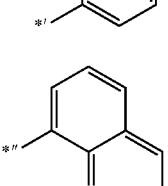 CY3(7)
-continued
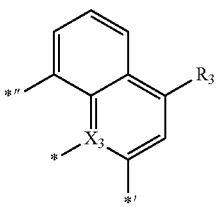 CY3(8)
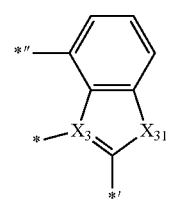 CY3(9)
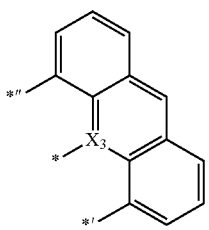 CY3(10)
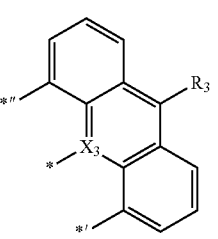 CY3(11)
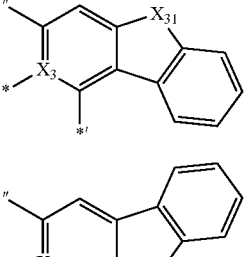 CY3(12)
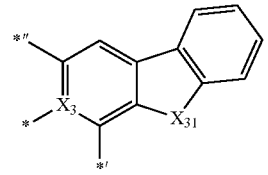 CY3(13)
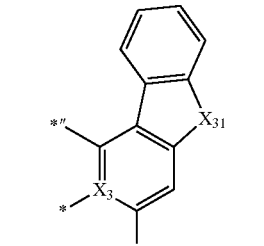 CY3(14)
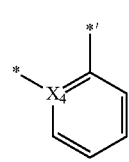 CY4(1)

-continued
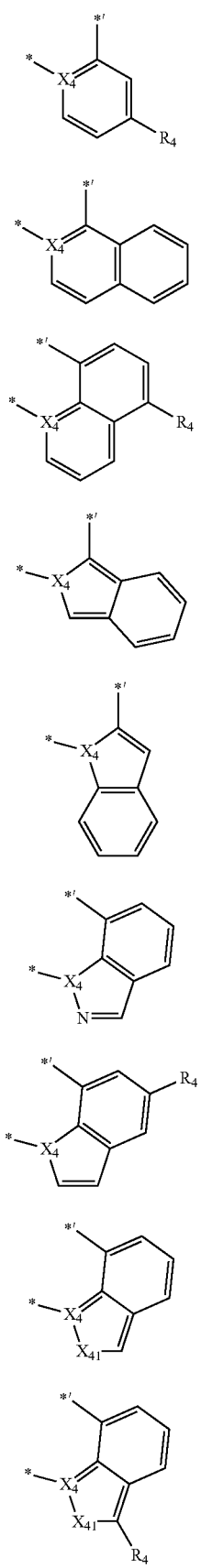
CY4(2)
CY4(3)
CY4(4)
CY4(5)
CY4(6)
CY4(7)
CY4(8)
CY4(9)
CY4(10)
-continued
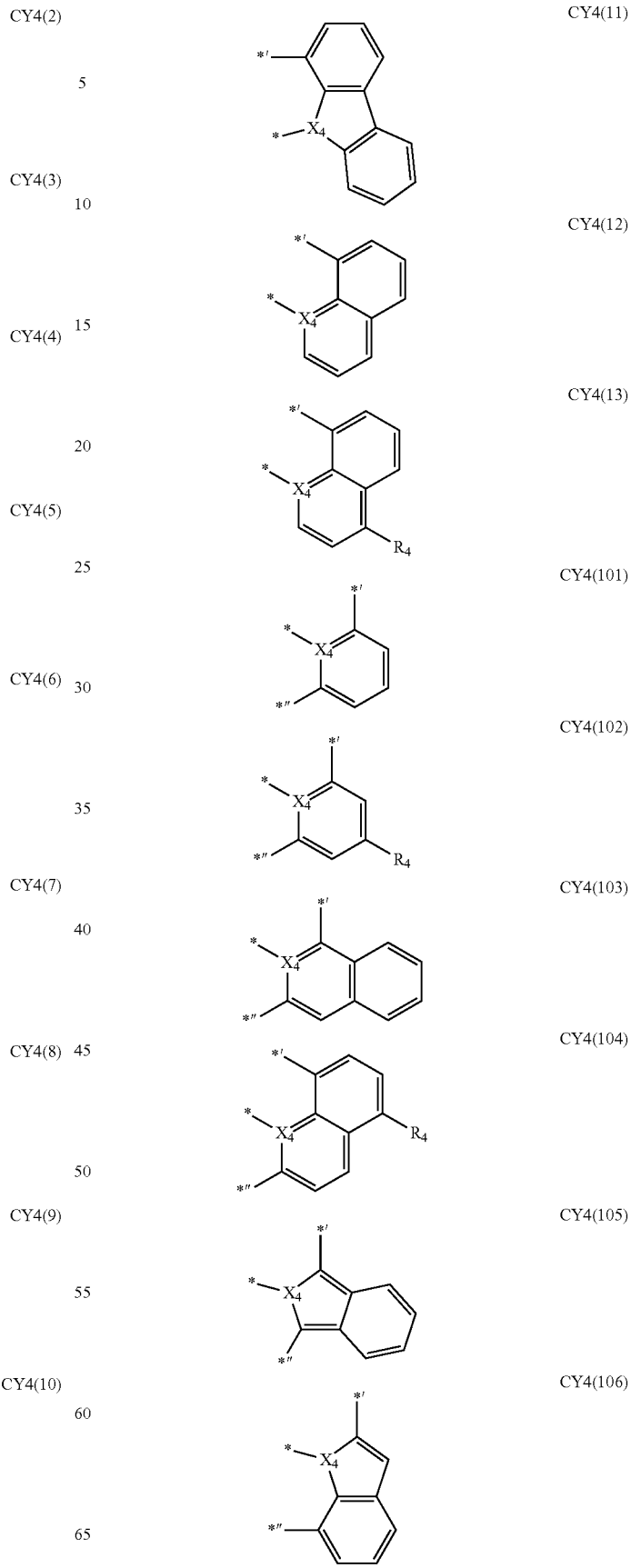
CY4(11)
CY4(12)
CY4(13)
CY4(101)
CY4(102)
CY4(103)
CY4(104)
CY4(105)
CY4(106)

CY4(107)

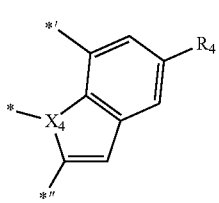

CY4(108)

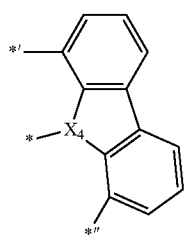

CY4(109)

CY4(110)

In Formulae CY1(1) to CY1(24), CY1(101) to CY1(116), CZ(1) to CZ(24), CY3(1) to CY3(14), CY4(1) to CY4(13), and CY4(101) to CY4(110), $X_1$, $X_2$, $X_3$, $X_4$, $R_1$, $R_2$, $R_3$, and $R_4$ are each independently the same as described herein, $X_{21}$ may be O, S, $N(R_{21})$, $C(R_{21})(R_{22})$, or $Si(R_{21})(R_{22})$, $X_{31}$ may be O, S, $N(R_{31})$, $C(R_{31})(R_{32})$, or $Si(R_{31})(R_{32})$, $X_{41}$ may be O, S, $N(R_{41})$, $C(R_{41})(R_{42})$, or $Si(R_{41})(R_{42})$, $R_{1a}$, $R_{1b}$, and $R_{1c}$ are each independently the same as described in connection with $R_1$, $R_{2a}$, $R_{2b}$, $R_{21}$, and $R_{22}$ are each independently the same as described in connection with $R_2$, $R_{31}$ and $R_{32}$ are each independently the same as described in connection with $R_3$, $R_{41}$ and $R_{42}$ are each independently the same as described in connection with $R_4$, and , \*', and \*" each indicate a binding site to a neighboring atom.

For example, the organometallic compound represented by Formula 1 may one of Compounds 1 to 88, but embodiments of the present disclosure are not limited thereto:

1

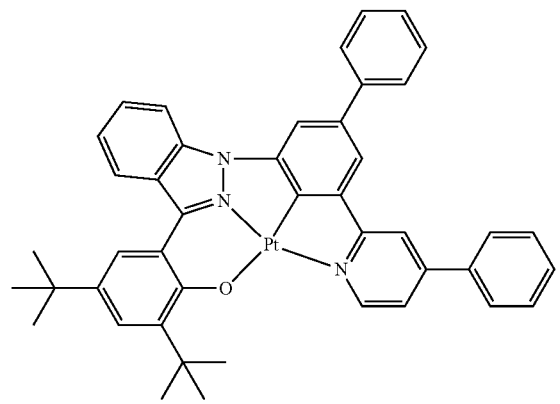

2

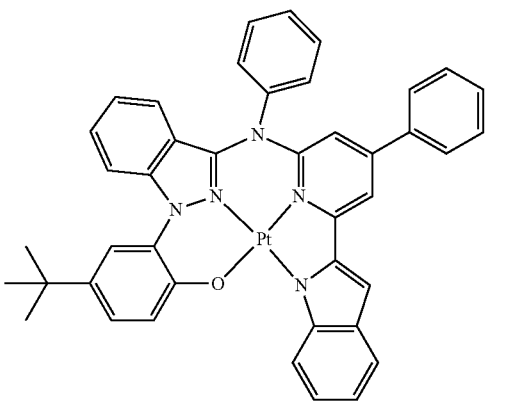

3

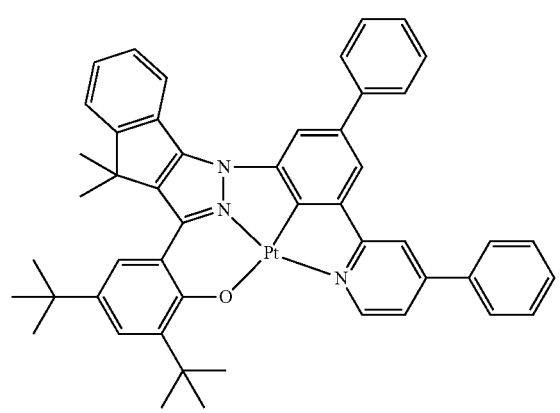

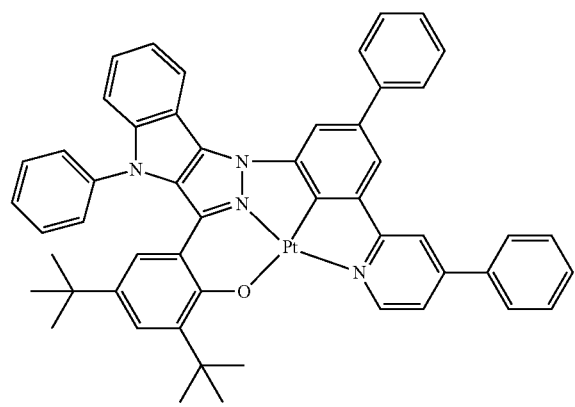
4
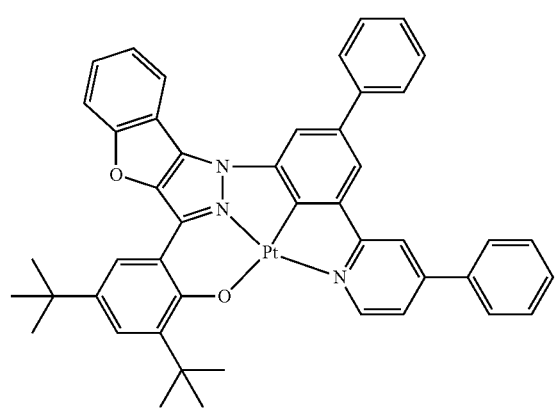
5
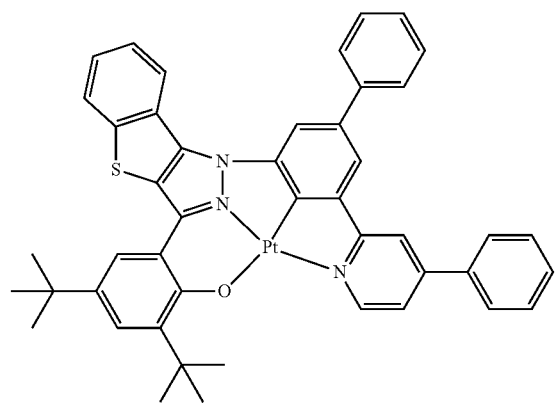
6
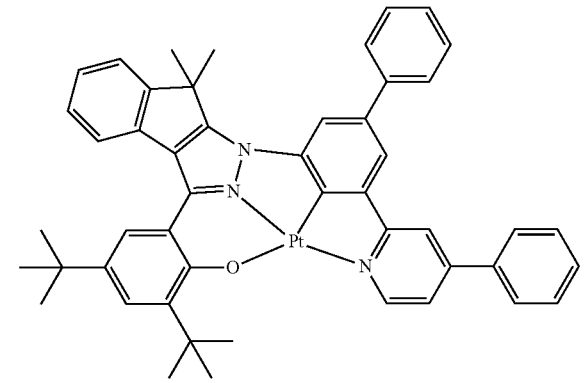
7
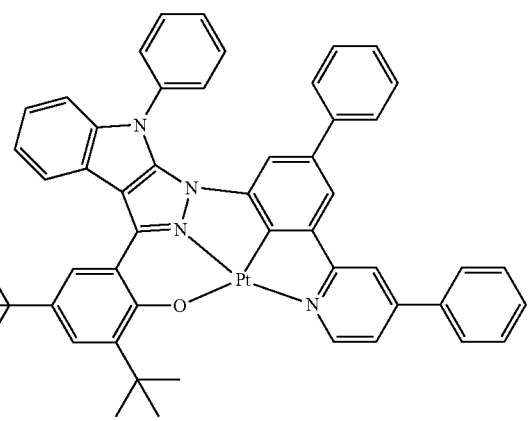
8
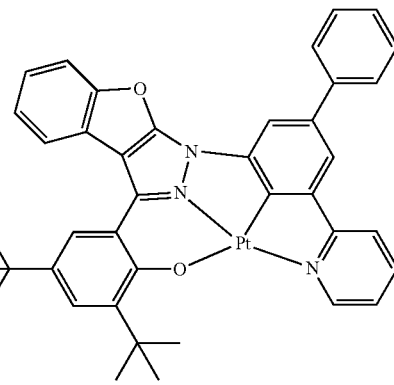
9
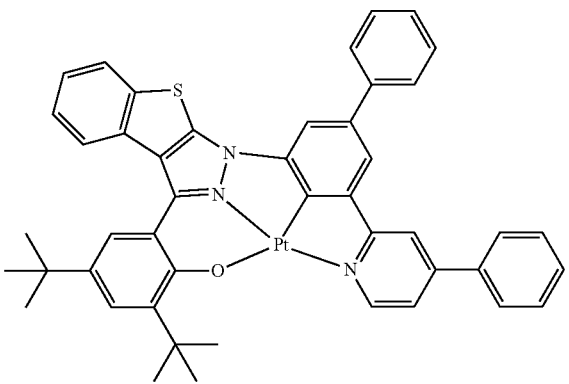
10

-continued
11
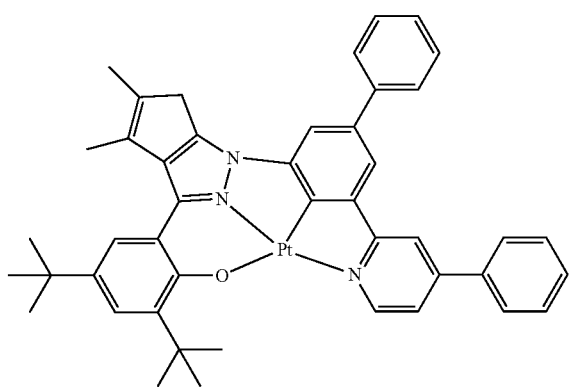
12
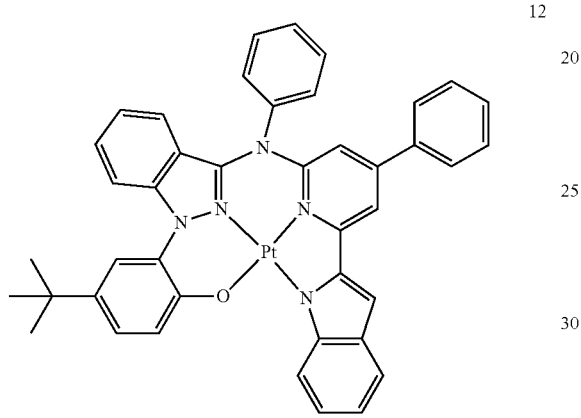
13
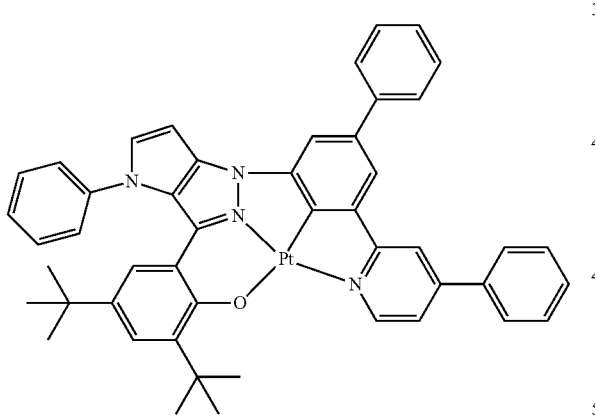
14
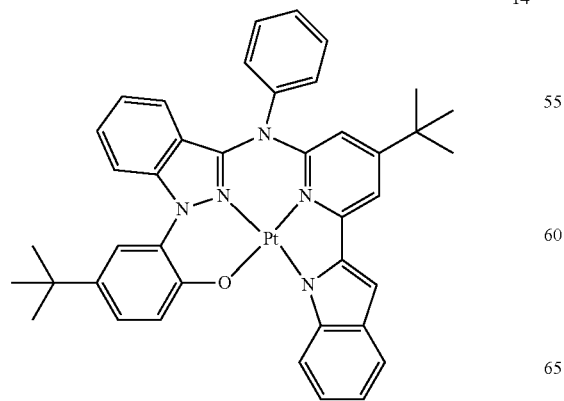
-continued
15
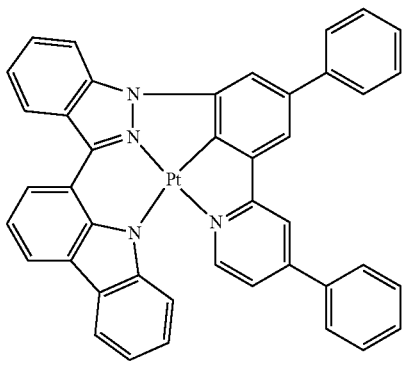
16
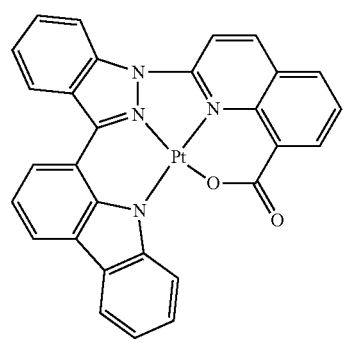
17
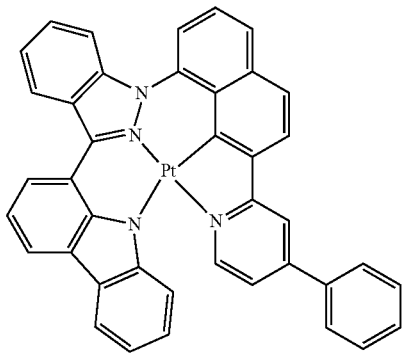
18
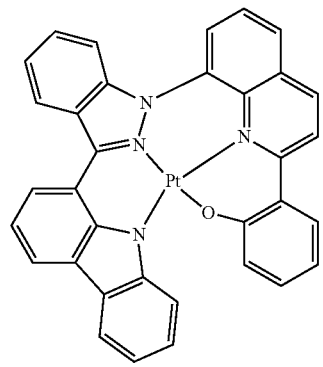

19
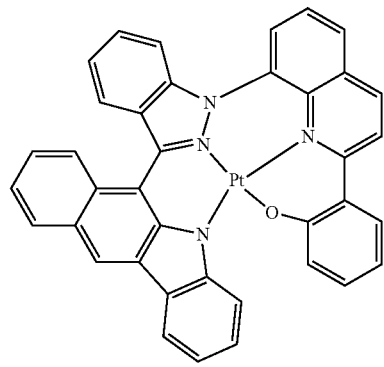
20
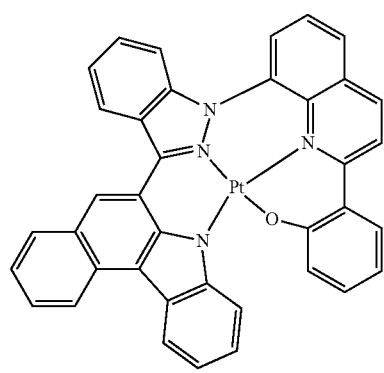
21
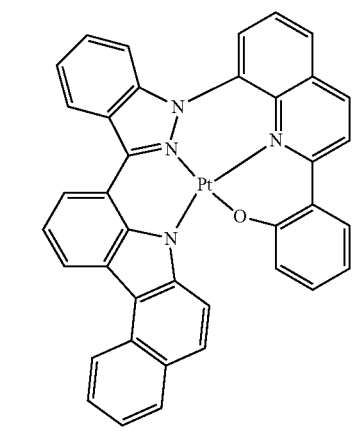
22
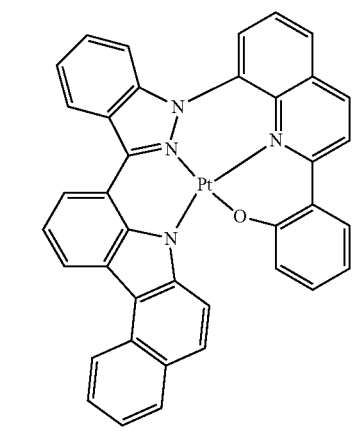
23
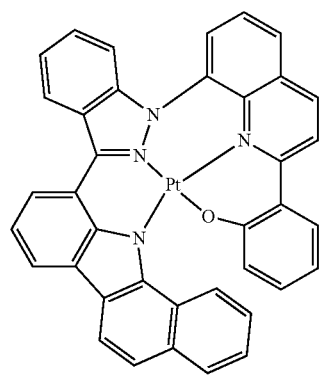
24
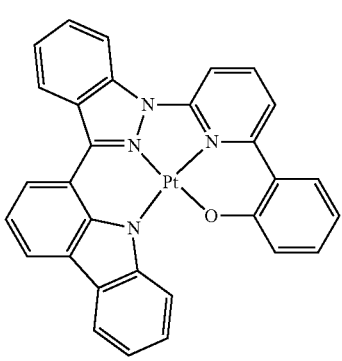
25
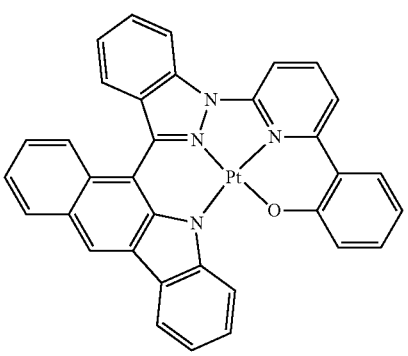
26
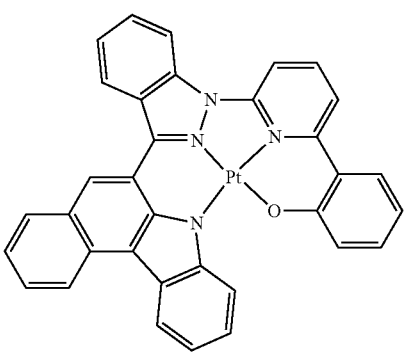

27
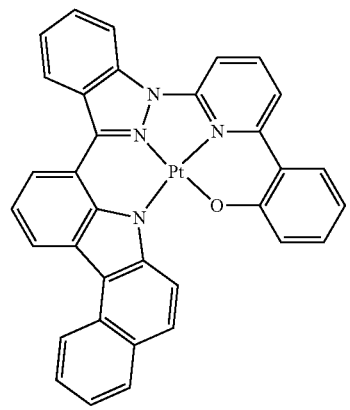
28
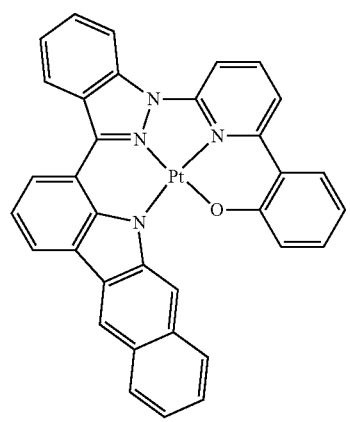
29
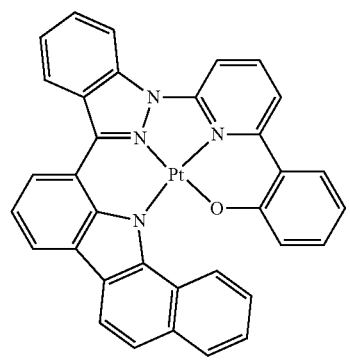
30
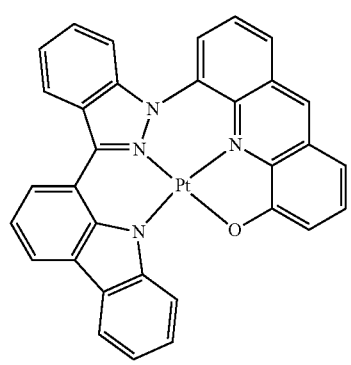
31
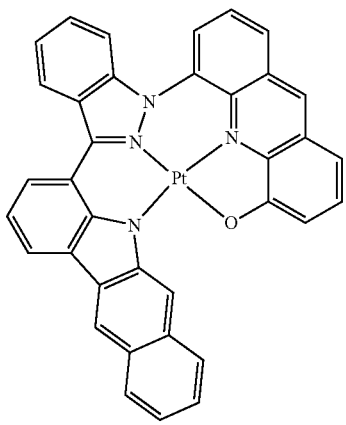
32
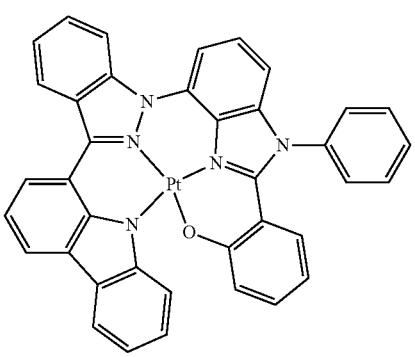
33
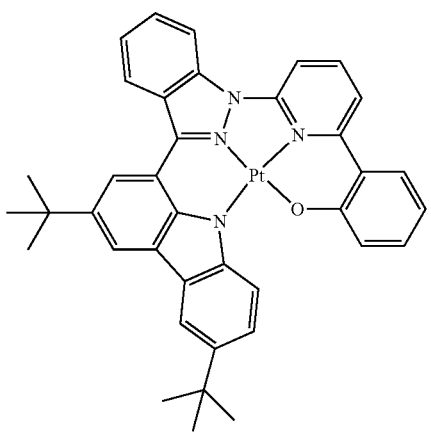
34
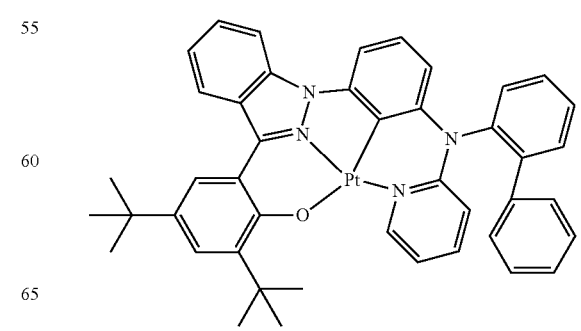

35
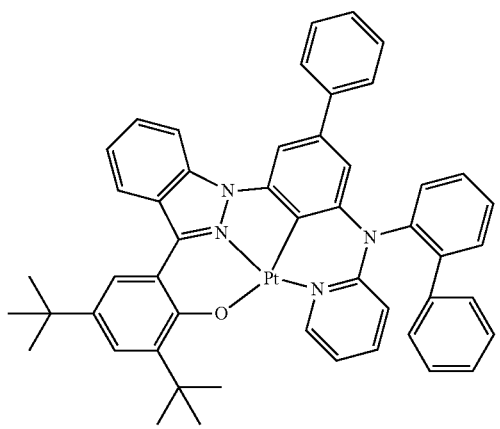
36
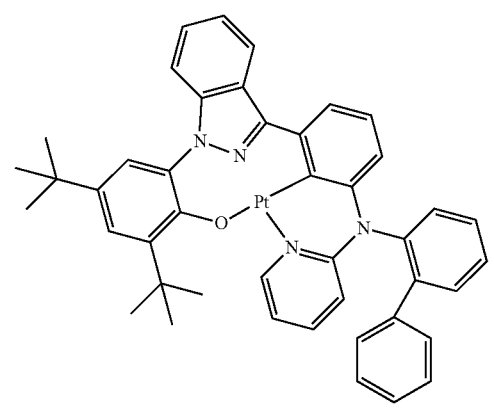
37
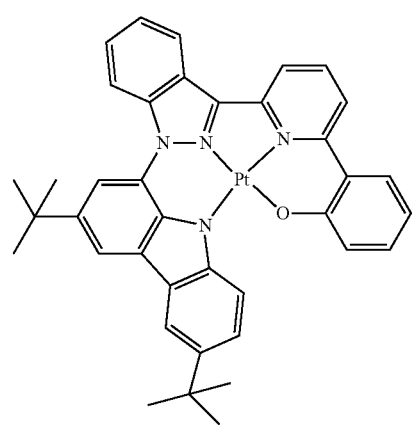
38
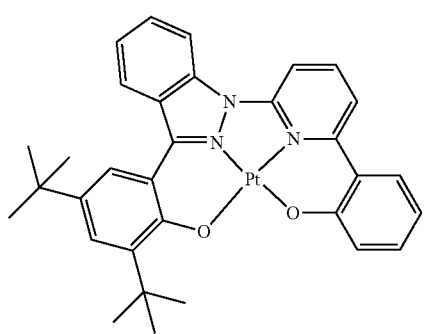
39
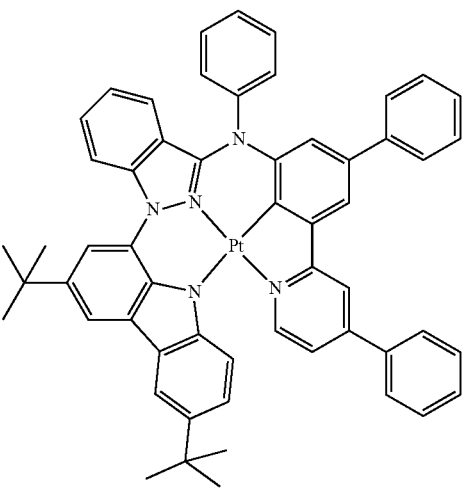
40
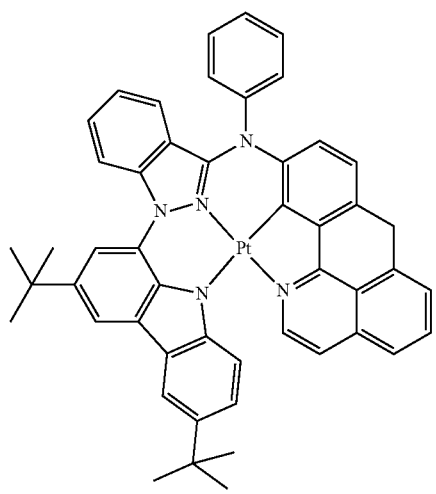
41
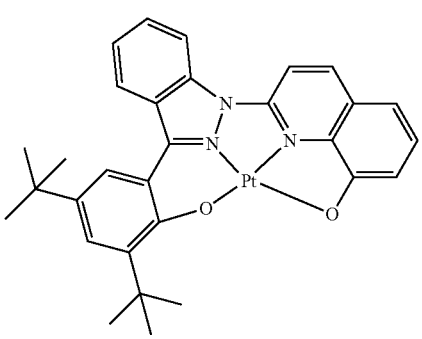
42
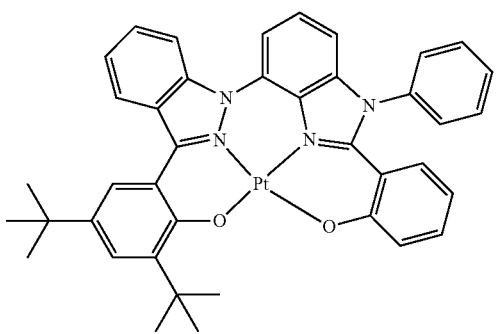

43
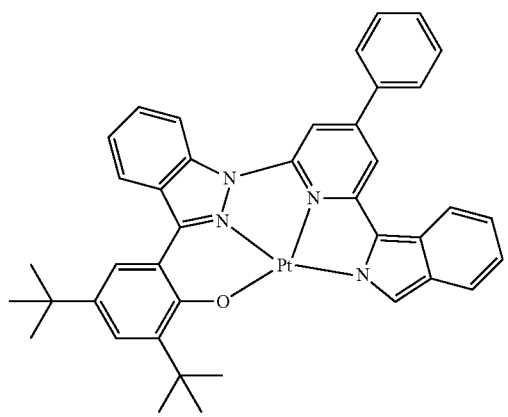
44
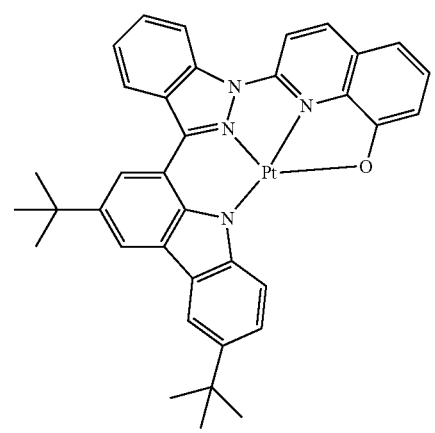
45
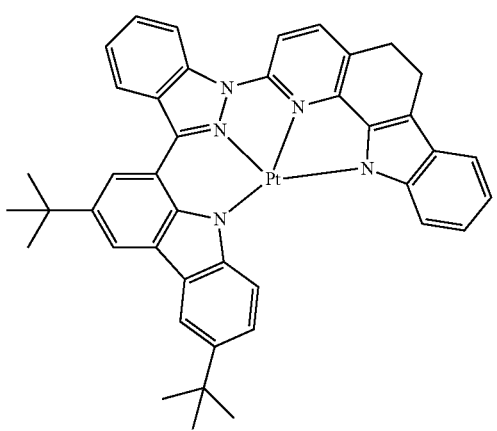
46
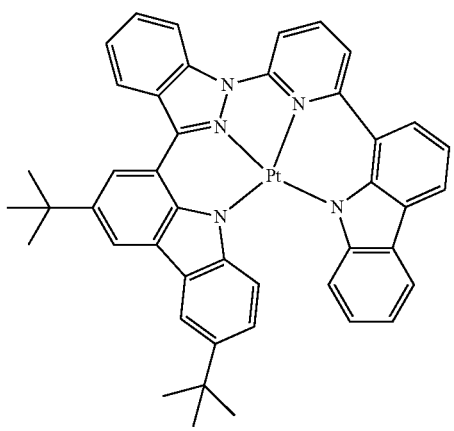
47
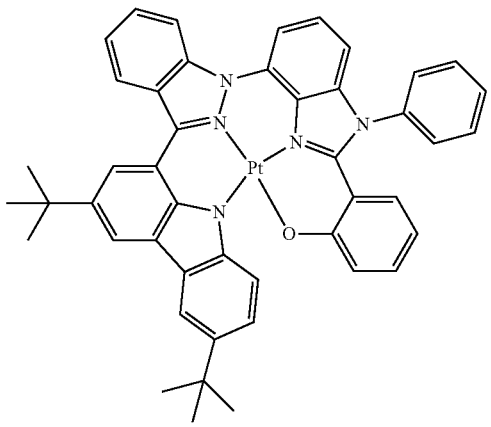
48
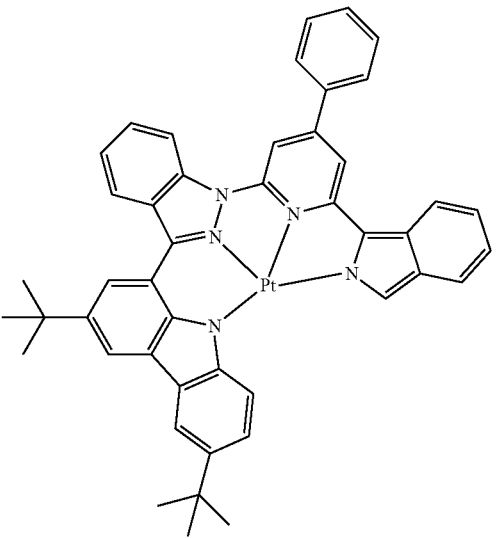

49
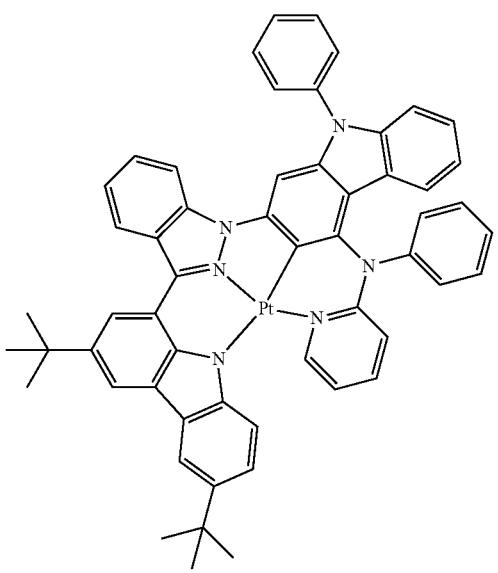
50
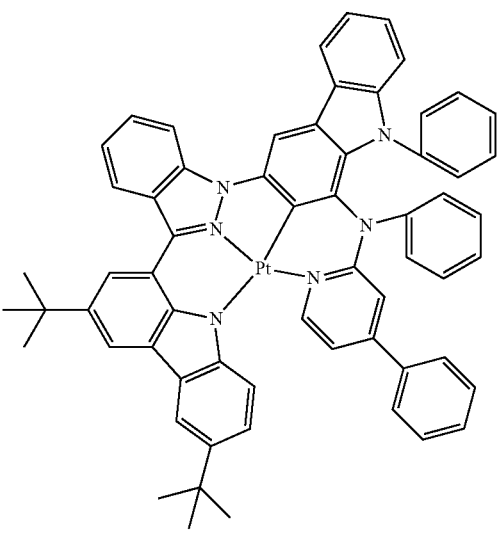
51
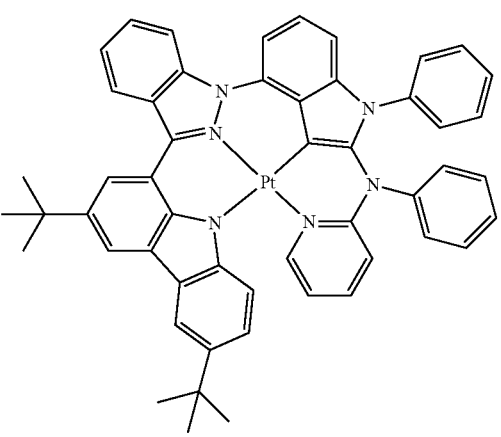
52
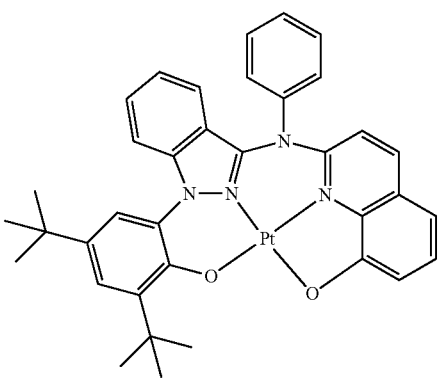
53
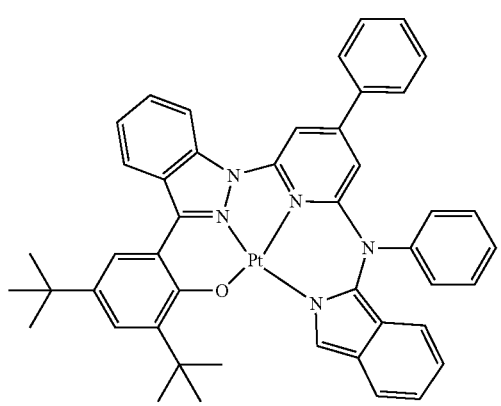
54
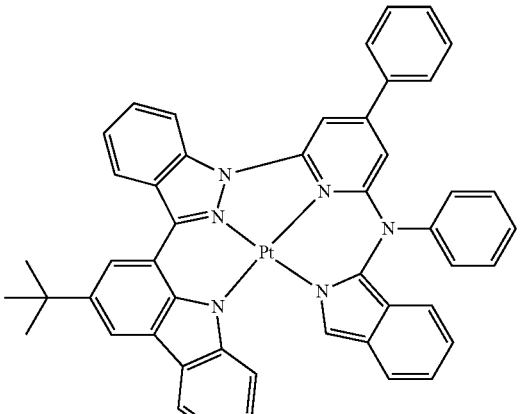
55
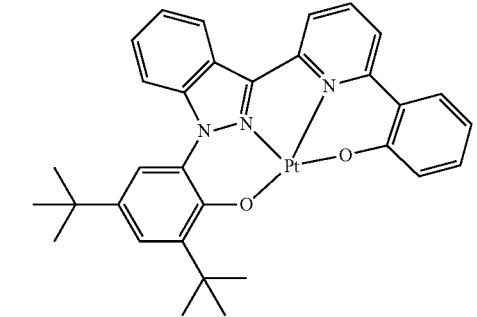

56
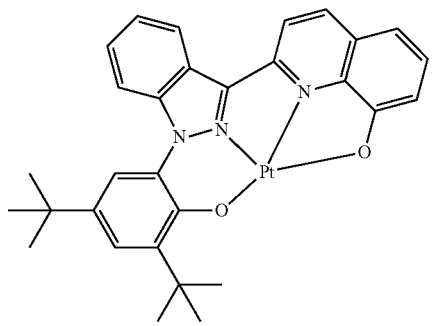
57
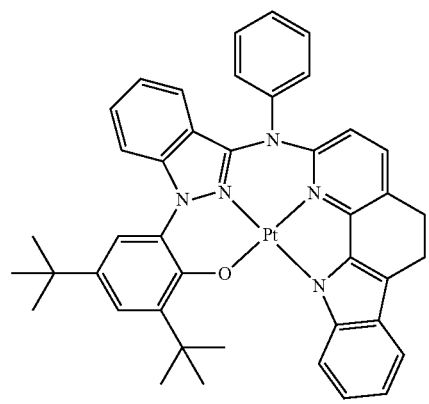
58
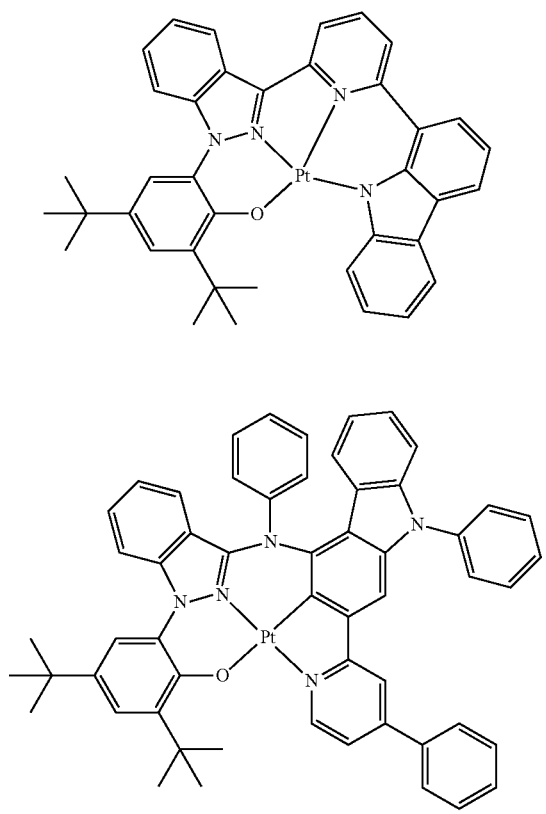
59
60
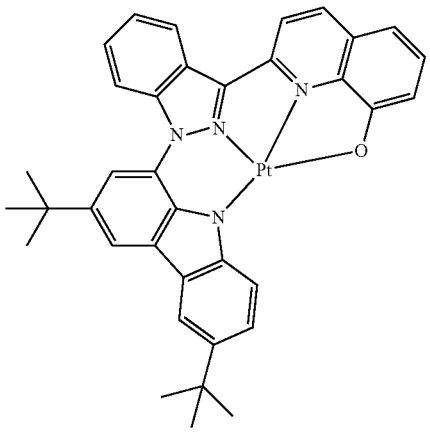
61
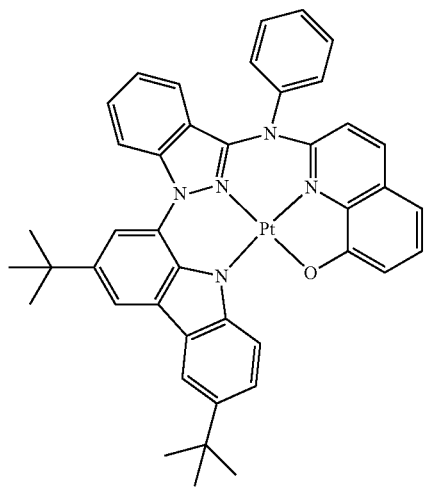
62
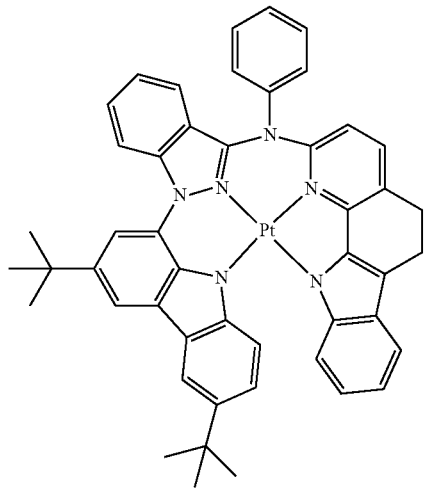

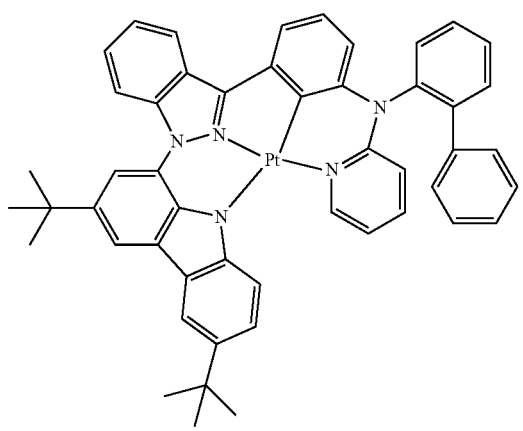
63
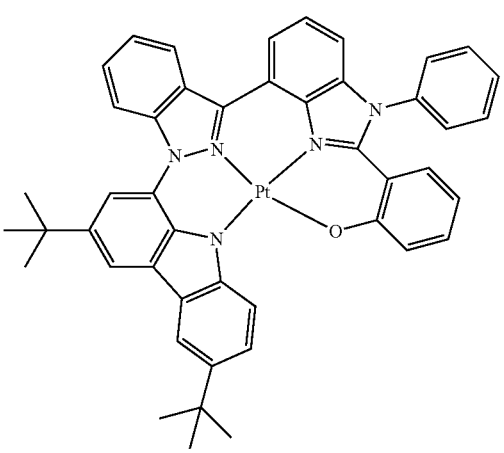
66
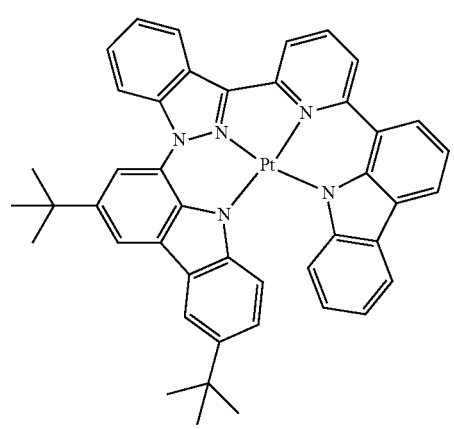
64
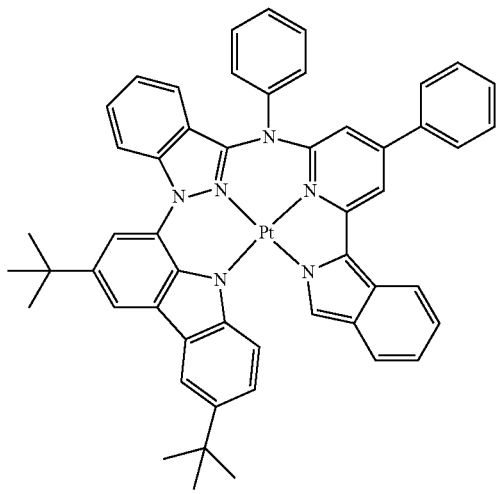
67
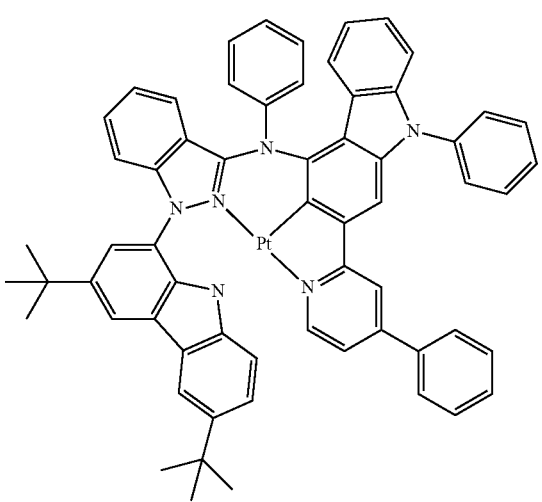
65
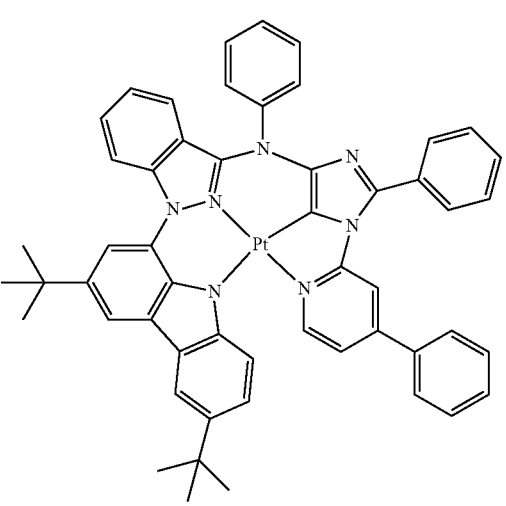
68

91
69
70
71
72
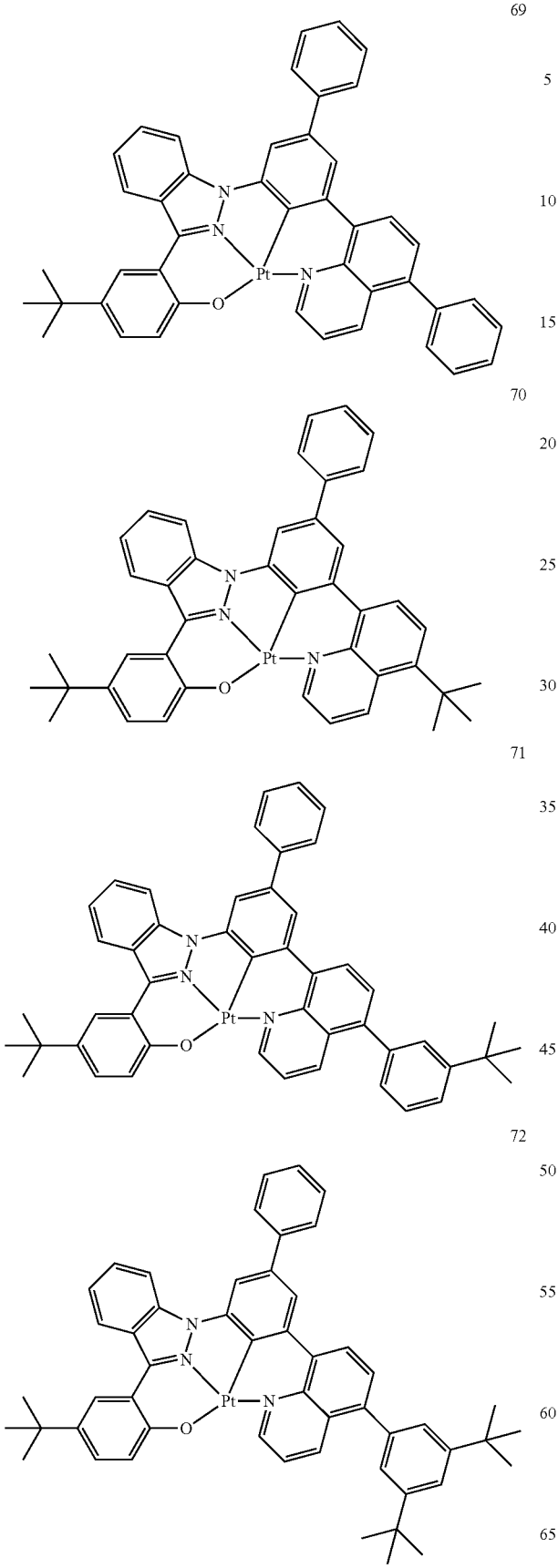
92
73
74
75
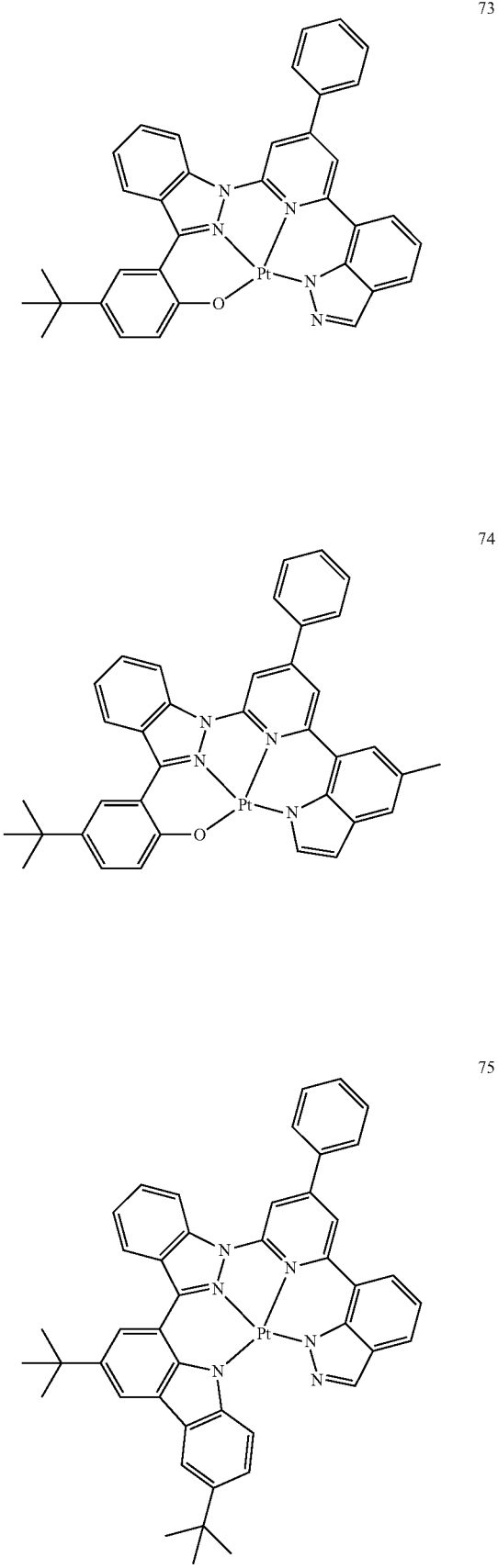

76
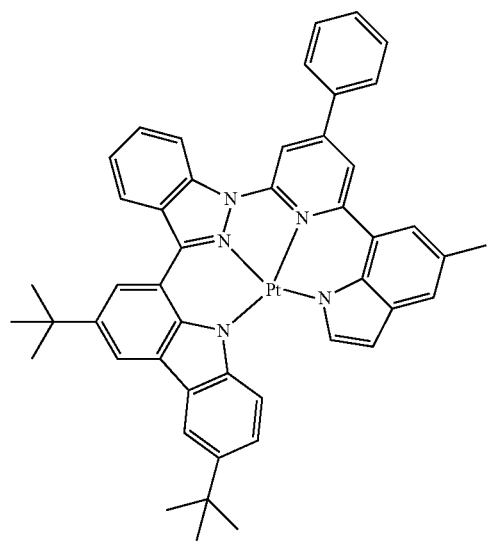
77
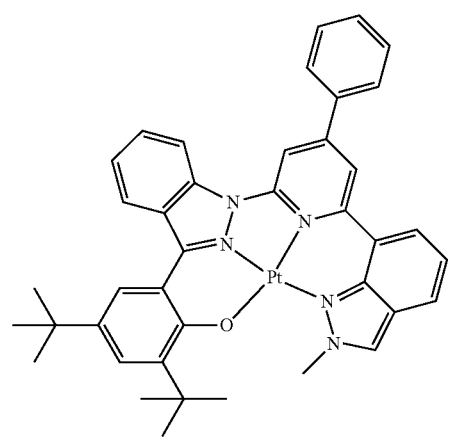
78
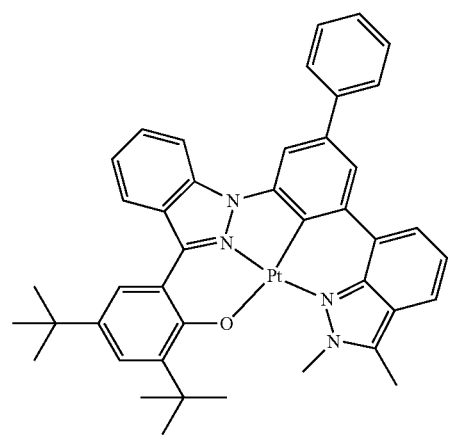
79
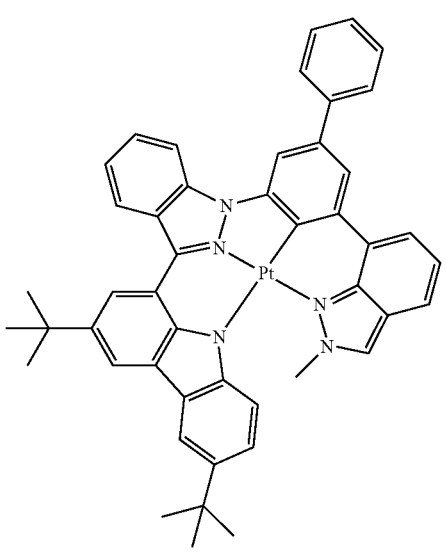
80
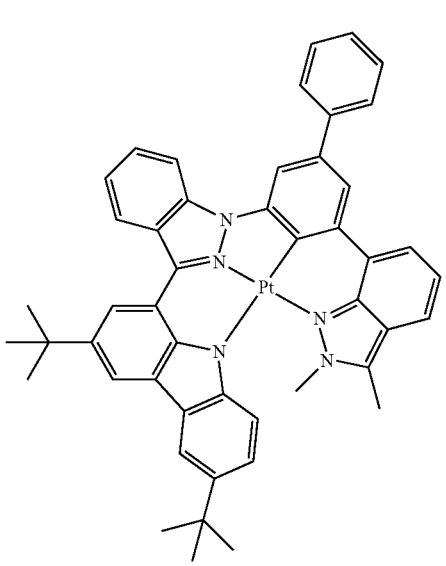
81
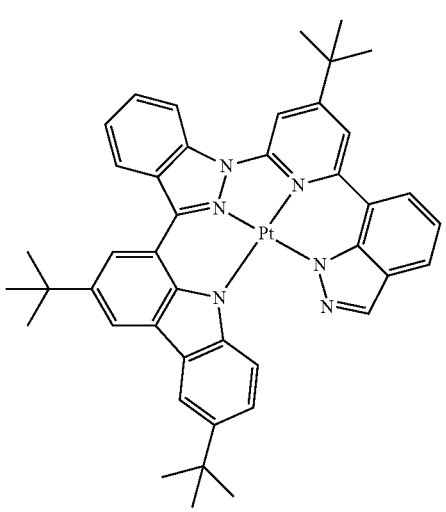

82
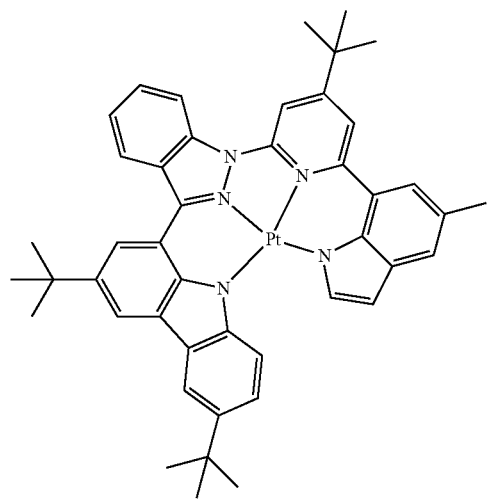
83
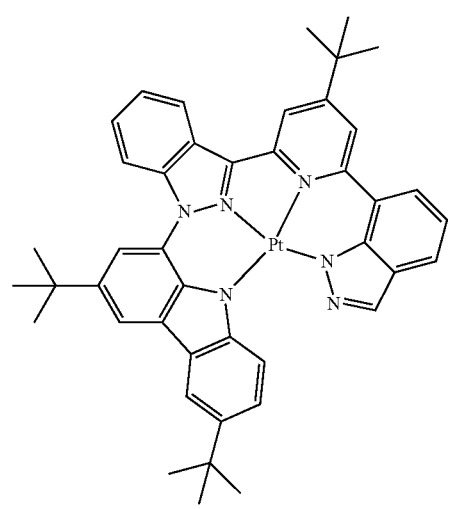
84
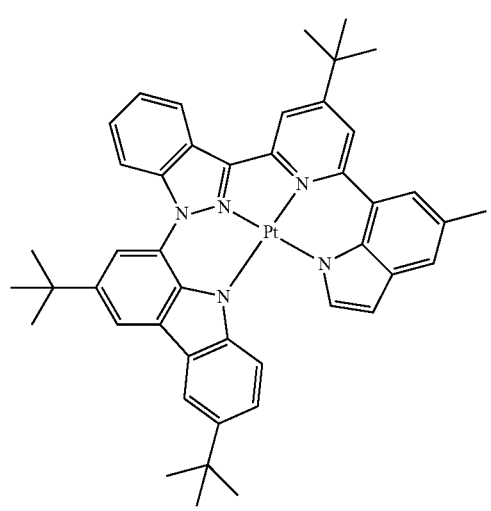
85
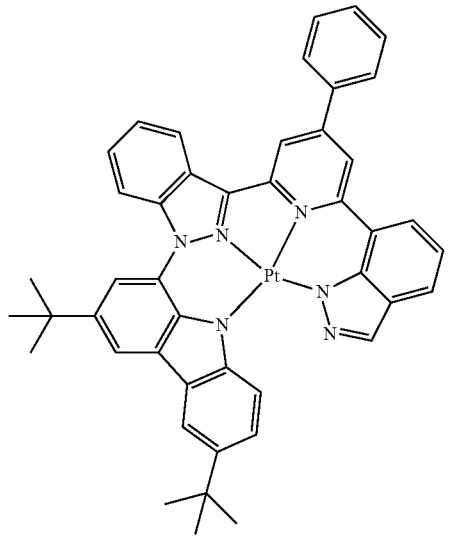
86
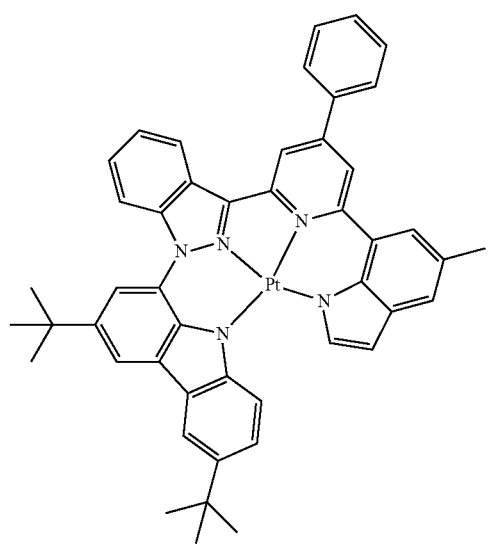
87
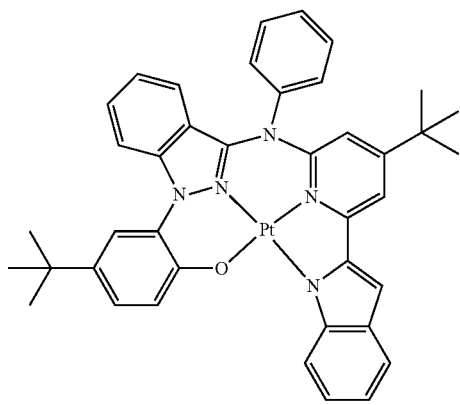

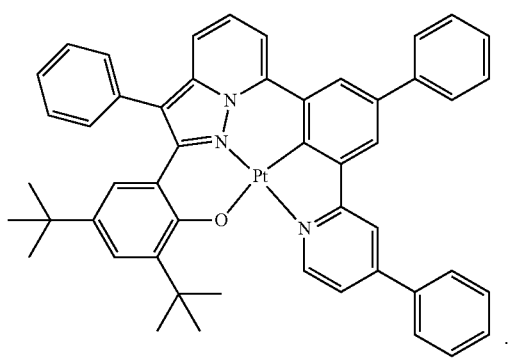

A₂ in Formula 1 is a ring represented by one selected from Formulae A2-1 to A2-3. In this regard, the planarity of the organometallic compound represented by Formula 1 increases, and accordingly, an electronic device including the organometallic compound, for example, an organic light-emitting device, may have increased lifespan and/or efficiency.

For example, highest occupied molecular orbital (HOMO), lowest unoccupied molecular orbital (LUMO), energy bandgap ($E_g$), and singlet ($S_1$) and triplet ($T_1$) energy levels of some Compounds of Compounds and Compounds A and B were evaluated by a DFT method of Gaussian program (structurally optimized at a level of B3LYP, 6-31G (d,p)), and results thereof are shown in Table 1.

TABLE 1

| Compound No. | HOMO (eV) | LUMO (eV) | S₁ energy level (eV) | T₁ energy level (eV) |
|---|---|---|---|---|
| 2 | −4.311 | −2.039 | 1.781 | 1.670 |
| 3 | −4.585 | −1.995 | 2.170 | 2.017 |
| 4 | −4.549 | −1.984 | 2.142 | 2.006 |
| 5 | −4.615 | −2.058 | 2.143 | 1.989 |
| 6 | −4.639 | −2.060 | 2.163 | 2.006 |
| 7 | −4.584 | −2.040 | 2.122 | 1.987 |
| 8 | −4.531 | −1.957 | 2.156 | 2.011 |
| 9 | −4.675 | −2.057 | 2.201 | 2.049 |
| 10 | −4.669 | −2.074 | 2.173 | 2.033 |
| 11 | −4.510 | −1.994 | 2.094 | 1.963 |
| 12 | −4.581 | −1.809 | 2.269 | 1.801 |
| 13 | −4.525 | −1.944 | 2.159 | 2.021 |
| 14 | −4.296 | −1.911 | 1.906 | 1.822 |
| 15 | −4.631 | −2.062 | 2.134 | 1.952 |
| 16 | −4.918 | −2.657 | 1.935 | 1.492 |
| 17 | −4.532 | −2.083 | 2.005 | 1.697 |
| 18 | −4.567 | −2.436 | 1.681 | 1.506 |
| 19 | −4.499 | −2.402 | 1.657 | 1.448 |
| 20 | −4.532 | −2.508 | 1.591 | 1.487 |
| 21 | −4.638 | −2.489 | 1.720 | 1.559 |
| 22 | −4.352 | −2.456 | 1.484 | 1.342 |
| 23 | −4.515 | −2.465 | 1.622 | 1.501 |
| 24 | −4.732 | −2.099 | 2.170 | 1.775 |
| 25 | −4.683 | −2.096 | 2.126 | 1.636 |
| 26 | −4.666 | −2.258 | 1.928 | 1.666 |
| 27 | −4.779 | −2.165 | 2.162 | 1.786 |
| 28 | −4.508 | −2.120 | 1.977 | 1.622 |
| 29 | −4.641 | −2.139 | 2.047 | 1.711 |
| 30 | −4.637 | −2.684 | 1.660 | 1.046 |
| 31 | −4.443 | −2.698 | 1.455 | 0.984 |
| 32 | −4.429 | −1.804 | 2.102 | 1.790 |
| 33 | −4.606 | −2.073 | 2.084 | 1.698 |
| 34 | −4.558 | −1.456 | 2.585 | 2.184 |
| 35 | −4.576 | −1.485 | 2.573 | 2.178 |
| 36 | −4.563 | −1.558 | 2.490 | 2.135 |
| 37 | −4.631 | −2.321 | 1.877 | 1.529 |
| 38 | −4.864 | −1.992 | 2.357 | 1.936 |
| 39 | −4.258 | −1.891 | 1.879 | 1.793 |
| 40 | −4.217 | −1.975 | 1.779 | 1.675 |
| 41 | −5.060 | −2.213 | 2.289 | 1.771 |
| 42 | −4.615 | −1.731 | 2.319 | 1.940 |
| 43 | −4.709 | −1.976 | 2.230 | 1.827 |
| 44 | −4.740 | −2.222 | 2.123 | 1.641 |
| 45 | −4.581 | −2.040 | 2.070 | 1.726 |
| 46 | −4.524 | −2.088 | 1.909 | 1.623 |
| 47 | −4.325 | −1.787 | 2.012 | 1.684 |
| 48 | −4.653 | −1.595 | 2.097 | 1.766 |
| 49 | −4.438 | −1.822 | 2.089 | 1.896 |
| 50 | −4.397 | −1.816 | 2.093 | 1.944 |
| 51 | −4.139 | −1.505 | 2.044 | 1.825 |
| 52 | −4.696 | −1.797 | 2.325 | 1.948 |
| 53 | −3.864 | −1.970 | 1.411 | 1.234 |
| 54 | −4.027 | −2.109 | 1.429 | 1.333 |
| 55 | −4.961 | −2.250 | 2.179 | 1.826 |
| 56 | −5.110 | −2.495 | 1.940 | 1.518 |
| 57 | −4.569 | −1.567 | 2.482 | 1.871 |
| 58 | −4.756 | −2.288 | 1.934 | 1.700 |
| 59 | −4.436 | −1.947 | 2.003 | 1.908 |
| 60 | −4.742 | −2.481 | 1.884 | 1.416 |
| 61 | −4.303 | −1.865 | 1.899 | 1.731 |
| 62 | −4.408 | −1.581 | 2.280 | 1.829 |
| 63 | −4.305 | −1.632 | 2.173 | 1.918 |
| 64 | −4.551 | −2.312 | 1.707 | 1.471 |
| 65 | −4.404 | −1.974 | 1.955 | 1.879 |
| 66 | −4.374 | −2.021 | 1.845 | 1.614 |
| 67 | −4.507 | −1.620 | 2.394 | 1.853 |
| 68 | −4.131 | −2.046 | 1.595 | 1.503 |
| 69 | −4.688 | −2.176 | 2.053 | 1.833 |
| 70 | −4.674 | −2.123 | 2.088 | 1.855 |
| 71 | −4.676 | −2.158 | 2.055 | 1.834 |
| 72 | −4.662 | −2.127 | 2.072 | 1.846 |
| 73 | −4.774 | −2.116 | 2.151 | 1.821 |
| 74 | −4.593 | −1.995 | 2.112 | 1.757 |
| 75 | −4.479 | −2.185 | 1.831 | 1.565 |
| 76 | −4.487 | −2.086 | 1.899 | 1.620 |
| 77 | −4.714 | −1.733 | 2.535 | 2.094 |
| 78 | −4.679 | −1.651 | 2.584 | 2.095 |
| 79 | −4.497 | −1.804 | 2.221 | 1.904 |
| 80 | −4.460 | −1.698 | 2.294 | 1.937 |
| 81 | −4.455 | −2.004 | 1.959 | 1.631 |
| 82 | −4.465 | −1.974 | 1.981 | 1.676 |
| 83 | −4.454 | −2.209 | 1.786 | 1.477 |
| 84 | −4.475 | −2.168 | 1.782 | 1.545 |
| 85 | −4.480 | −2.327 | 1.717 | 1.410 |
| 86 | −4.524 | −2.257 | 1.770 | 1.519 |
| 87 | −4.557 | −1.527 | 2.514 | 1.884 |
| 88 | −4.485 | −2.007 | 2.007 | 1.910 |
| A | −5.110 | −1.161 | 3.348 | 2.966 |
| B | −5.188 | −1.8002 | 2.726 | 2.465 |

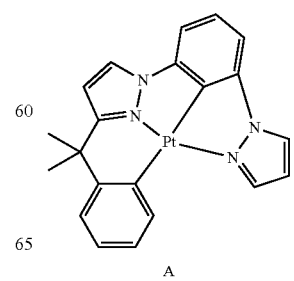

A

TABLE 1-continued

| Compound No. | HOMO (eV) | LUMO (eV) | S₁ energy level (eV) | T₁ energy level (eV) |
|---|---|---|---|---|

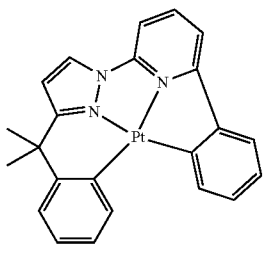

B

From Table 1, it is confirmed that the organometallic compound represented by Formula 1 has such electric characteristics that are suitable for use in an electric device, for example, for use as a dopant for an organic light-emitting device.

Synthesis methods of the organometallic compound represented by Formula 1 may be understood by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes: a first electrode; a second electrode; and an organic layer that is disposed between the first electrode and the second electrode and includes an organic layer including an emission layer and at least one of the organometallic compound represented by Formula 1.

The organic light-emitting device may have, due to the inclusion of an organic layer including the organometallic compound represented by Formula 1, a low driving voltage, high efficiency, high power, high quantum efficiency, a long lifespan, a low roll-off ratio, and excellent color purity.

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression "(an organic layer) includes at least one of organometallic compounds" as used herein may include an embodiment in which "(an organic layer) includes identical organometallic compounds represented by Formula 1" and an embodiment in which "(an organic layer) includes two or more different organometallic compounds represented by Formula 1."

For example, the organic layer may include, as the organometallic compound, only Compound 1. In this regard, Compound 1 may be included in an emission layer of the organic light-emitting device. In one or more embodiments, the organic layer may include, as the organometallic compound, Compound 1 and Compound 2. In this regard, Compound 1 and Compound 2 may be included in an identical layer (for example, Compound 1 and Compound 2 may both be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

In an embodiment, in the organic light-emitting device, the first electrode is an anode, and the second electrode is a cathode, and the organic layer further includes a hole transport region disposed between the first electrode and the emission layer and an electron transport region disposed between the emission layer and the second electrode, wherein the hole transport region includes a hole injection layer, a hole transport layer, an electron blocking layer, or any combination thereof, and wherein the electron transport region includes a hole blocking layer, an electron transport layer, an electron injection layer, or any combination thereof.

The term "organic layer" as used herein refers to a single layer and/or a plurality of layers disposed between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, 8-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

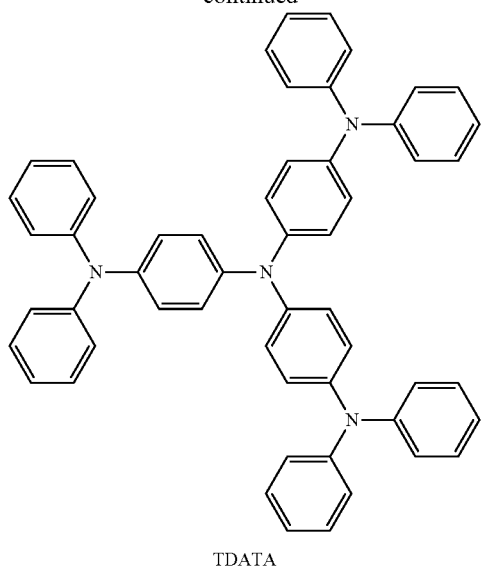

TDATA

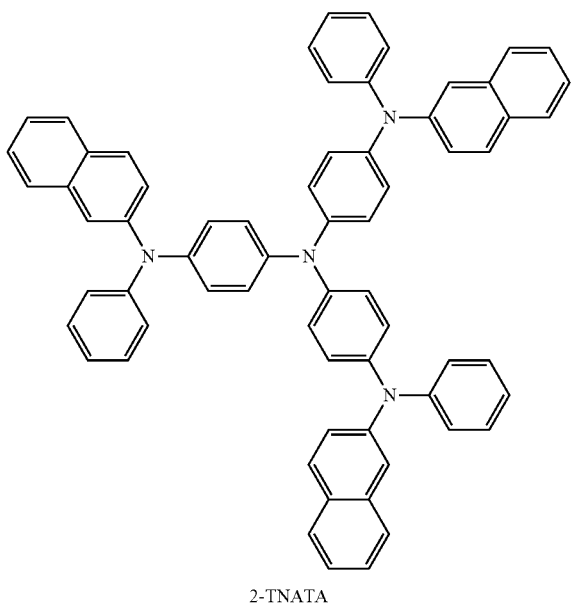

2-TNATA

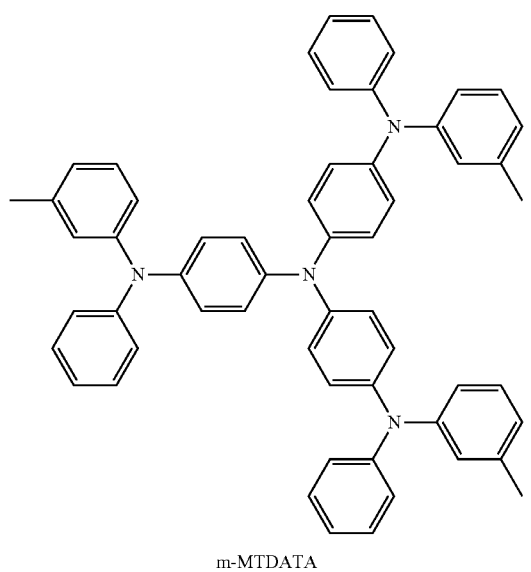

m-MTDATA

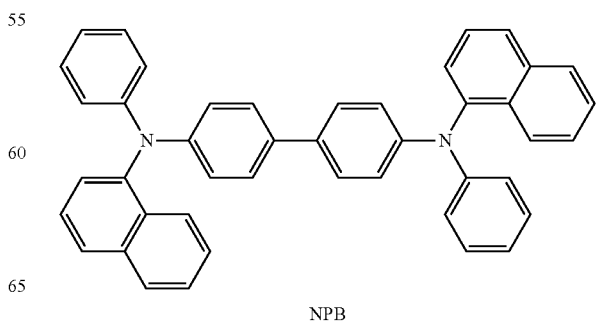

NPB

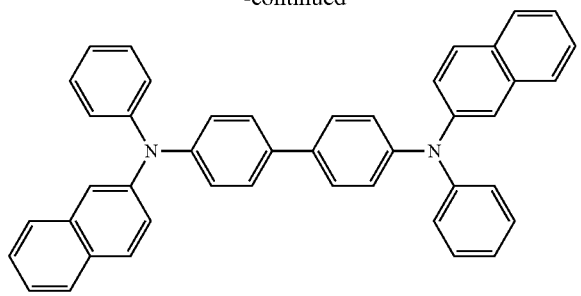

β-NPB

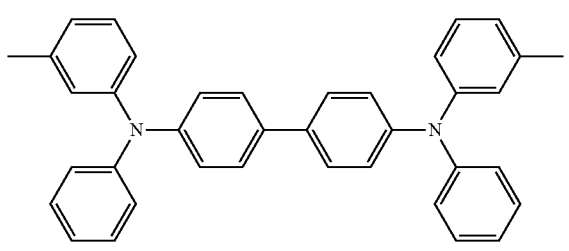

TPD

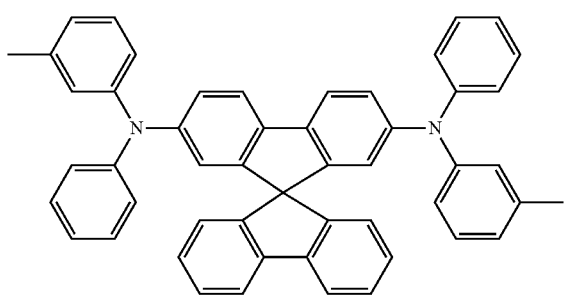

Spiro-TPD

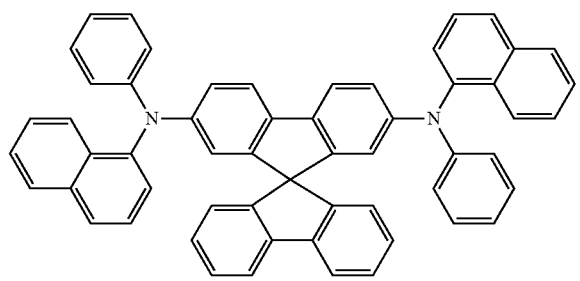

Spiro-NPB

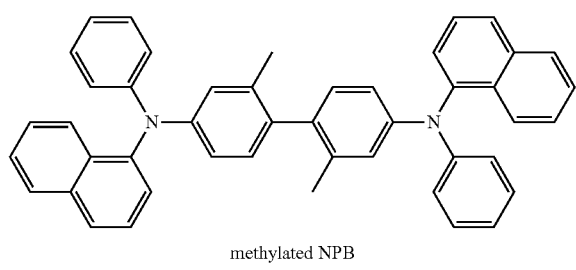

methylated NPB

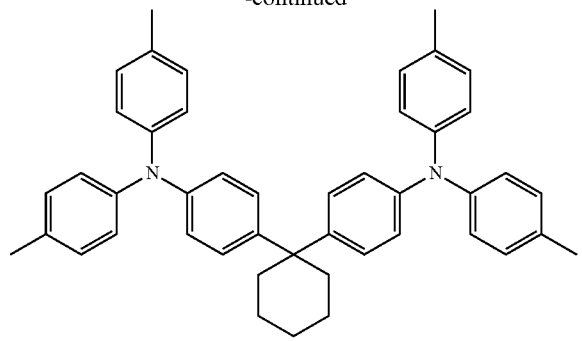

TAPC

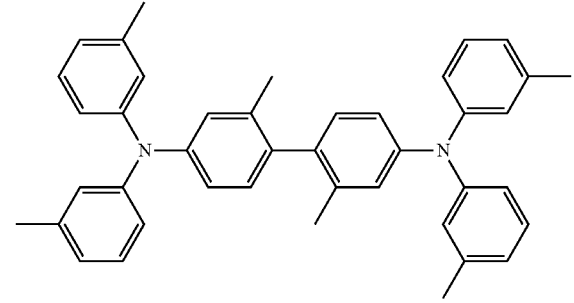

HMTPD

Formula 201

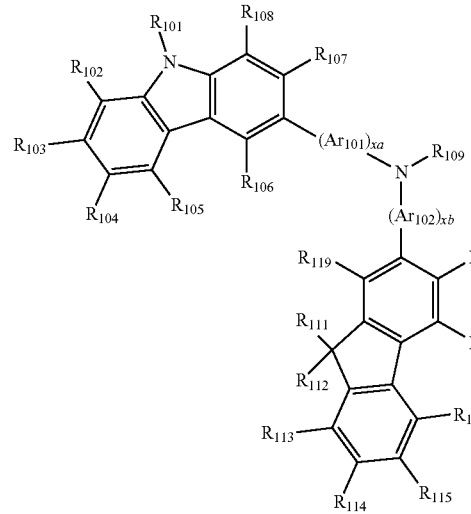

Formula 202

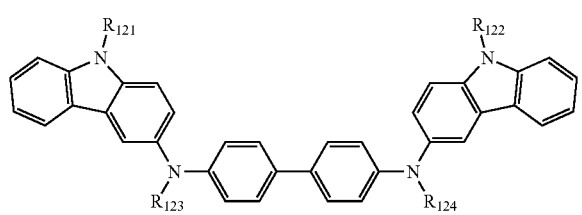

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer from 0 to 5, or 0, 1, or 2. For example, xa is 1 and xb is 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but embodiments of the present disclosure are not limited thereto:

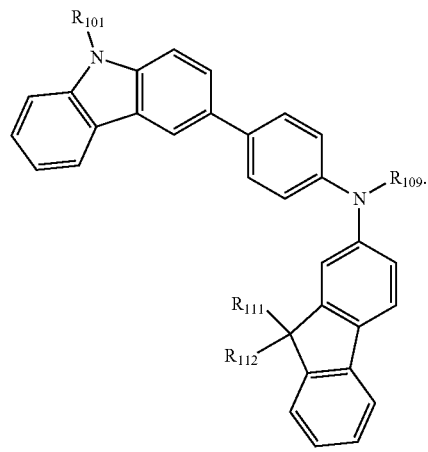

Formula 201A $R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

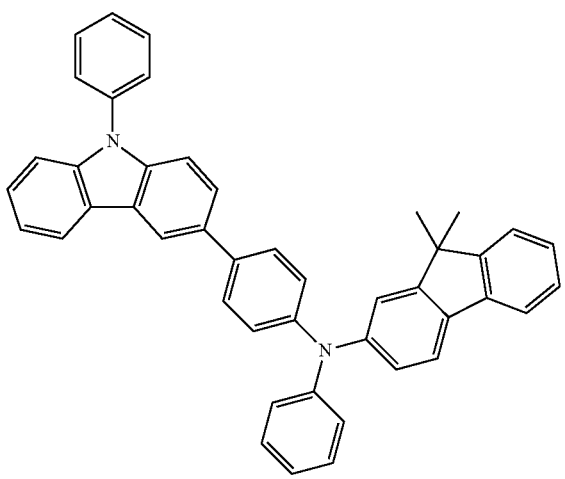

HT1

HT2
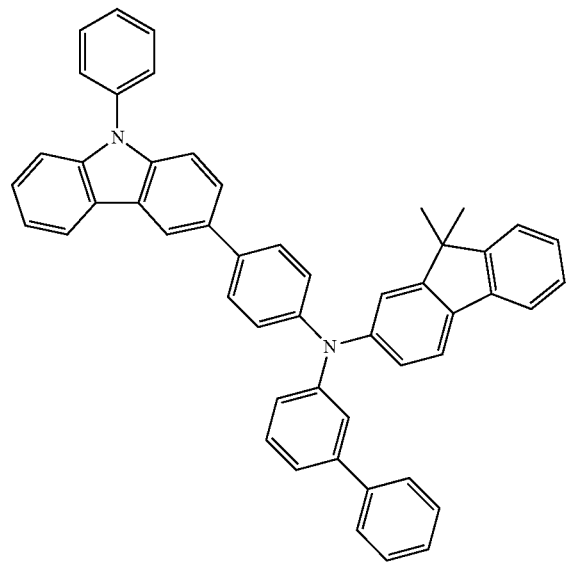
HT4
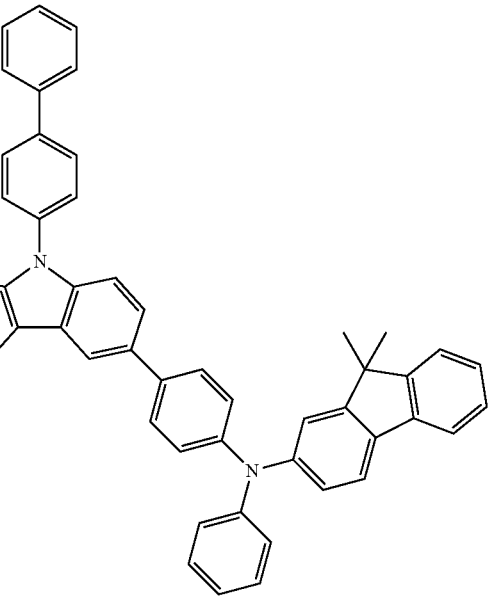
HT3
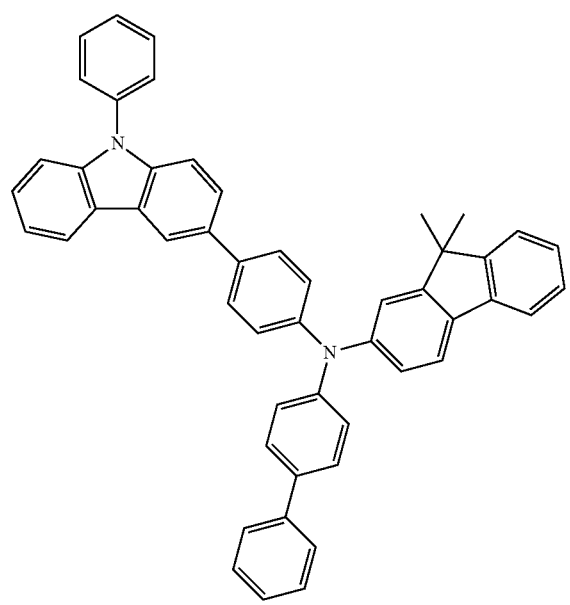
HT5
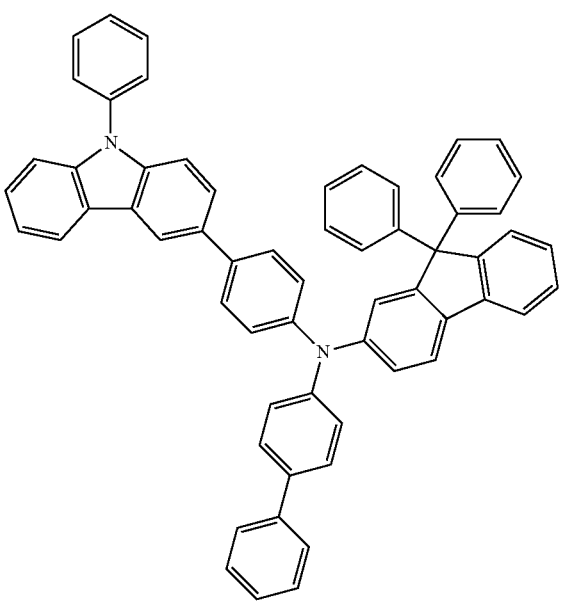

HT6
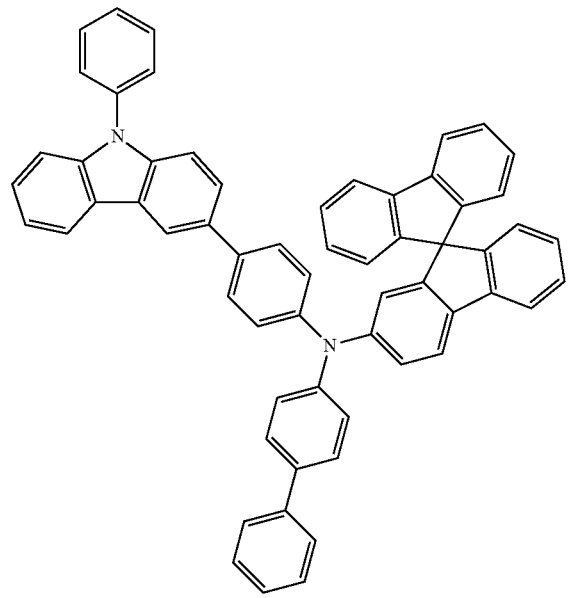
HT7
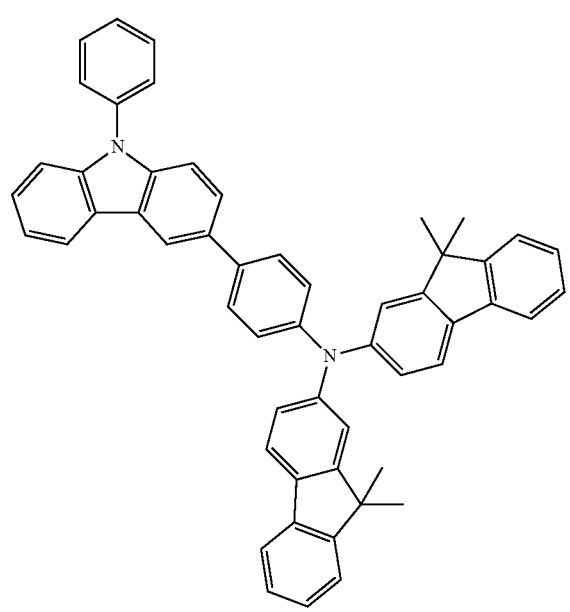
HT8
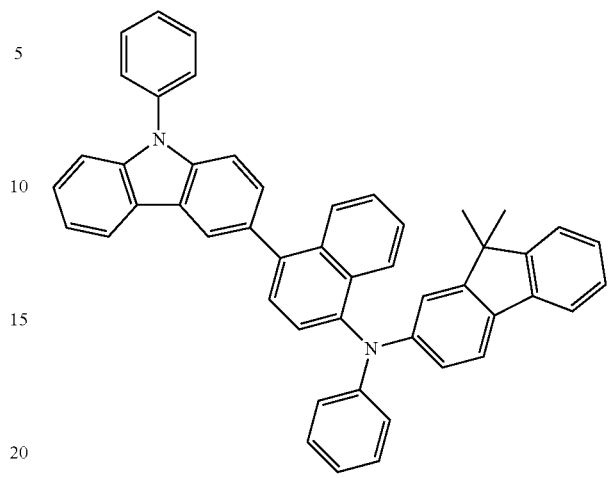
HT9
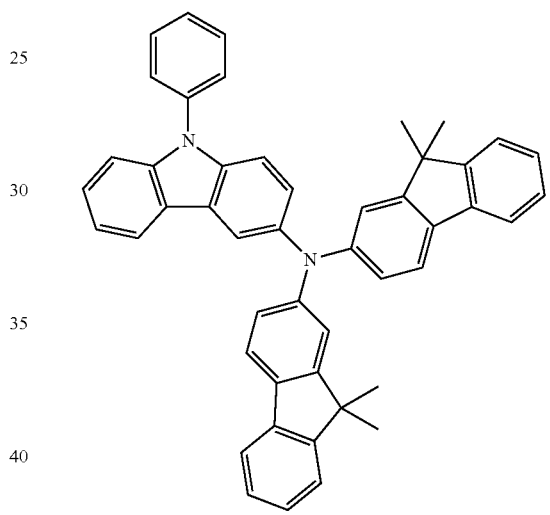
HT10
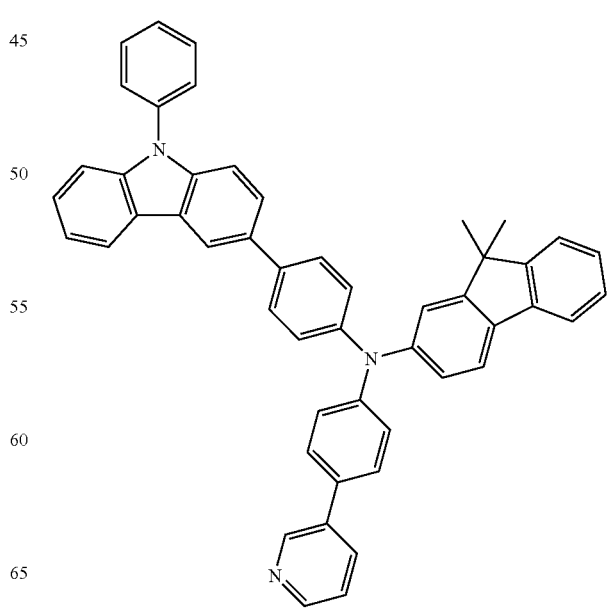

HT11
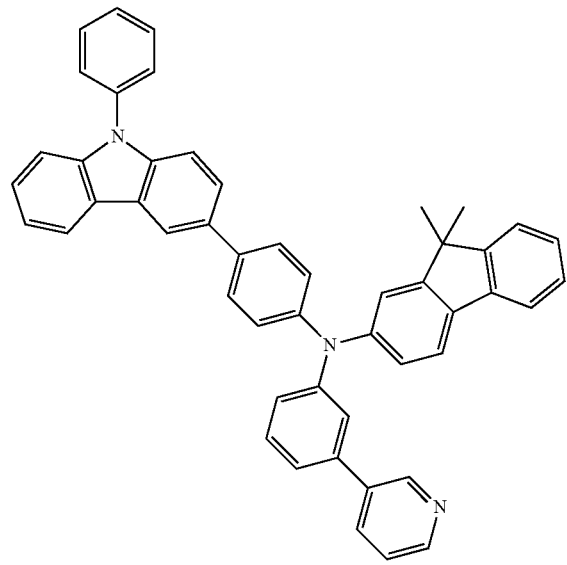
HT12
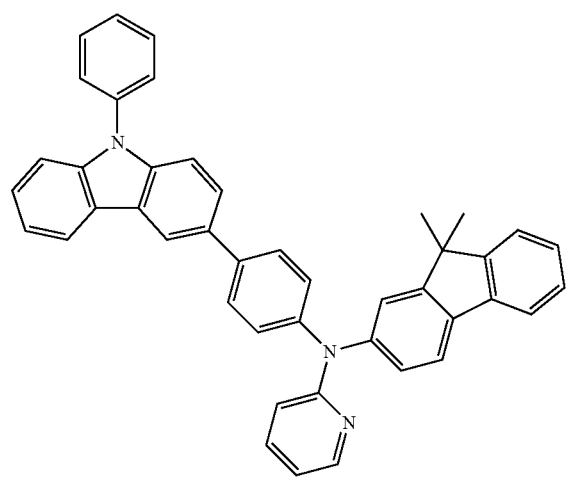
HT13
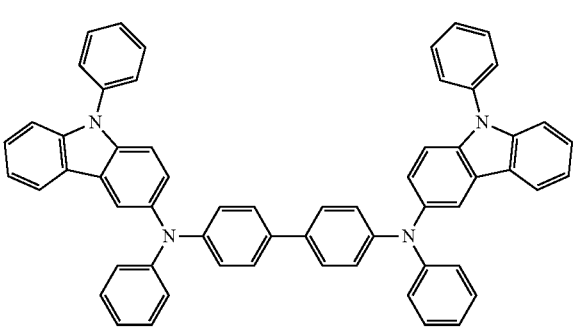
HT14
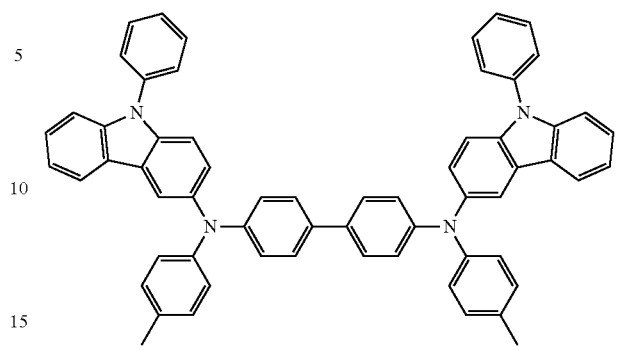
HT15
HT16
HT17
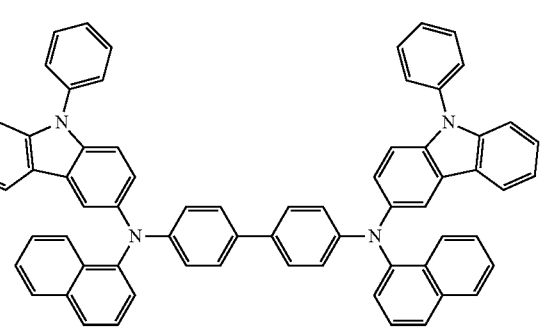

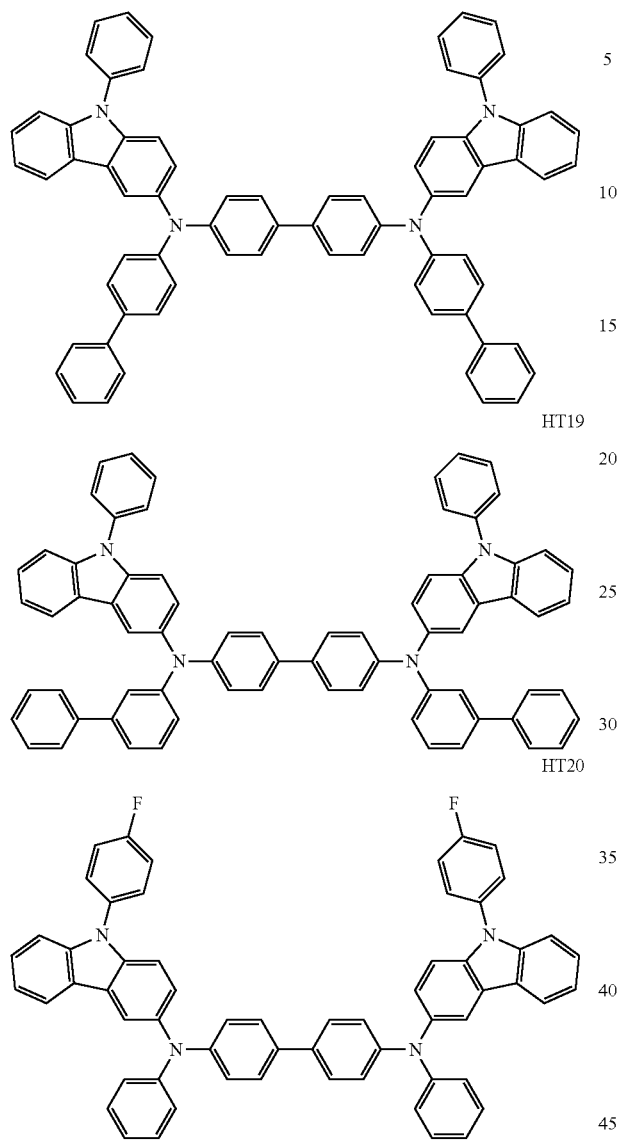

HT18

HT19

HT20

A thickness of the hole transport region may be in a range of about 100 Angstroms (Å) to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

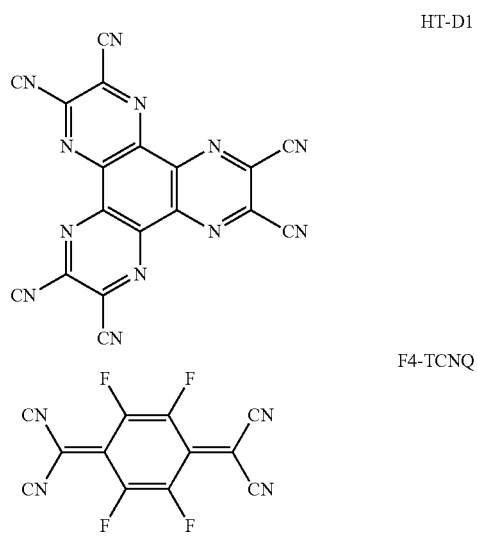

HT-D1

F4-TCNQ

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

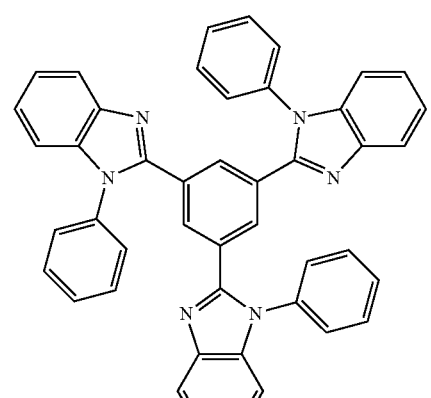
TPBi
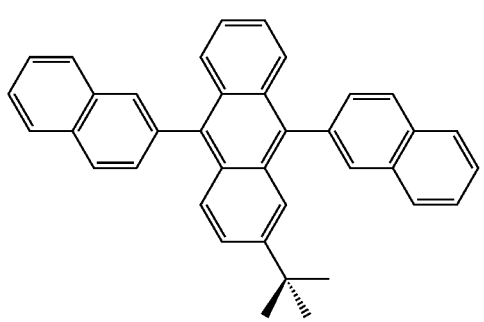
TBADN
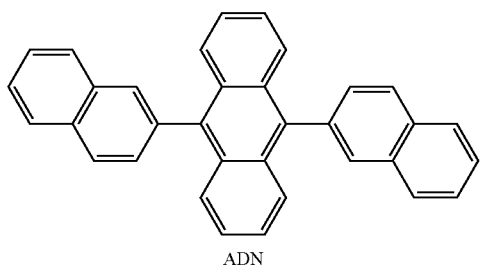
ADN
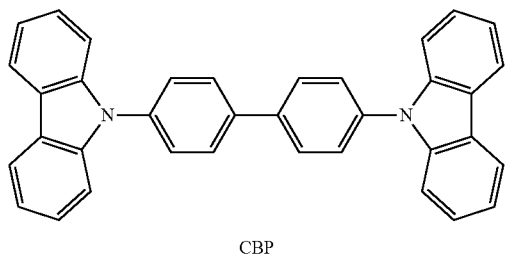
CBP
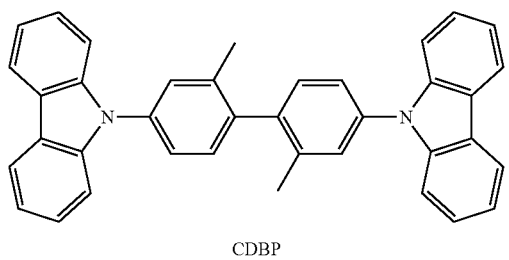
CDBP
-continued
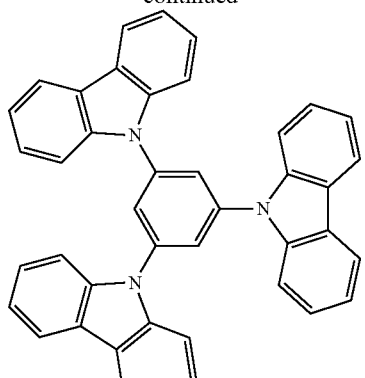
TCP
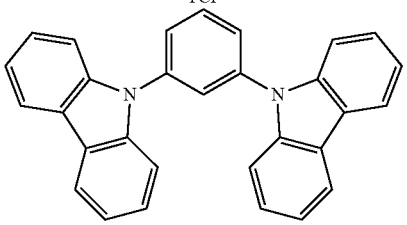
mCP
H50
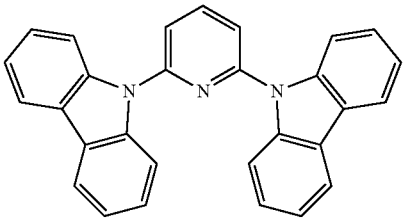
H51
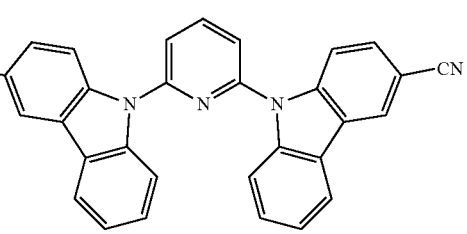
In one or more embodiments, the host may further include a compound represented by Formula 301 below.
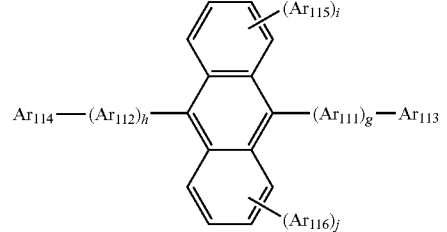
Formula 301
In an embodiment, in Formula 301, $Ar_{111}$ and $Ar_{112}$ may each independently be selected from:
a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group, $Ar_{113}$ to $Ar_{116}$ may each independently be selected from:
a $C_1$-$C_{10}$ alkyl group, a phenyl group, a naphthyl group, a phenanthrenyl group, and a pyrenyl group; and
a phenyl group, a naphthyl group, a phenanthrenyl group, and a pyrenyl group, each substituted with at least one selected from a phenyl group, a naphthyl group, and an anthracenyl group, and g, h, i, and j may each independently be an integer from 0 to 4, and may be, for example, 0, 1, or 2.

In one or more embodiments, in Formula 301, $Ar_{113}$ to $Ar_{116}$ may each independently be selected from:
a $C_1$-$C_{10}$ alkyl group, the substituted with at least one selected from a phenyl group, a naphthyl group, and an anthracenyl group;
a phenyl group, a naphthyl group, an anthracenyl group, a pyrenyl, a phenanthrenyl group, and a fluorenyl group;
a phenyl group, a naphthyl group, an anthracenyl group, a pyrenyl group, a phenanthrenyl group, and a fluorenyl group, each substituted deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

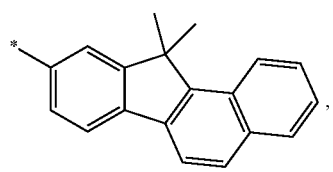 [SMILES: *c1ccc2c(c1)C(C)(C)c1c-2ccc2ccccc12]

but embodiments of the present disclosure are not limited thereto.

In one or more embodiments, the host may include a compound represented by Formula 302 below:

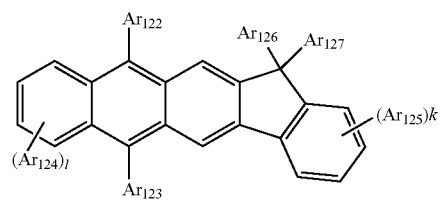

Formula 302

$Ar_{122}$ to $Ar_{125}$ in Formula 302 are the same as described in detail in connection with $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer from 0 to 4. For example, k and l may be 0, 1, or 2.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

When the emission layer includes a host and a dopant, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within the ranges above, excellent light-emission characteristics may be obtained without a substantial increase in driving voltage.

Next, an electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq but embodiments of the present disclosure are not limited thereto.

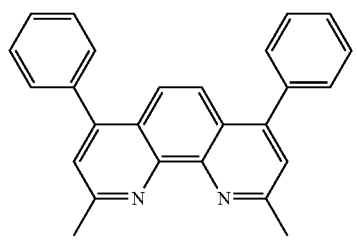

BCP

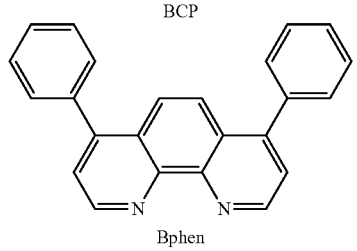

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq$_3$, BAlq, TAZ, and NTAZ.

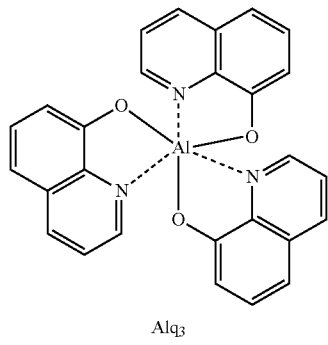

Alq$_3$

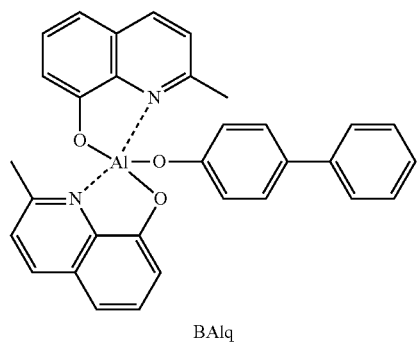

BAlq

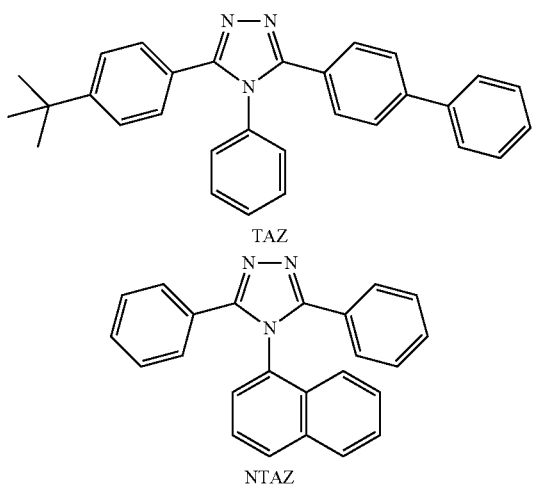

TAZ

NTAZ

In one or more embodiments, the electron transport layer may include at least one of ET1 to ET25, but are not limited thereto:

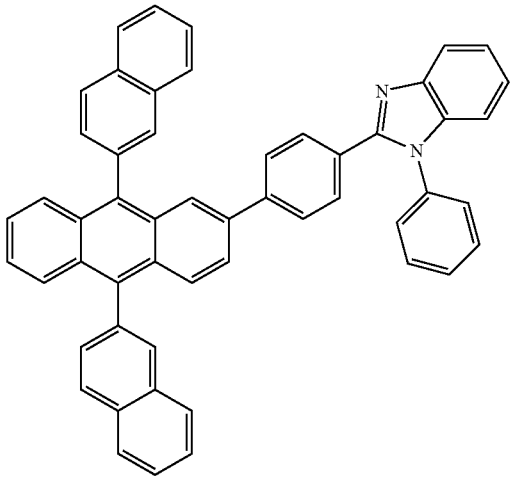

ET1

ET2

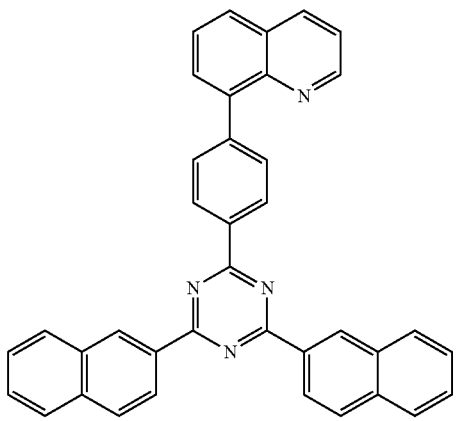

ET3

-continued
ET4
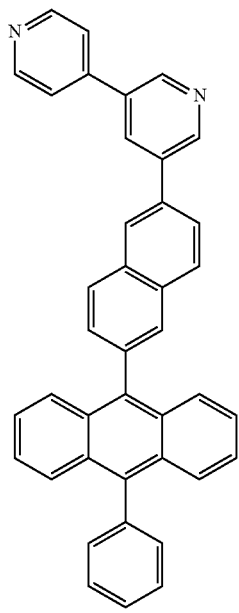
ET5
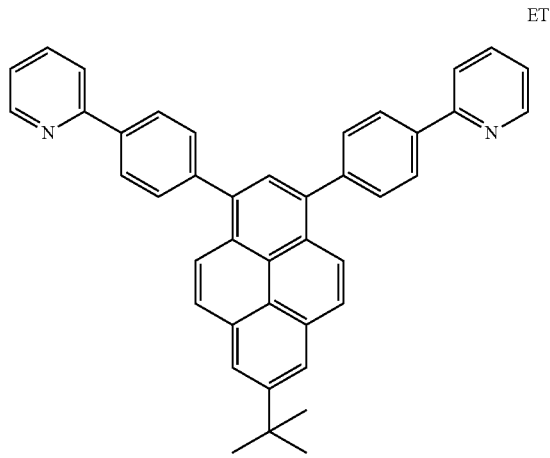
ET6
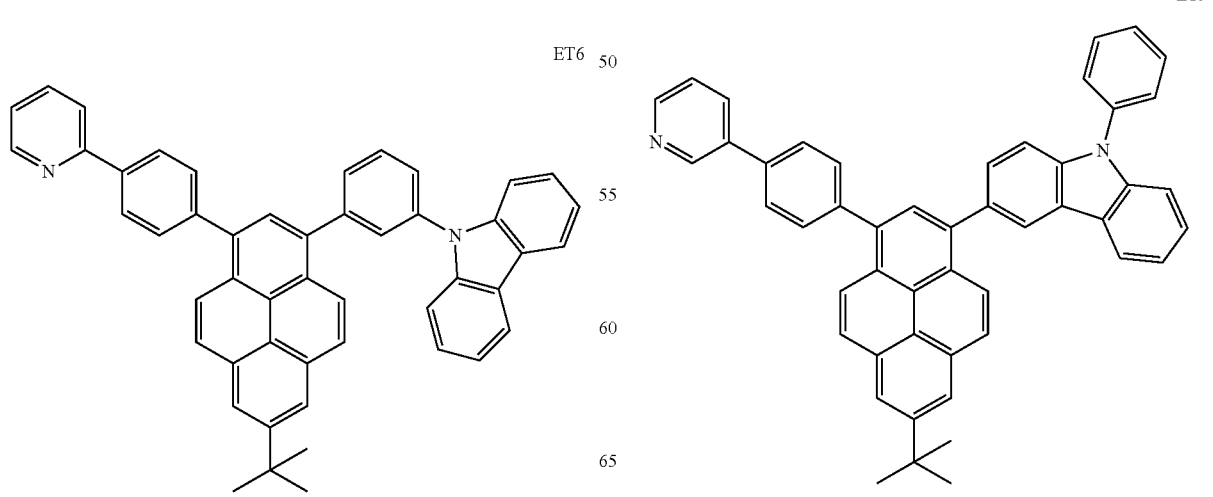
ET7
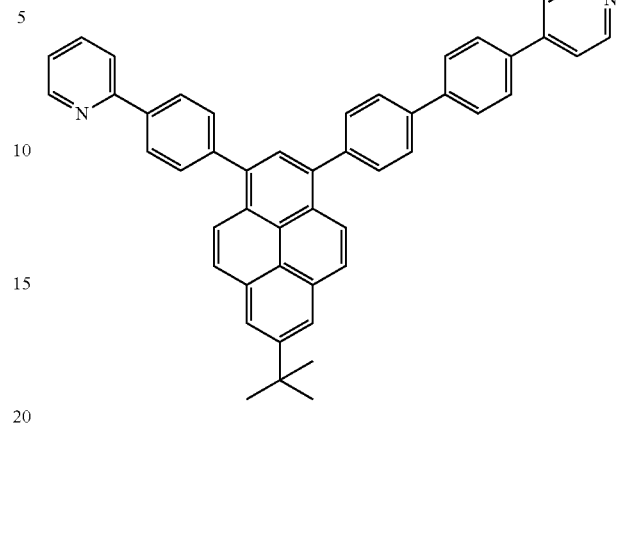
ET8
ET9

-continued
ET10
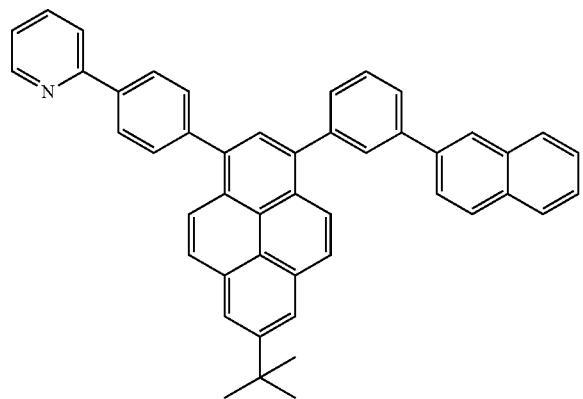
ET11
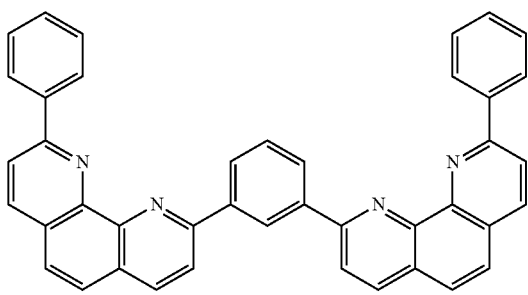
ET12
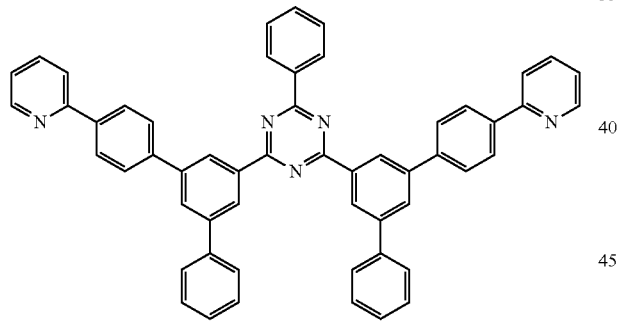
ET13
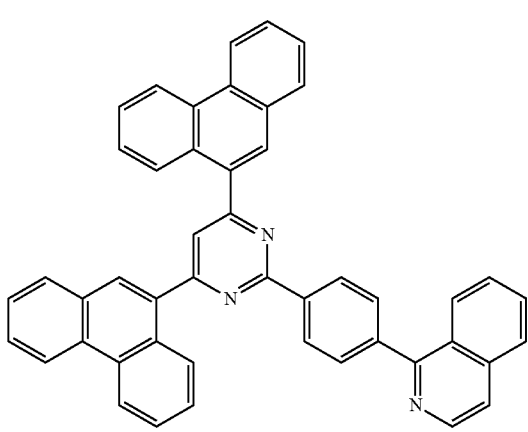
-continued
ET14
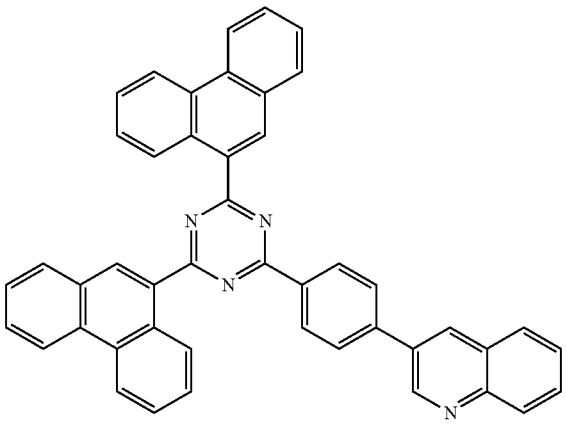
ET15
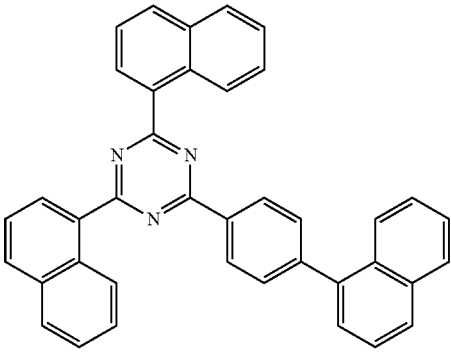
ET16
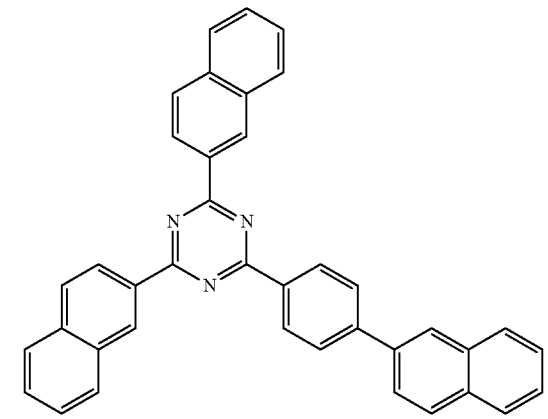

ET17
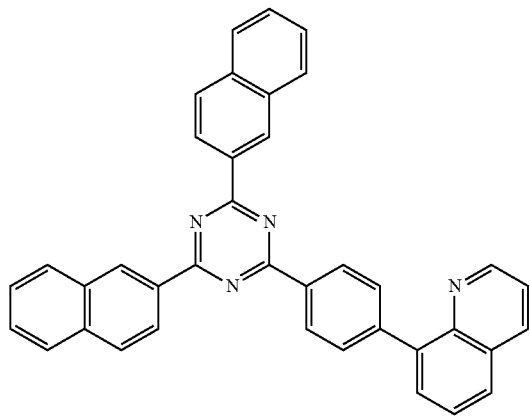
ET20
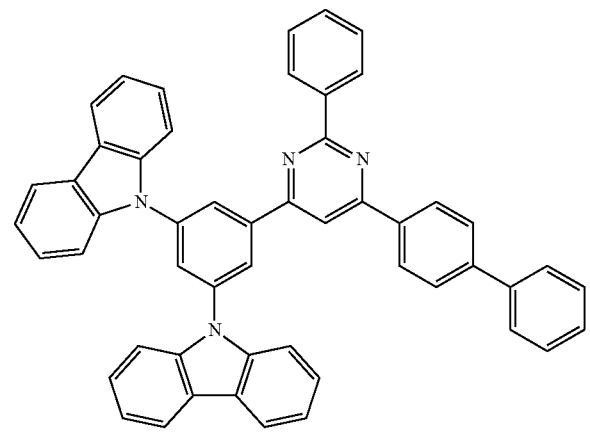
ET18
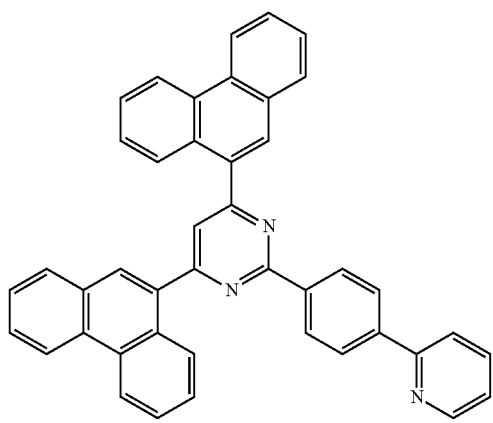
ET21
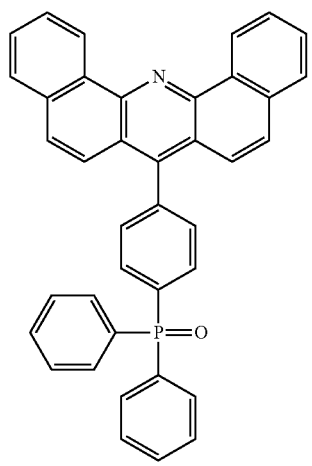
ET19
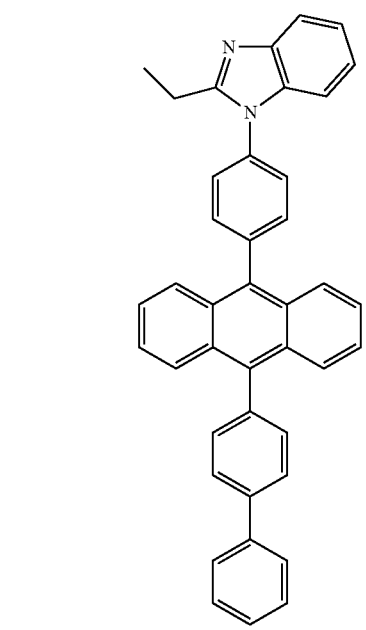
ET22
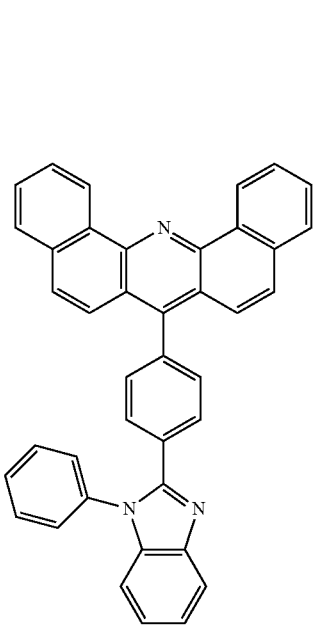

-continued

ET23

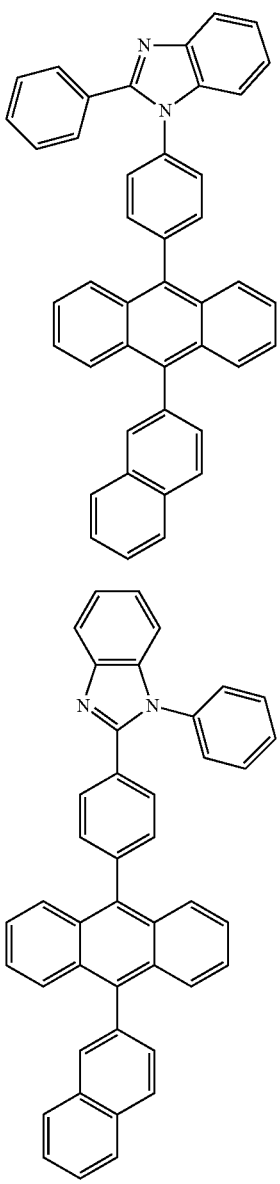

ET24

ET25

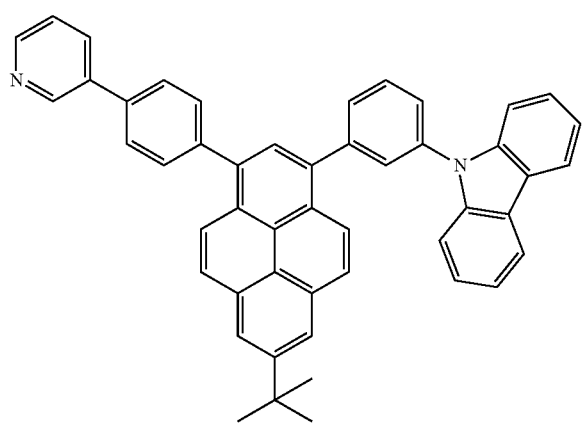

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium 8-hydroxyquinolate, LiQ) or ET-D2.

ET-D1

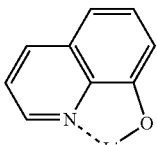

ET-D2

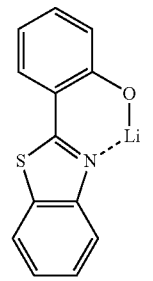

In addition, the electron transport region may include an electron injection layer that facilitates injection of electrons from the second electrode 19.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to the FIGURE, but embodiments of the present disclosure are not limited thereto.

Another aspect of the present disclosure provides a diagnostic composition including at least one organometallic compound represented by Formula 1.

The organometallic compound represented by Formula 1 provides high luminescent efficiency. Accordingly, a diagnostic composition including the organometallic compound may have high diagnostic efficiency.

The diagnostic composition may be used in various applications including a diagnosis kit, a diagnosis reagent, a biosensor, and a biomarker.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, P, Si, and S as a ring-forming atom, and 1 to 60 carbon atoms. The term "$C_1$-$C_{60}$ heteroarylene group" as used herein refers to a divalent group having a carbocyclic aromatic system that has at least one heteroatom selected from N, O, P, Si and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The $C_5$-$C_{30}$ carbocyclic group may be a monocyclic group or a polycyclic group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The $C_1$-$C_{30}$ heterocyclic group may be a monocyclic group or a polycyclic group.

At least one of substituents of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($C$)$_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$), and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1

Synthesis of Compound 1

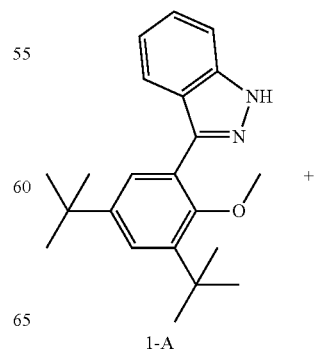

1-A

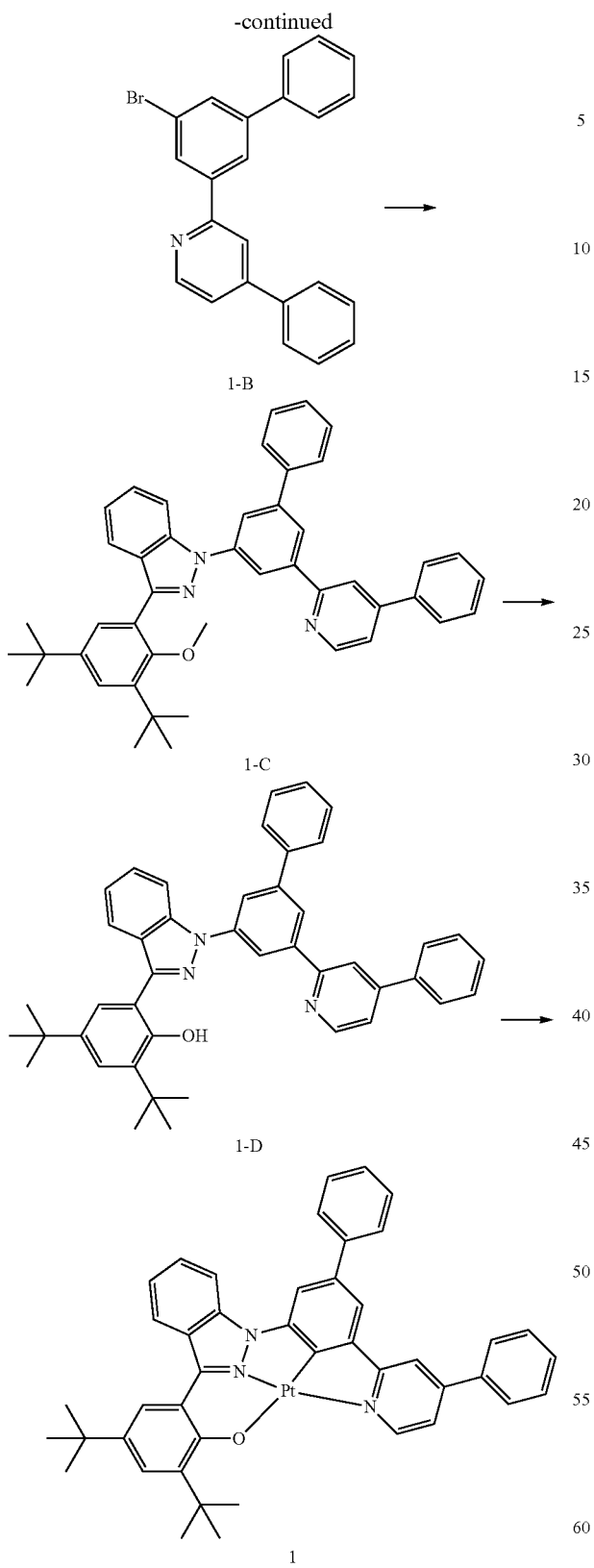

6.78 g (20.8 mmol, 1.4 equiv.) of CsCO$_3$, 1.07 g (2.23 mmol, 0.15 equiv.) of 4,7-dimethoxy-1,10-phenanthroline, and 2.5 g of PEG were mixed with 15 milliliters (mL) of DMF, and the mixed solution was stirred at a temperature of 160° C. overnight. The resulting product obtained therefrom was cooled to room temperature, and the precipitate was filtered. The filtrate was washed with CH$_2$Cl$_2$ and H$_2$O, and purified by column chromatography, thereby obtaining 3.4 g (yield: 59%) of Intermediate 1-C. The product thus obtained was identified by LC-MS analysis.

C$_{45}$H$_{43}$N$_3$O: M$^+$ 641.34

Synthesis of Intermediate 1-D 3 g (6.47 mmol, 1 equiv.) of Intermediate 1-C and 37 g (327 mmol, 70 equiv.) of pyridine hydrochloride were added to a sealing tube, and the mixed solution was stirred at a temperature of 180° C. overnight. The resulting product obtained therefrom was cooled to room temperature, washed with CH$_2$Cl$_2$ and H$_2$O, and then, purified by column chromatography, thereby obtaining 1.8 g (yield: 60%) of Intermediate 1-D. The product thus obtained was identified by LC-MS analysis.

C$_{45}$H$_{43}$N$_3$O: M$^+$ 627.32

Synthesis of Compound 1

1.5 g (2.39 mmol, 1 equiv.) of Intermediate 1-D and 1.19 g (2.87 mmol, 1.2 equiv.) of K$_2$PtCl$_4$ were mixed with a mixture containing 80 mL of AcOH and 3 mL of H$_2$O, and the mixed solution was stirred overnight. The resulting product obtained therefrom was cooled to room temperature, and the precipitate was filtered. The filtrate was dissolved again in methylene chloride (MC), washed with H$_2$O, and then purified by column chromatography, thereby obtaining 1.3 g (yield: 56%) of Compound 1. The product thus obtained was identified by LC-MS analysis.

C$_{44}$H$_{39}$N$_3$OPt: M$^+$ 820.27

Synthesis Example 2

Synthesis of Compound 34

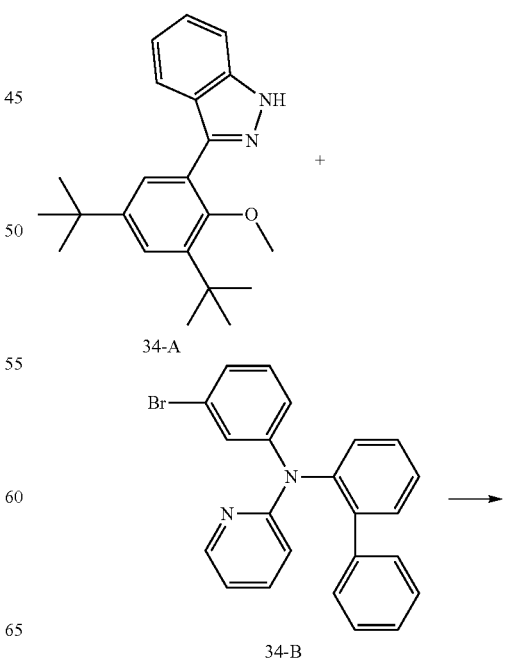

Synthesis of Intermediate 1-C 5 grams (g) (14.86 millimoles, mmol, 1 equivalents, equiv.) of Intermediate 1-A, 5.7 g (14.86 mmol, 1 equiv.) of Intermediate 1-B, 0.11 g (0.74 mmol, 0.05 equiv.) of Cu$_2$O,

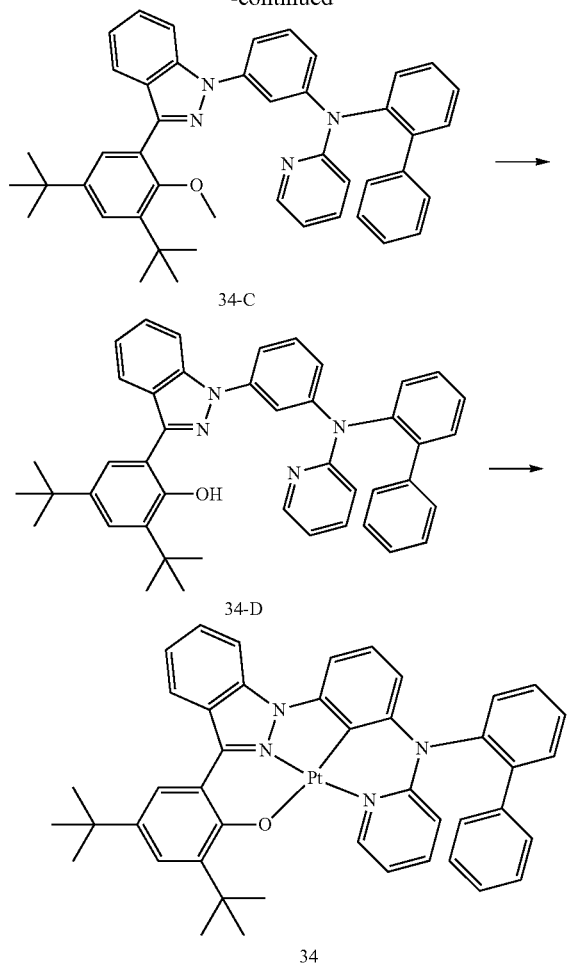

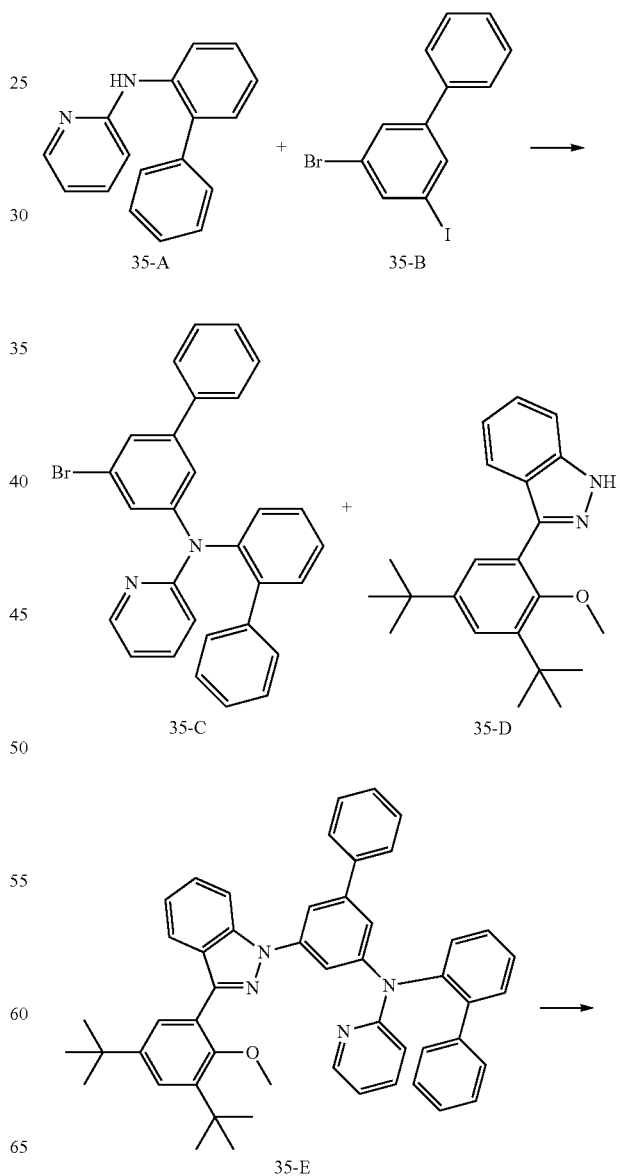

Synthesis of Intermediate 34-C 2.3 g (6.84 mmol, 1 equiv.) of Intermediate 34-A, 2.74 g (6.84 mmol, 1 equiv.) of Intermediate 34-B, 0.05 g (0.34 mmol, 0.05 equiv.) of Cu$_2$O, 3.12 g (9.57 mmol, 1.4 equiv.) of CsCO$_3$, 0.49 g (1.03 mmol, 0.15 equiv.) of 4,7-dimethoxy-1,10-phenanthroline, and 1.15 g of PEG were mixed with 7 mL of DMF, and the mixed solution was stirred at a temperature of 160° C. overnight. The resulting product obtained therefrom was cooled to room temperature, and the precipitate was filtered. The filtrate was washed with CH$_2$Cl$_2$ and H$_2$O, and purified by column chromatography, thereby obtaining 1.4 g (yield: 51%) of Intermediate 34-C. The product thus obtained was identified by LC-MS analysis.

$C_{45}H_{44}N_4O$: M$^+$ 656.35

Synthesis of Intermediate 34-D 1.3 g (1.98 mmol, 1 equiv.) of Intermediate 34-C and 16.01 g (138.54 mmol, 70 equiv.) of pyridine hydrochloride were added to a sealing tube, and the mixed solution was stirred at a temperature of 180° C. overnight. The resulting product obtained therefrom was cooled to room temperature, washed with CH$_2$Cl$_2$ and H$_2$O, and then, purified by column chromatography, thereby obtaining 0.60 g (yield: 47%) of Intermediate 34-D. The product thus obtained was identified by LC-MS analysis.

$C_{44}H_{42}N_4O$: M$^+$ 642.34

Synthesis of Compound 34

0.60 g (0.96 mmol, 1 equiv.) of Intermediate 34-D and 0.48 g (2.87 mmol, 1.2 equiv.) of K$_2$PtCl$_4$ were mixed with a mixture containing 80 mL of AcOH and 3 mL of H$_2$O, and the mixed solution was stirred overnight. The resulting product obtained therefrom was cooled to room temperature, and the precipitate was filtered. The filtrate was dissolved again in MC, washed with H$_2$O, and then purified by column chromatography, thereby obtaining 1.3 g (yield: 56%) of Compound 34. The product thus obtained was identified by LC-MS analysis.

$C_{44}H_{39}N_3OPt$: M$^+$ 820.27

Synthesis Example 3

Synthesis of Compound 35

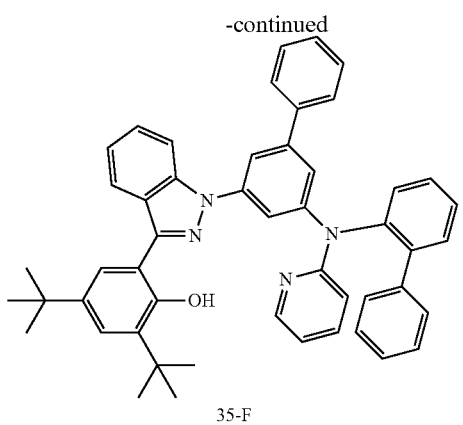

35-F

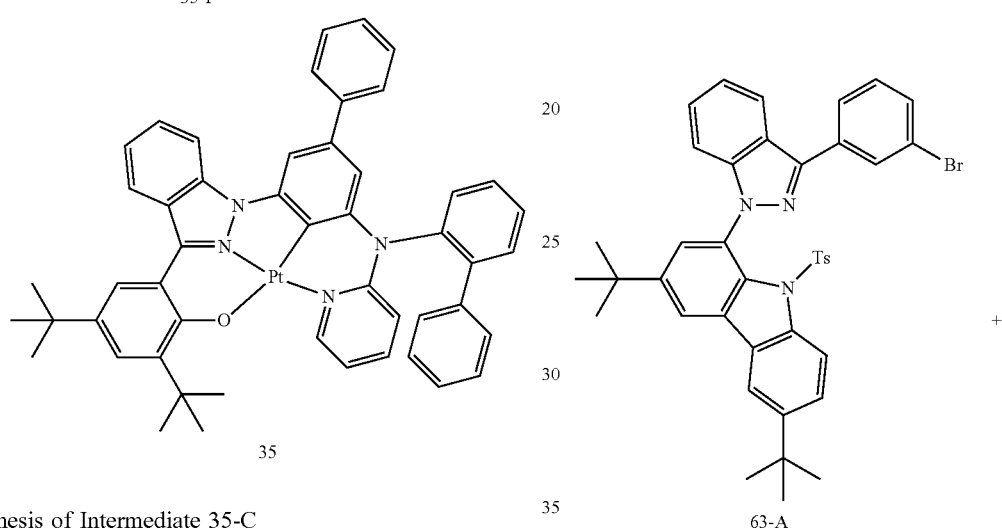

35

Synthesis of Intermediate 35-C 4.5 g (18.27 mmol, 1 equiv.) of Intermediate 35-A, 6.56 g (18.27 mmol, 1 equiv.) of Intermediate 35-B, 0.13 g (0.91 mmol, 0.05 equiv.) of $Cu_2O$, 8.33 g (25.58 mmol, 1.4 equiv.) of $CsCO_3$, 1.32 g (2.74 mmol, 0.15 equiv.) of 4,7-dimethoxy-1,10-phenanthroline, and 2.25 g of PEG were mixed with 18 mL of DMF, and the mixed solution was stirred at a temperature of 160° C. overnight. The resulting product obtained therefrom was cooled to room temperature, and the precipitate was filtered. The filtrate was washed with $CH_2Cl_2$ and $H_2O$, and purified by column chromatography, thereby obtaining 3.6 g (yield: 49%) of Intermediate 35-C. The product thus obtained was identified by LC-MS analysis.

$C_{29}H_{21}BrN_2$: $M^+$ 476.09

Synthesis of Intermediate 35-E 3.5 g (yield: 48%) of Intermediate 35-E was synthesized in the same manner as used to synthesize Intermediate 35-C, except that 2.84 g (5.94 mmol) of Intermediate 35-C and 2.0 g (5.94 mmol) of Intermediate 35-D were used instead of Intermediate 35-B and Intermediate A, respectively.

$C_{51}H_{48}N_4O$: $M^+$ 732.38

Synthesis of Intermediate 35-F 1.5 g (yield: 57%) of Intermediate 35-F was synthesized in the same manner as used to synthesize Intermediate 34-D in Synthesis Example 2, except that 3 g (4.09 mmol, 1 equiv.) of Intermediate 35-E was used instead of Intermediate 34-C.

$C_{50}H_{46}N_4O$: $M^+$ 718.37

Synthesis of Compound 35

1.5 g (2.09 mmol, 1 equiv.) of Intermediate 35-E and 1.04 g (2.51 mmol, 1.2 equiv.) of $K_2PtCl_4$ were mixed with a mixture containing 30 mL of AcOH and 1 mL of $H_2O$, and the mixed solution was stirred overnight. The resulting product obtained therefrom was cooled to room temperature, and the precipitate was filtered. The filtrate was dissolved again in MC, washed with $H_2O$, and then purified by column chromatography, thereby obtaining 0.8 g (yield: 46%) of Compound 35. The product thus obtained was identified by LC-MS analysis.

$C_{50}H_{44}N_4OPt$: $M^+$ 911.32

Synthesis Example 4

Synthesis of Compound 63

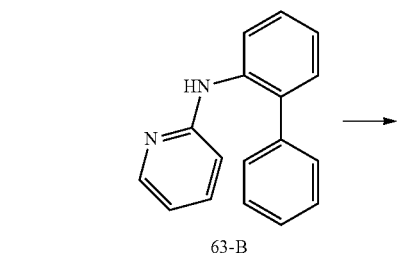

63-A

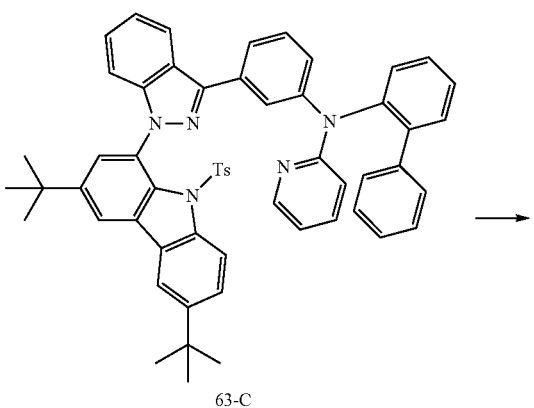

63-B

63-C

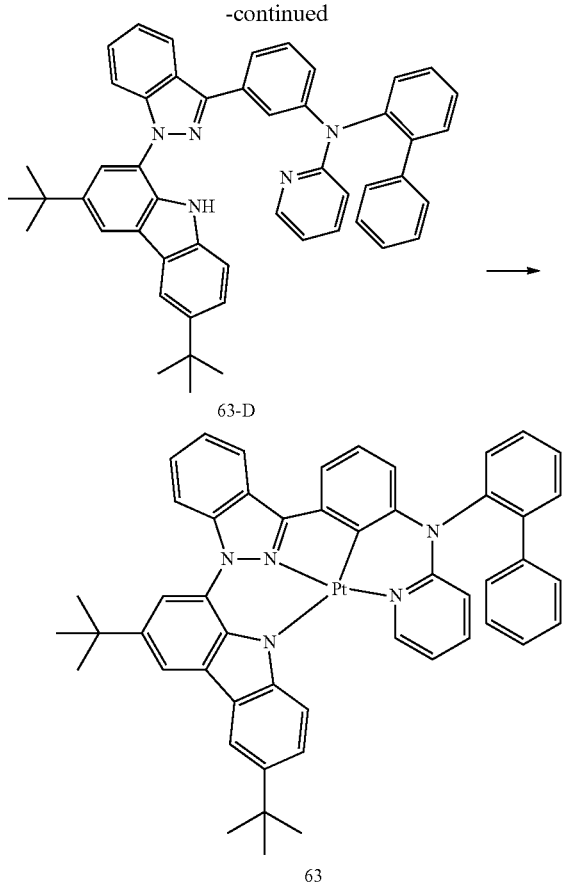

Synthesis of Intermediate 63-C 4.5 g (18.27 mmol, 1 equiv.) of Intermediate 63-A, 12.62 g (18.27 mmol, 1 equiv.) of Intermediate 63-B, 0.13 g (0.91 mmol, 0.05 equiv.) of $Cu_2O$, 8.33 g (25.58 mmol, 1.4 equiv.) of $CsCO_3$, 1.32 g (2.74 mmol, 0.15 equiv.) of 4,7-dimethoxy-1,10-phenanthroline, and 2.25 g of PEG were mixed with 18 mL of DMF. The mixed solution was stirred at a temperature of 160° C. overnight. The resulting product obtained therefrom was cooled to room temperature, and the precipitate was filtered. The filtrate was washed with $CH_2Cl_2$ and $H_2O$, and purified by column chromatography, thereby obtaining 6.2 g (yield: 40%) of Intermediate 63-C. The product thus obtained was identified by LC-MS analysis.

$C_{56}H_{49}N_5O_2S$: $M^+$ 855.36

Synthesis of Intermediate 63-D 6 g (7.01 mmol, 1 equiv.) of Intermediate 63-C and KOH (21.03 mmol, 3 equiv.) were added to 100 mL of EtOH, and the mixed solution was stirred for 4 hours. After the reaction was completed, the reaction product was cooled to room temperature, and the precipitate was filtered. The filtrate was washed with $CH_2Cl_2$ and $H_2O$, and purified by column chromatography, thereby obtaining 3.7 g (yield: 74%) of Intermediate 63-D. The product thus obtained was identified by LC-MS analysis.

$C_{50}H_{45}N_5$: $M^+$ 715.37

Synthesis of Compound 63

2 g (2.79 mmol, 1 equiv.) of Intermediate 63-D and 1.39 g (3.35 mmol, 1.2 equiv.) of $K_2PtCl_4$ were mixed with a mixture containing 70 mL of AcOH and 1 mL of $H_2O$, and the mixed solution was stirred overnight. The resulting product obtained therefrom was cooled to room temperature, and the precipitate was filtered. The filtrate was dissolved again in MC, washed with $H_2O$, and then purified by column chromatography, thereby obtaining 1.1 g (yield: 43%) of Compound 63. The product thus obtained was identified by LC-MS analysis.

$C_{50}H_{43}N_5Pt$: $M^+$ 908.32

Example 1

As an anode, a glass substrate, on which ITO/Ag/ITO were deposited to thicknesses of 70 Å/1,000 Å/70 Å, was cut to a size of 50 mm×50 mm×0.5 mm (mm=millimeters), sonicated with iso-propyl alcohol and pure water each for 5 minutes, and then cleaned by exposure to ultraviolet rays and ozone for 30 minutes. Then, the glass substrate was provided to a vacuum deposition apparatus.

2-TNATA was deposited on the anode to form a hole injection layer having a thickness of 600 Å, and 4,4'-bis[N-(1-naphthyl)-N-phenylamino]biphenyl (NPB) was deposited on the hole injection layer to form a hole transport layer having a thickness of 1,350 Å.

CBP (host) and Compound 1 (dopant) were co-deposited on the hole transport layer at a weight ratio of 94:6 to form an emission layer having a thickness of 400 Å, BCP was deposited on the emission layer to form a hole blocking layer having a thickness of 50 Å. Then, $Alq_3$ was deposited on the hole blocking layer to form an electron transport layer having a thickness of 350 Å, LiF was deposited on the electron transport layer to form an electron injection layer having a thickness of 10 Å, and MgAg was deposited on the electron injection layer at a weight ratio of 90:10 to form a cathode having a thickness of 120 Å, thereby completing the manufacture of an organic light-emitting device (which emits red light) having a structure of ITO/Ag/ITO/2-TNATA (600 Å)/NPB (1,350 Å)/CBP+Compound 1 (6 weight %) (400 Å)/BCP (50 Å)/$Alq_3$ (350 Å)/LiF (10 Å)/MgAg (120 Å).

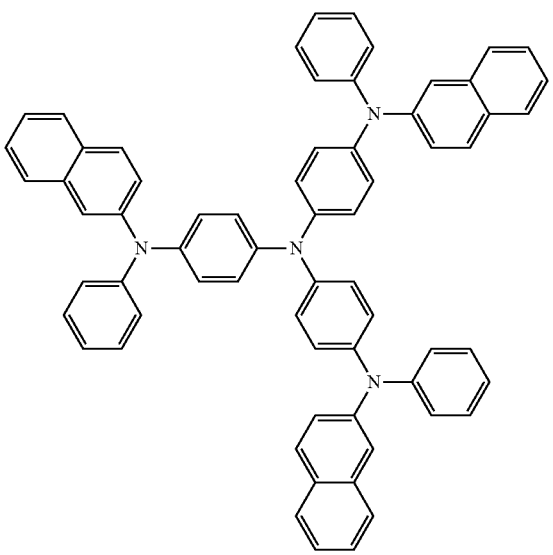

2-TNATA

-continued

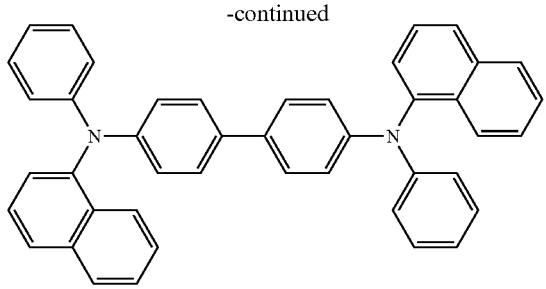

NPB

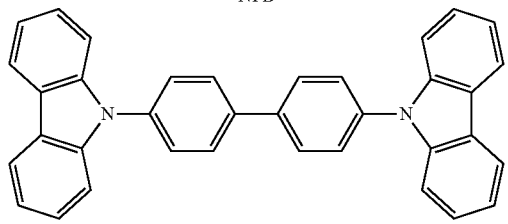

CBP

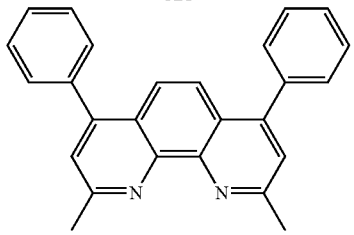

BCP

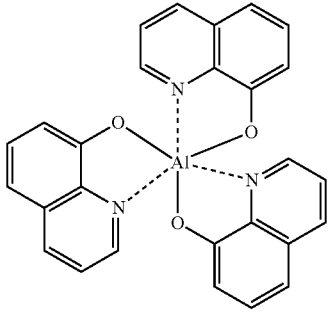

Alq3

Examples 2 to 4 and Comparative Examples A and B

Organic light-emitting devices were manufactured in the same manner as in Example 1, except that the compounds shown in Table 2 were each used instead of Compound 1 as a dopant in forming an emission layer.

Evaluation Example 1

Evaluation of Characteristics of Organic Light-Emitting Devices

Each of the organic light-emitting devices of Examples 1 to 4 and Comparative Examples A and B were evaluated in terms of a driving voltage, an emission efficiency, and a maximum emission peak wavelength ($\lambda_{max}$), and the evaluation results are shown in Table 2. Here, a current-voltage meter (Keithley 2400) and a luminance meter (Minolta Cs-1000A) were utilized for the evaluation.

TABLE 2

| | Dopant | Driving voltage (V) | Emission efficiency (cd/A) | Maximum emission peak wavelength ($\lambda_{max}$) (nm) |
|---|---|---|---|---|
| Example 1 | Compound 1 | 4.67 | 28.9 | 611 |
| Example 2 | Compound 34 | 4.86 | 26.7 | 570 |
| Example 3 | Compound 35 | 4.53 | 29.6 | 573 |
| Example 4 | Compound 63 | 4.61 | 27.2 | 641 |
| Comparative Example A | Compound A | 5.81 | 14.1 | 422 |
| Comparative Example B | Compound B | 5.24 | 17.3. | 510 |

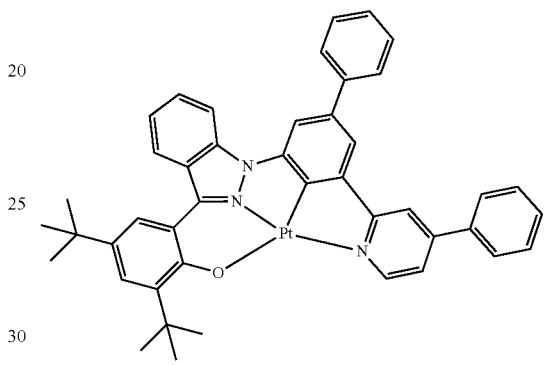

1

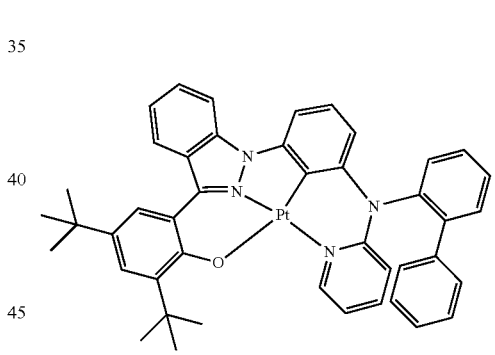

34

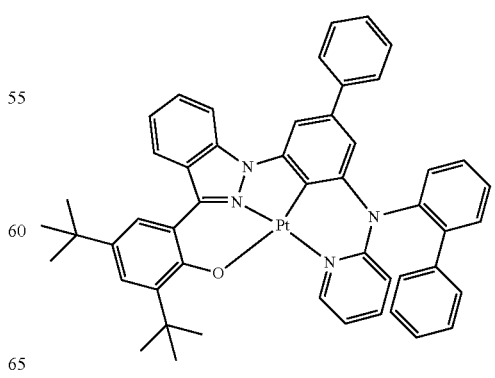

35

TABLE 2-continued

| Dopant | Driving voltage (V) | Emission efficiency (cd/A) | Maximum emission peak wavelength ($\lambda_{max}$) (nm) |
|---|---|---|---|

(structures 63, A, B shown)

Referring to Table 2, it was confirmed that the organic light-emitting devices of Examples 1 to 4 had excellent driving voltage and emission efficiency as compared with the organic light-emitting devices of Comparative Examples A and B.

Since the organometallic compound has excellent electric characteristics and thermal stability, an organic light-emitting device including the organometallic compound may have excellent driving voltage, efficiency, power, color purity, and lifespan characteristics. In addition, since the organometallic compound has excellent phosphorescence characteristics, the use of the organometallic compound may provide a diagnostic compound having high diagnostic efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present description as defined by the following claims.

What is claimed is:

1. An organometallic compound represented by Formula 1:

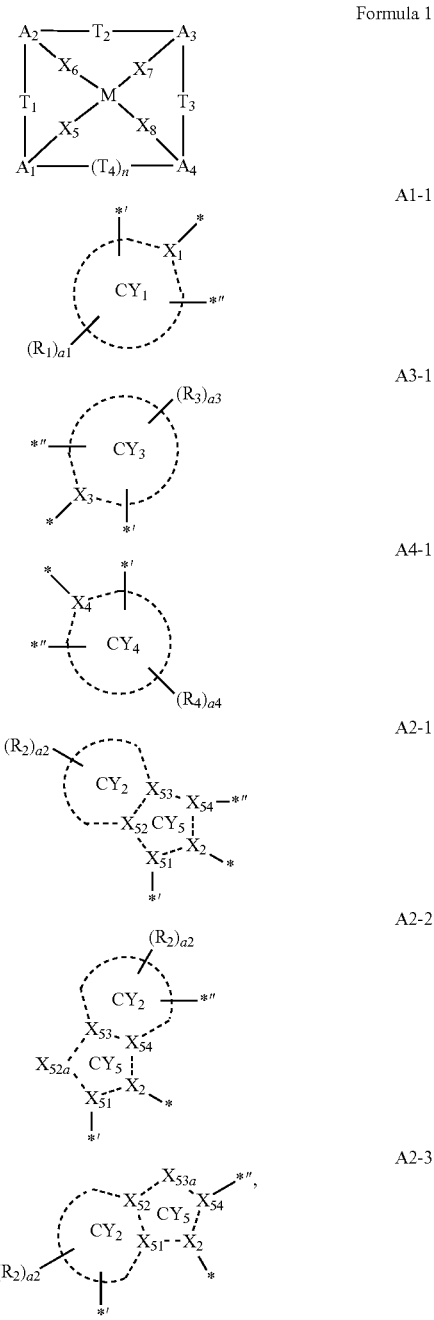

wherein, in Formula 1,

M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), in Formula 1, two bonds selected from a bond between $A_1$ or $X_5$ and M, a bond between $A_2$ or $X_6$ and M, a bond between $A_3$ or $X_7$ and M, and a bond between $A_4$ or $X_8$ and M are each a covalent bond, and the others thereof are each a coordinate bond, provided that (i) M forms a covalent bond to oxygen and a covalent bond to carbon, (ii) M forms a covalent bond to oxygen and a covalent bond to nitrogen, (iii) M forms a covalent bond to nitrogen and a covalent bond to carbon, wherein $A_1$ comprises a carbazole group, or (iv) M forms two covalent bonds to nitrogens, wherein $A_1$ comprises a carbazole group, in Formula 1, $A_1$ is a ring represented by Formula A1-1, and in Formula A1-1, * indicates a binding site to $X_5$ in Formula 1, *' indicates a binding site to T in Formula 1, and *" indicates a binding site to $T_4$ in Formula 1, in Formula 1, $A_2$ is a ring represented by one selected from Formulae A2-1 to A2-3, and in Formulae A2-1 to A2-3, * indicates a binding site to $X_6$ in Formula 1, *' indicates a binding site to $T_1$ in Formula 1, and *" indicates a binding site to $T_2$ in Formula 1, in Formula 1, $A_3$ is a ring represented by Formula A3-1, and in Formula A3-1, * indicates a binding site to $X_7$ in Formula 1, *" indicates a binding site to $T_2$ in Formula 1, and *' indicates a binding site to $T_3$ in Formula 1, in Formula 1, $A_4$ is a first atom linked to $X_8$ or M, a non-cyclic moiety comprising the first atom linked to $X_8$ or M, or a ring represented by Formula A4-1, and in Formula A4-1, * indicates a binding site to $X_8$ in Formula 1, *' indicates a binding site to $T_3$ in Formula 1, and *" indicates a binding site to $T_4$ in Formula 1, the first atom is B, P, N, C, Si, O, or S, in Formulae A1-1, A2-1 to A2-3, A3-1, and A4-1, $X_1$, $X_3$, $X_4$, and $X_{51}$ to $X_{54}$ are each independently N or C, wherein at least one of $X_{51}$ and $X_{54}$ is N, $X_2$ is N, $X_{52a}$ and $X_{53a}$ are each independently N or C(R'), ring $CY_1$ to ring $CY_4$ are each independently selected from a $C_5$-$C_{30}$ carbocyclic group and a $C_1$-$C_{30}$ heterocyclic group, ring $CY_5$ is a $C_1$-$C_3$ heterocyclic group, in Formula 1, $X_5$ to $X_8$ are each independently selected from a single bond, O, S, B($R_5$), N($R_5$), P($R_5$), C($R_5$)($R_6$), Si($R_5$)($R_6$), Ge($R_5$)($R_6$), C(=O), B($R_5$)($R_6$), N($R_5$)($R_6$), or P($R_5$)($R_6$), $T_1$, $T_3$, and $T_4$ are each independently selected from a single bond, a double bond, *—N($R_7$)—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—O—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', and * and *' each indicate a binding site to a neighboring atom, $T_2$ is selected from a single bond, a double bond, *—N($R_7$)—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', and * and *' each indicate a binding site to a neighboring atom, at least one of $T_1$ to $T_4$ is a direct C≡C bond, $R_7$ and $R_8$ are optionally linked via a single bond, a double bond, or a first linking group to form a substituted or unsubstituted $C_5$-$C_{30}$ carbocyclic group or a substituted or unsubstituted $C_1$-$C_{30}$ heterocyclic group, provided that $T_2$ is a single bond when ring $CY_1$ is a six-membered ring, n is 0 or 1, wherein, when n is 0, $T_4$ does not exist and $CY_1$ and $CY_4$ are not linked, $R_1$ to $R_8$ and R' are each independently selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_3$)($Q_4$)($Q_5$), —B($Q_6$)($Q_7$), and —P(=O)($Q_8$)($Q_9$), a1 to a4 are each independently 0, 1, 2, 3, 4, or 5, at least two neighboring groups selected from $R_1$ to $R_8$ and R' are optionally linked to form a substituted or unsubstituted $C_5$-$C_{30}$ carbocyclic group or a substituted or unsubstituted $C_1$-$C_{30}$ heterocyclic group, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, Cl, —Br, —I, —CD$_3$, —CD$_2$H, —CDH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O) ($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_3$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ is heterocycloalkyl group, a $C_3$-$C_{10}$ cycloalkenyl group, a $C_1$-$C_{10}$ heterocycloalkenyl group, $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein M is Pd or Pt.

3. The organometallic compound of claim 1, wherein $X_5$, $X_7$, and $X_8$ are each independently a single bond, O, S, or N($R_5$), and $X_6$ is a single bond.

4. The organometallic compound of claim 1, wherein ring $CY_1$ to ring $CY_4$ are each independently selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a pyrrole group, a thiophene group, a furan group, an indole group, an isoindole group, a benzoborole group, a benzophosphole group, an indene group, a benzosilole group, a benzogermole group, a benzothiophene group, a benzoselenophene group, a benzofuran group, a carbazole group, a benzocarbazole group, a dibenzocarbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, an acridine group, a quinoxaline group, a quinazoline group, a phenanthroline group, a pyrazole group, an imidazole group, a triazole group, a tetrazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group.

5. The organometallic compound of claim 1, wherein $T_1$ is a single bond.

6. The organometallic compound of claim 1, wherein n is 0.

7. The organometallic compound of claim 1, wherein $R_1$ to $R_8$ and R' are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, and —Si(Q$_{33}$)(Q$_{34}$)(Q$_{35}$); and —N(Q$_1$)(Q$_2$), —Si(Q$_3$)(Q$_4$)(Q$_5$), —B(Q$_6$)(Q$_7$), and —P(=O)(Q$_8$)(Q$_9$), and Q$_1$ to Q$_9$ and Q$_{33}$ to Q$_{35}$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group.

8. The organometallic compound of claim 1, wherein R$_1$ to R$_8$ and R' are each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-22, groups represented by Formulae 10-1 to 10-143, and —Si(Q$_3$)(Q$_4$)(Q$_5$):

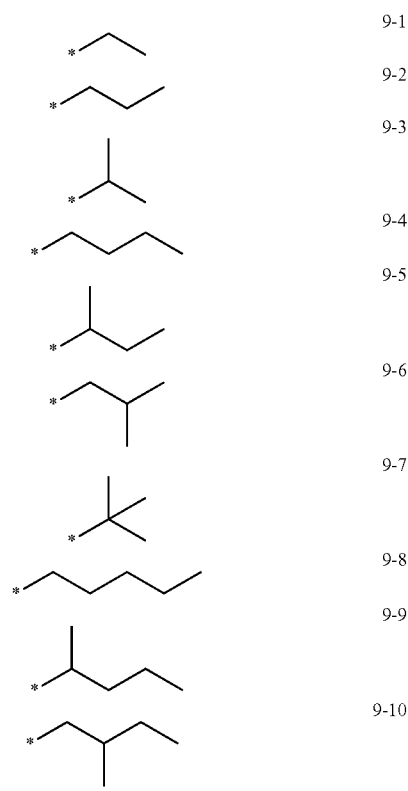

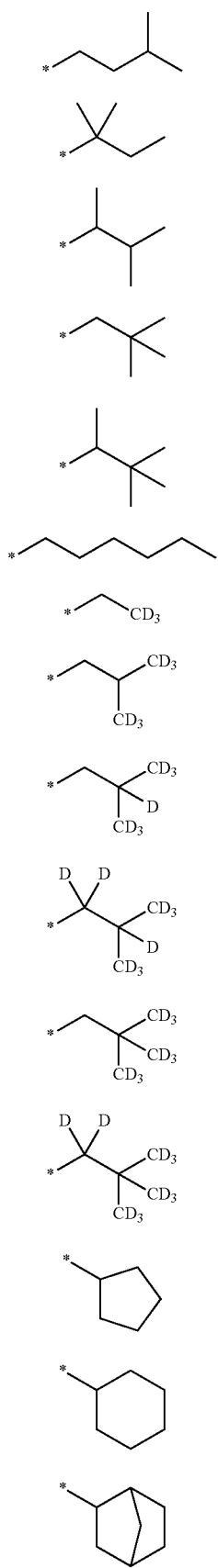
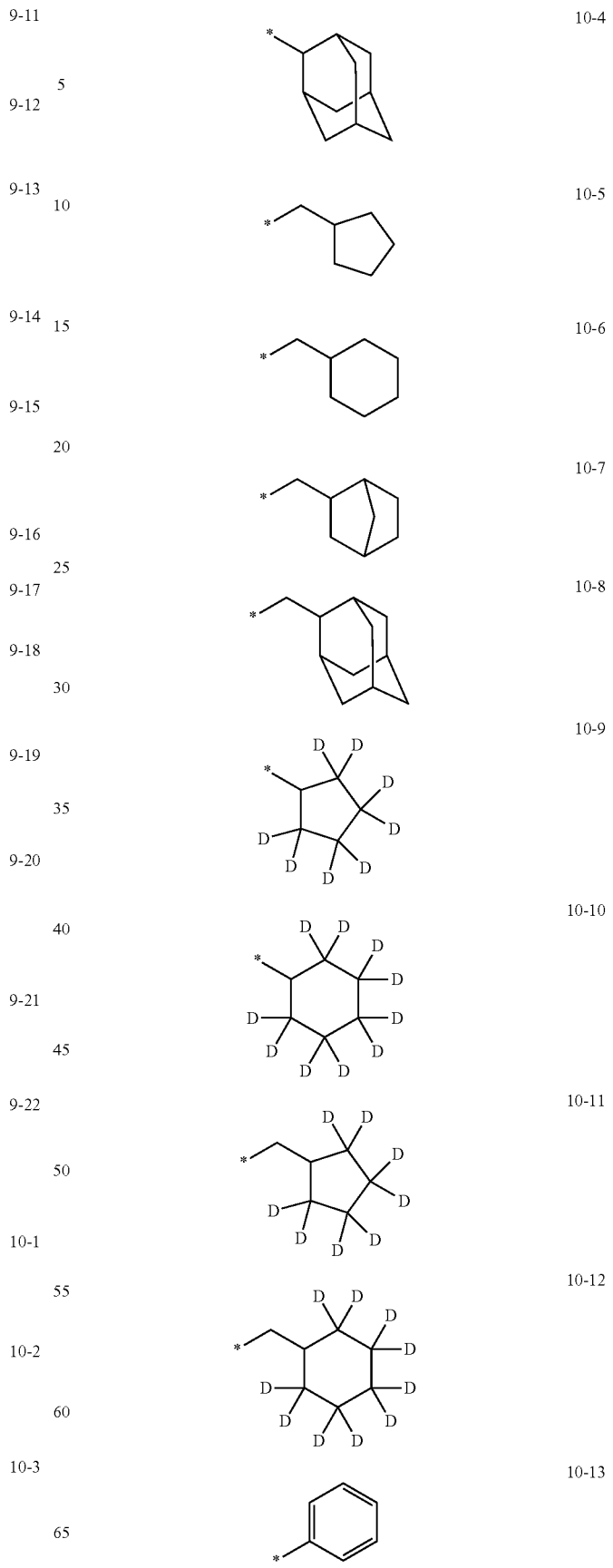

-continued
| | |
|---|---|
| 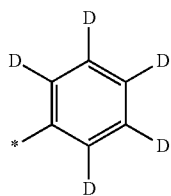 | 10-14 |
| 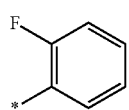 | 10-15 |
| 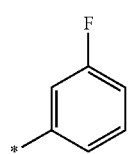 | 10-16 |
| 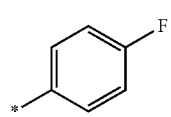 | 10-17 |
| 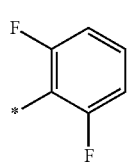 | 10-18 |
| 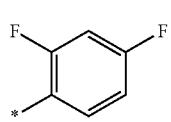 | 10-19 |
| 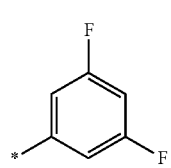 | 10-20 |
| 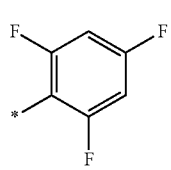 | 10-21 |
| 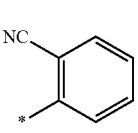 | 10-22 |
| 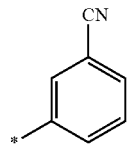 | 10-23 |
| 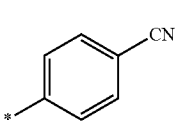 | 10-24 |
-continued
| | |
|---|---|
| 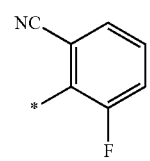 | 10-25 |
| 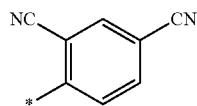 | 10-26 |
| 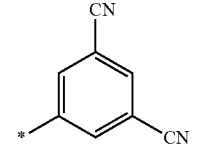 | 10-27 |
| 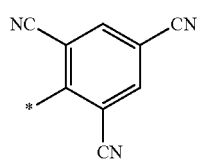 | 10-28 |
| 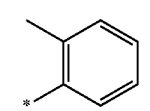 | 10-29 |
| 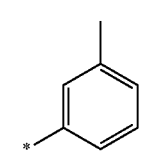 | 10-30 |
| 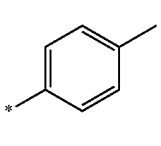 | 10-31 |
| 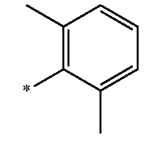 | 10-32 |
| 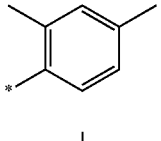 | 10-33 |
| 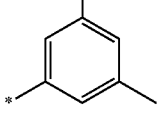 | 10-34 |
| 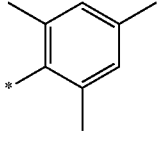 | 10-35 |

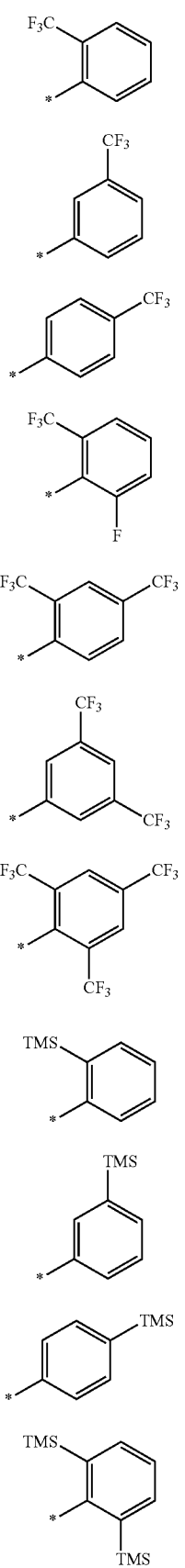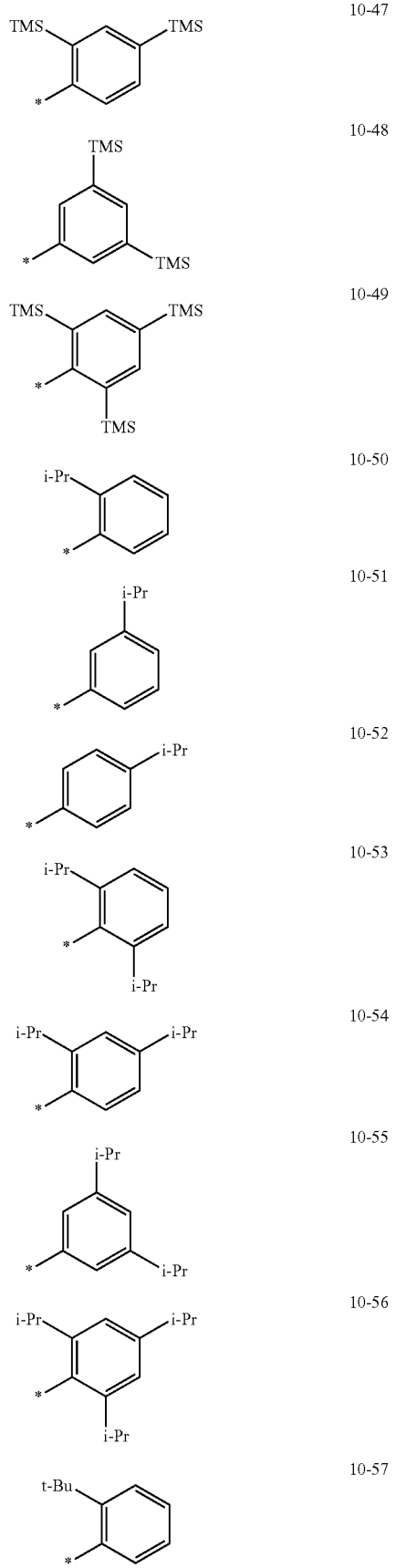

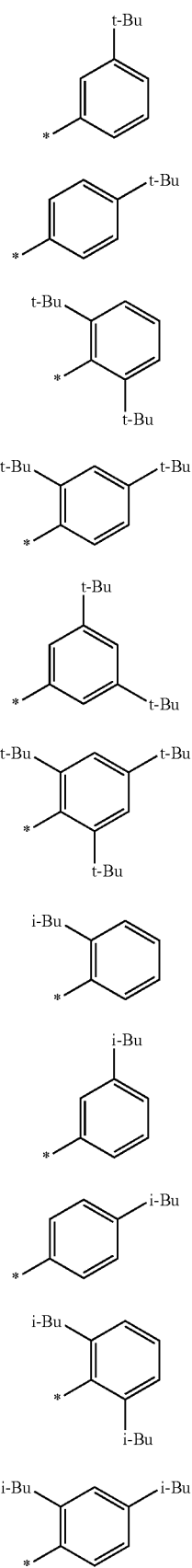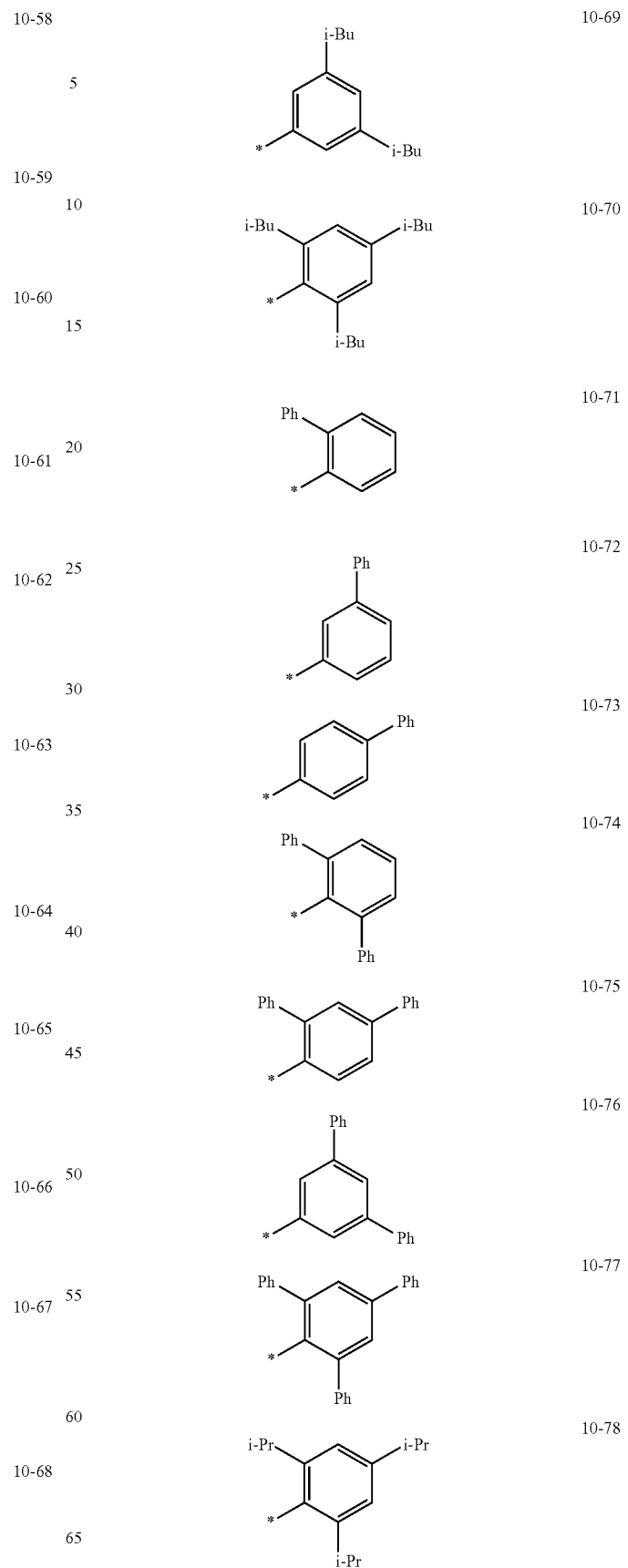

-continued
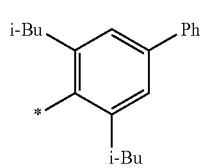 10-79
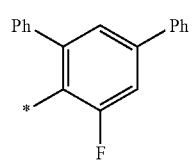 10-80
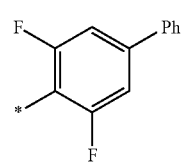 10-81
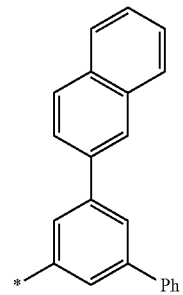 10-82
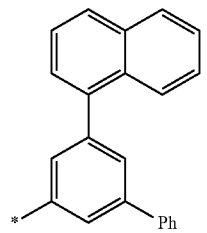 10-83
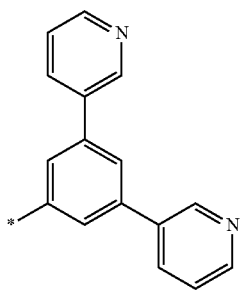 10-84
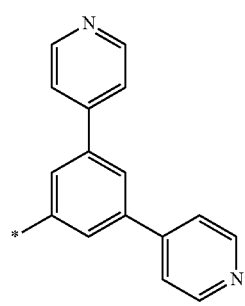 10-85
-continued
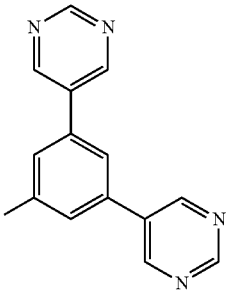 10-86
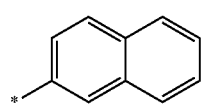 10-87
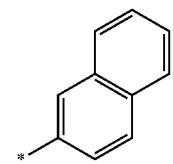 10-88
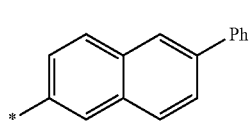 10-89
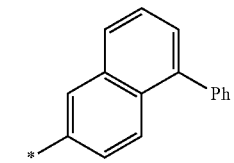 10-90
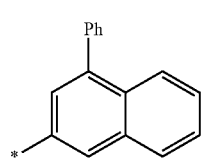 10-91
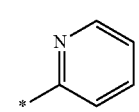 10-92
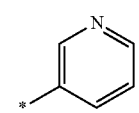 10-93
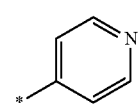 10-94
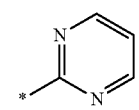 10-95
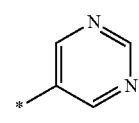 10-96

-continued
| | |
|---|---|
| 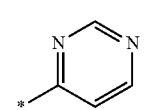 | 10-97 |
| 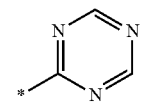 | 10-98 |
| 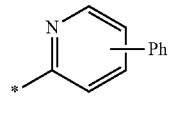 | 10-99 |
| 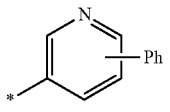 | 10-100 |
| 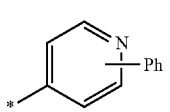 | 10-101 |
| 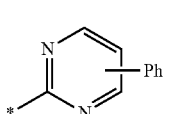 | 10-102 |
| 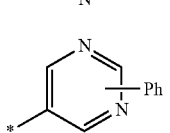 | 10-103 |
| 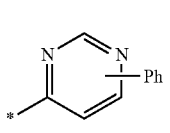 | 10-104 |
| 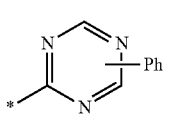 | 10-105 |
| 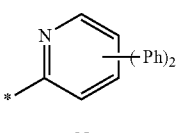 | 10-106 |
| 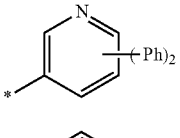 | 10-107 |
| 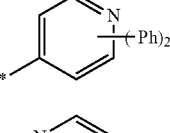 | 10-108 |
| 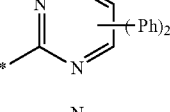 | 10-109 |
| 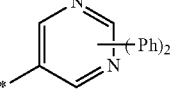 | 10-110 |
-continued
| | |
|---|---|
| 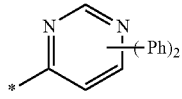 | 10-111 |
| 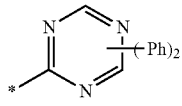 | 10-112 |
| 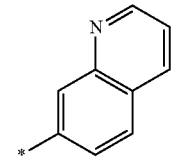 | 10-113 |
| 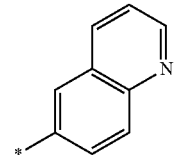 | 10-114 |
| 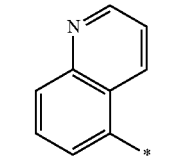 | 10-115 |
| 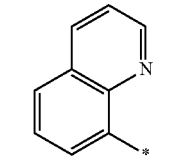 | 10-116 |
| 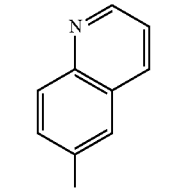 | 10-117 |
| 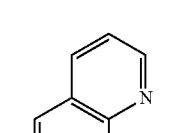 | 10-118 |
| 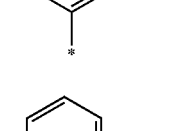 | 10-119 |

| | |
|---|---|
| 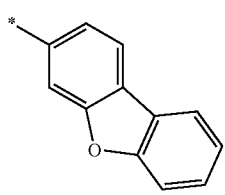 | 10-120 |
| 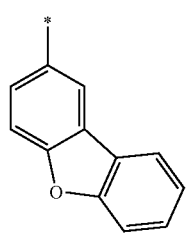 | 10-121 |
| 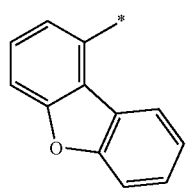 | 10-122 |
| 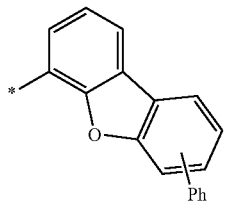 | 10-123 |
| 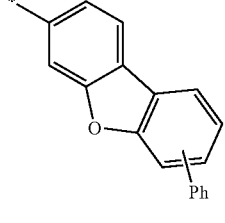 | 10-124 |
| 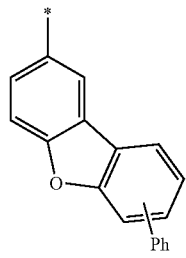 | 10-125 |
| 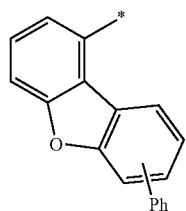 | 10-126 |
|  | 10-127 |
| 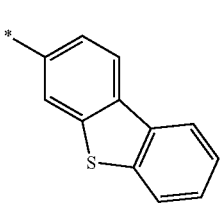 | 10-128 |
| 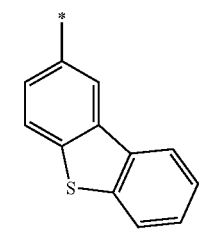 | 10-129 |
| 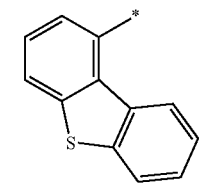 | 10-130 |
| 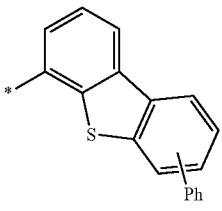 | 10-131 |
| 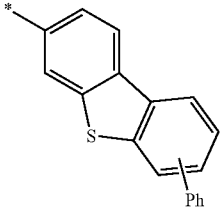 | 10-132 |
| 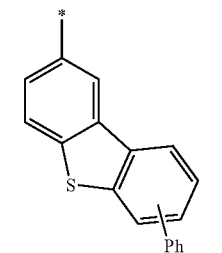 | 10-133 |

165
-continued 10-134
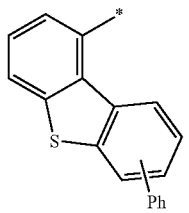

10-135
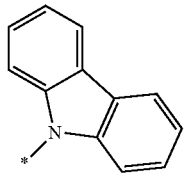

10-136
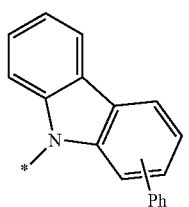

10-137
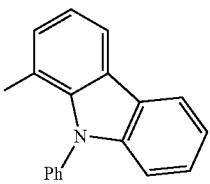

10-138
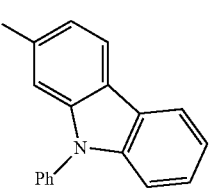

10-139
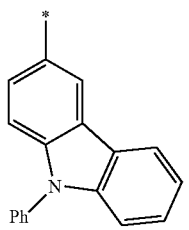

10-140
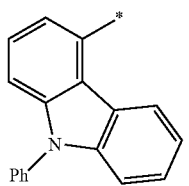

10-141
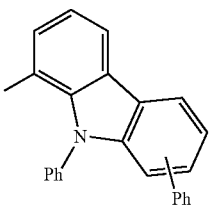

166
-continued 10-142
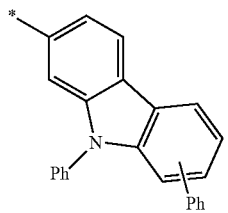

10-143
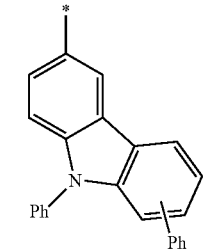

10-144
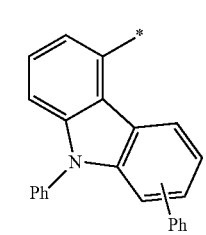

wherein, in Formulae 9-1 to 9-22 and 10-1 to 10-143, i-Pr indicates an iso-propyl group, i-Bu indicates an iso-butyl group, t-Bu indicates a tert-butyl group, TMS indicates a trimethylsilyl group, Ph indicates a phenyl group, and * indicates a binding site to a neighboring atom.

9. The organometallic compound of claim 1, wherein
n is 0, and $A_1$ is represented by one selected from Formulae CY1-1 to CY1-34, or
n is 1, and $A_1$ is represented by one selected from Formulae CY1-101 to CY1-123:

CY1-1
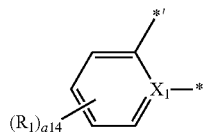

CY1-2
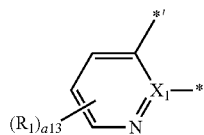

CY1-3
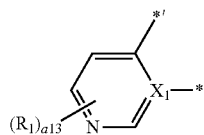

CY1-4
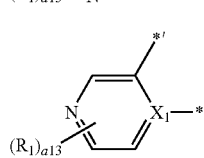

CY1-5
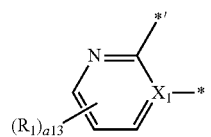
CY1-6
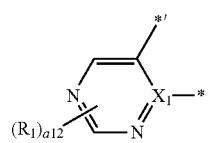
CY1-7
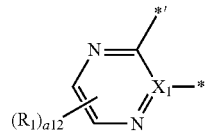
CY1-8
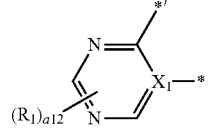
CY1-9
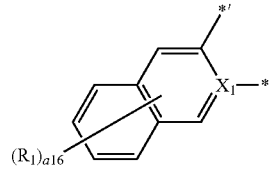
CY1-10
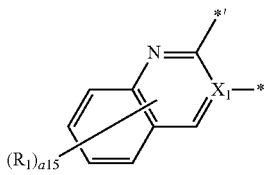
CY1-11
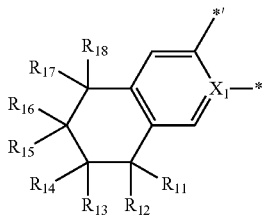
CY1-12
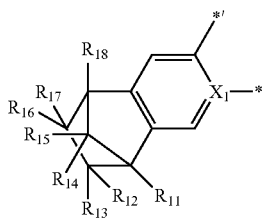
CY1-13
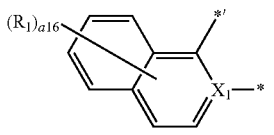
CY1-14
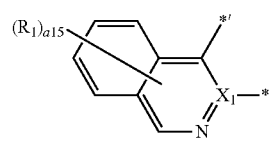
CY1-15
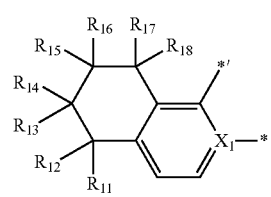
CY1-16
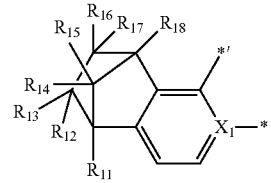
CY1-17
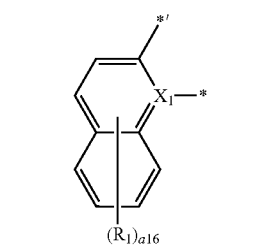
CY1-18
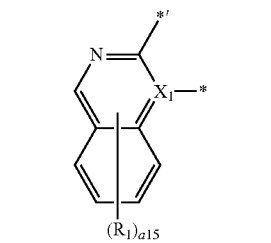
CY1-19
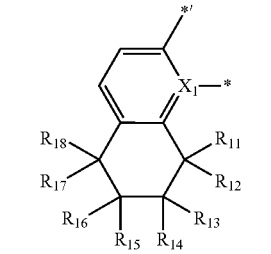
CY1-20
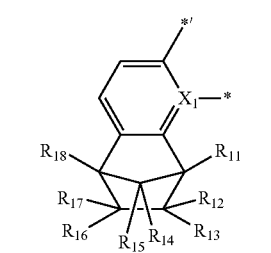

-continued
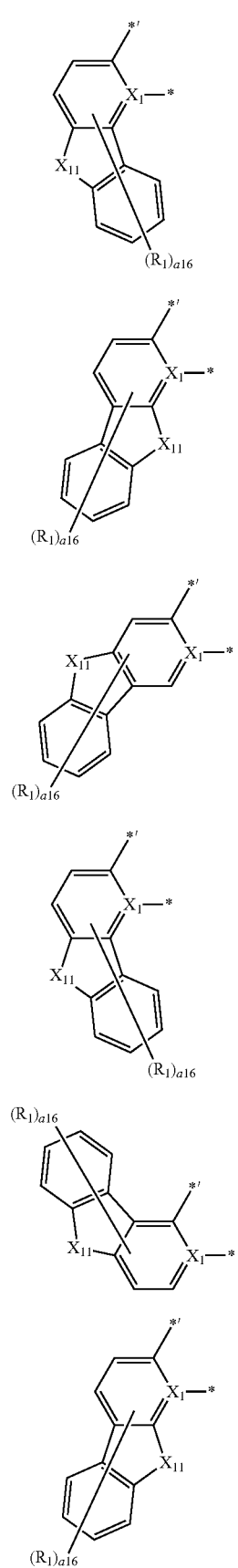
CY1-21
CY1-22
CY1-23
CY1-24
CY1-25
CY1-26
-continued
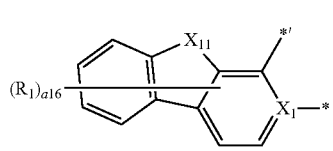
CY1-27
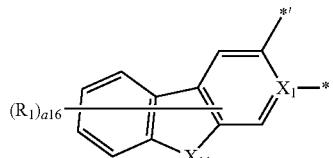
CY1-28
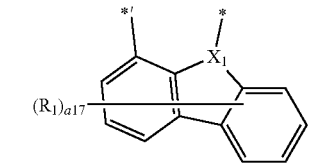
CY1-29
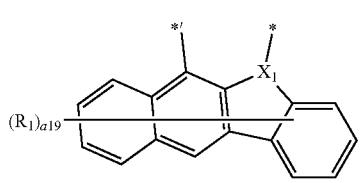
CY1-30
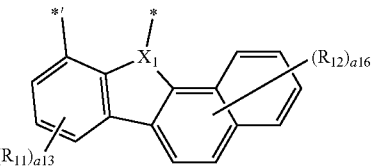
CY1-31
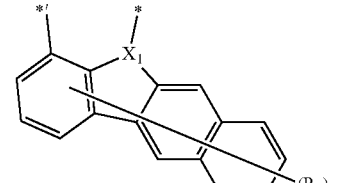
CY1-32
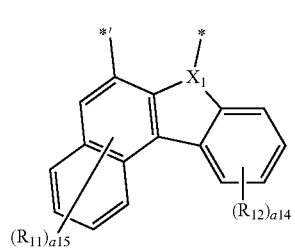
CY1-33
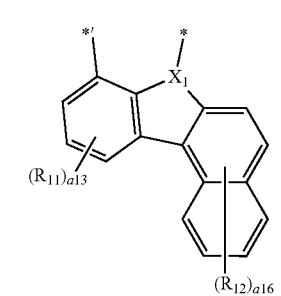
CY1-34

-continued
CY1-101
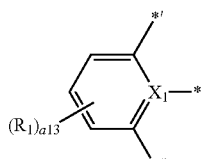
CY1-102
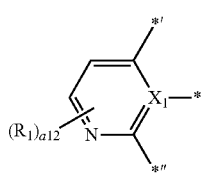
CY1-103
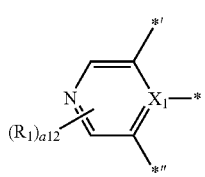
CY1-104
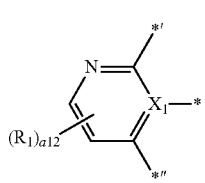
CY1-105
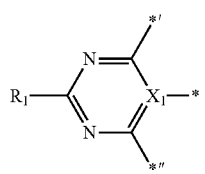
CY1-106
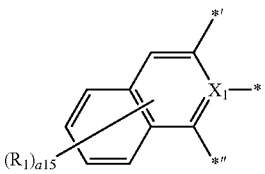
CY1-107
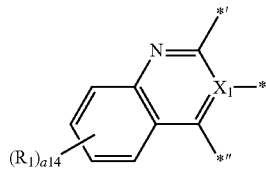
CY1-108
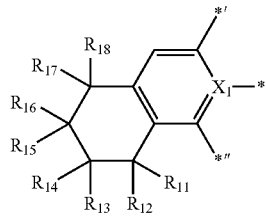
-continued
CY1-109
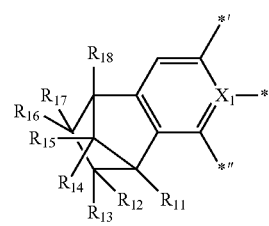
CY1-110
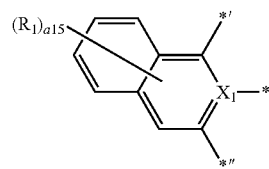
CY1-111
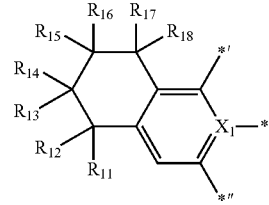
CY1-112
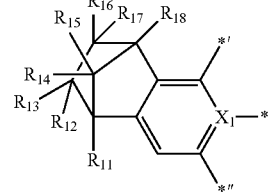
CY1-113
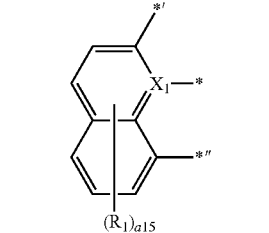
CY1-114
CY1-115
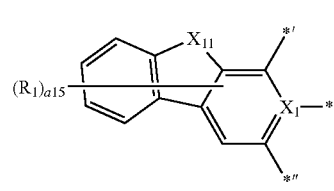

CY1-116
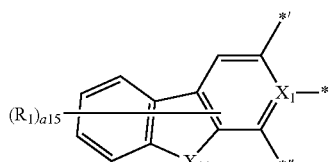

CY1-117
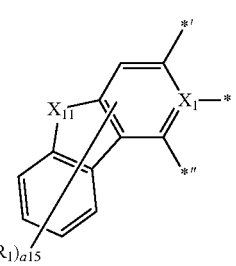

CY1-118
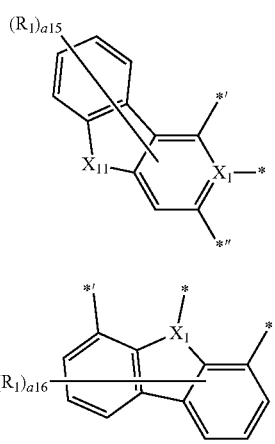

CY1-119
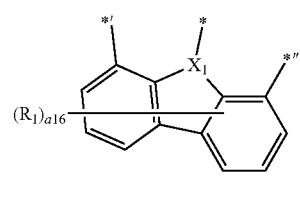

CY1-120
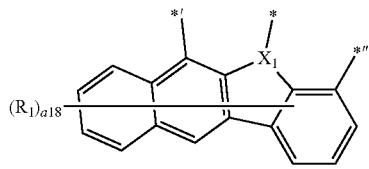

CY1-121
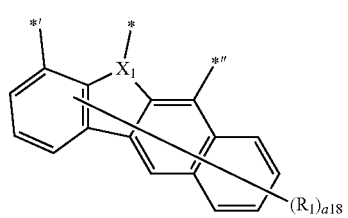

CY1-122
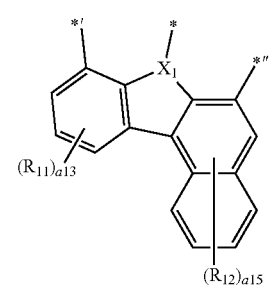

CY1-123
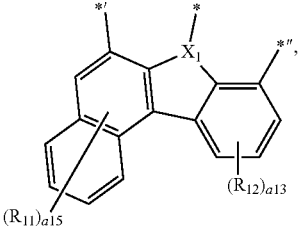

wherein, in Formulae CY1-1 to CY1-34 and CY1-101 to CY1-123, $X_1$ and $R_1$ are each independently the same as described in claim 1, $X_{11}$ is O, S, N($R_{11}$), C($R_{11}$)($R_{12}$), or Si($R_{11}$)($R_{12}$), $R_{11}$ to $R_{18}$ are each independently the same as described in connection with $R_1$ in claim 1, a19 is an integer from 0 to 9,
a18 is an integer from 0 to 8,
a17 is an integer from 0 to 7,
a16 is an integer from 0 to 6,
a15 is an integer from 0 to 5,
a14 is an integer from 0 to 4,
a13 is an integer from 0 to 3,
a12 is an integer from 0 to 2, \* indicates a binding site to $X_5$ in Formula 1,
\*' indicates a binding site to $T_1$ in Formula 1, and
\*'' indicates a binding site to $T_4$ in Formula 1.

10. The organometallic compound of claim 1, wherein $A_2$ is represented by one selected from Formulae CZ-1 to CZ-20:

CZ-1
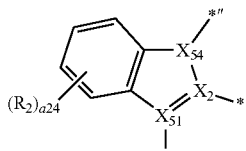

CZ-2
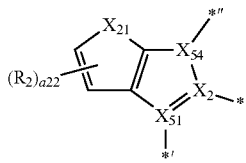

CZ-3
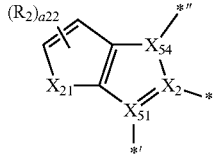

CZ-4
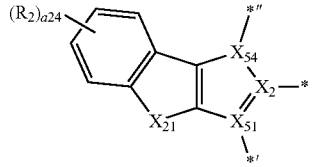

CZ-5 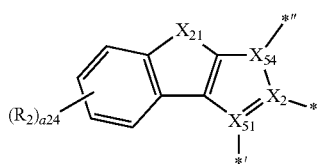
CZ-6 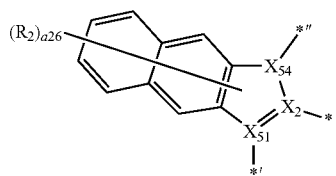
CZ-7 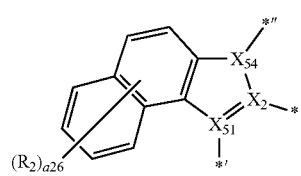
CZ-8 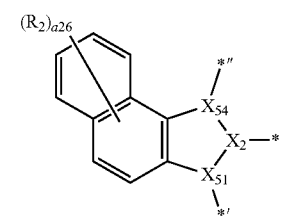
CZ-9 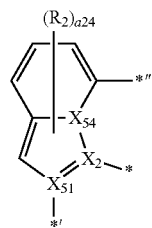
CZ-10 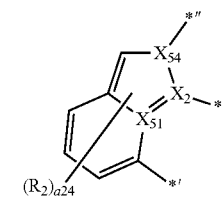
CZ-11 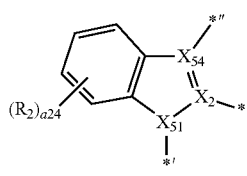
CZ-12 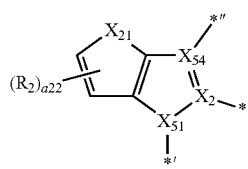
CZ-13 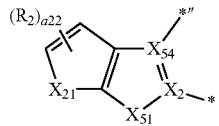
CZ-14 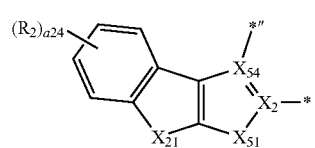
CZ-15 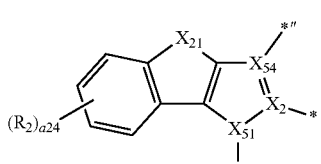
CZ-16 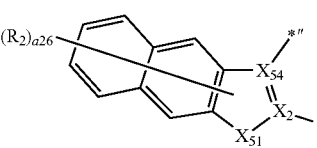
CZ-17 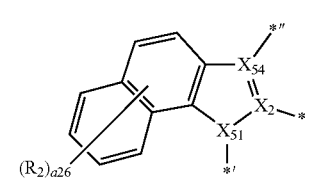
CZ-18 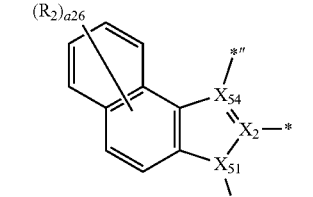
CZ-19 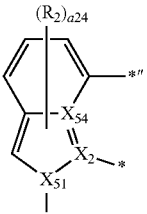
CZ-20 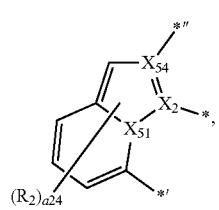
wherein, in Formulae CZ-1 to CZ-20,
$X_2$, $X_{51}$, $X_{54}$, and $R_2$ are each independently the same as described in claim 1,
$X_{21}$ is O, S, N($R_{21}$), C($R_{21}$)($R_{22}$), or Si($R_{21}$)($R_{22}$), $R_{21}$ and $R_{22}$ are each independently defined the same as $R_2$ in claim 1, a26 is an integer from 0 to 6, a24 is an integer from 0 to 4, a22 is an integer from 0 to 2,

* indicates a binding site to $X_6$ in Formula 1,

*' indicates a binding site to $T_1$ in Formula 1, and

*'' indicates a binding site to $T_2$ in Formula 1.

11. The organometallic compound of claim 1, wherein $A_3$ is represented by one selected from Formulae CY3-1 to CY3-40:

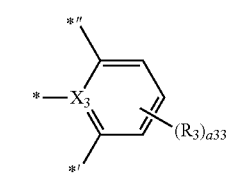

CY3-1

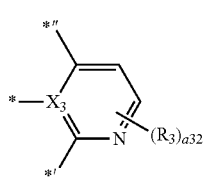

CY3-2

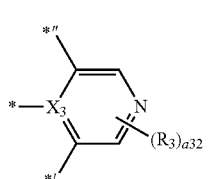

CY3-3

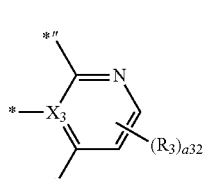

CY3-4

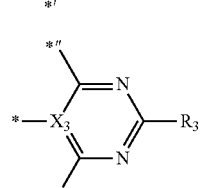

CY3-5

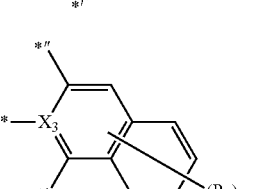

CY3-6

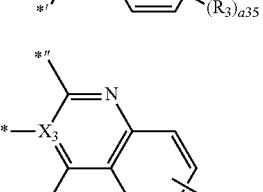

CY3-7

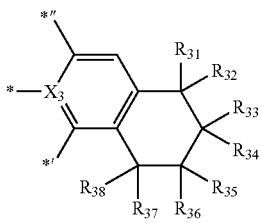

CY3-8

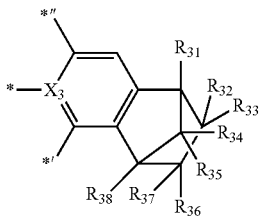

CY3-9

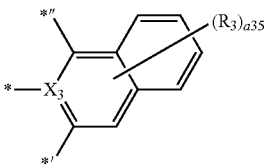

CY3-10

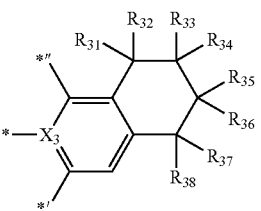

CY3-11

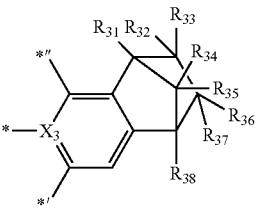

CY3-12

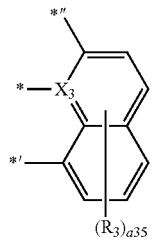

CY3-13

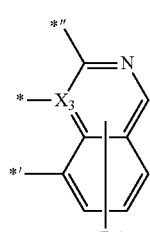

CY3-14

-continued
CY3-15
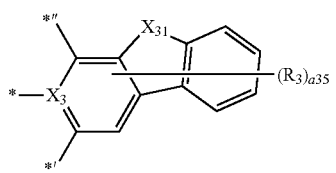
CY3-16
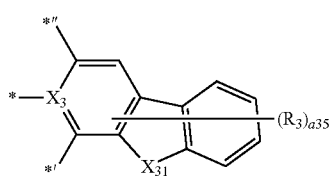
CY3-17
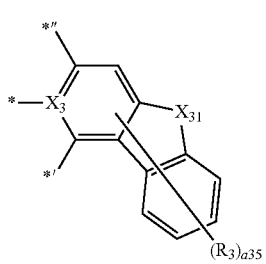
CY3-18
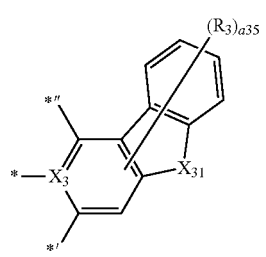
CY3-19
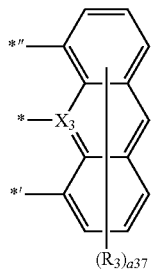
CY3-20
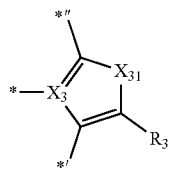
CY3-21
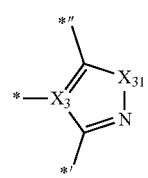
-continued
CY3-22
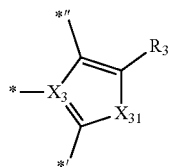
CY3-23
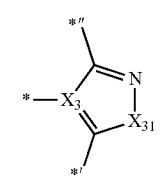
CY3-24
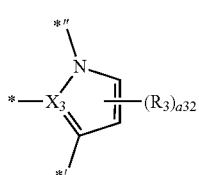
CY3-25
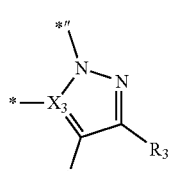
CY3-26
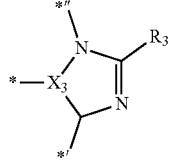
CY3-27
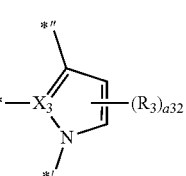
CY3-28
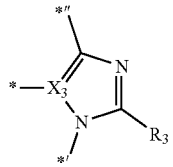
CY3-29
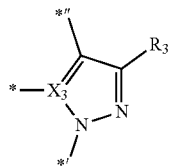
CY3-30
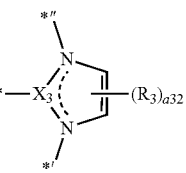

CY3-31 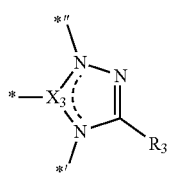

CY3-32 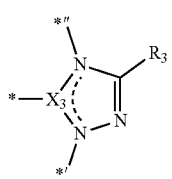

CY3-33 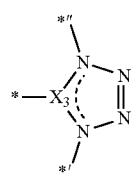

CY3-34 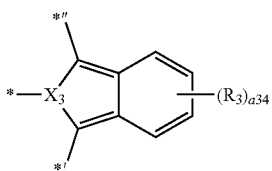

CY3-35 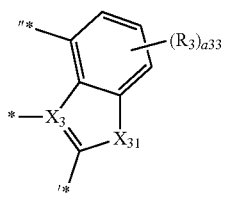

CY3-36 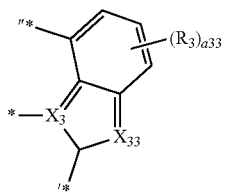

CY3-37 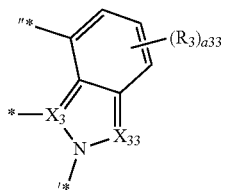

CY3-38 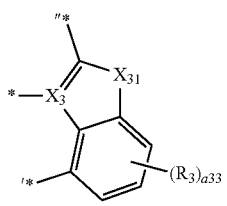

CY3-39 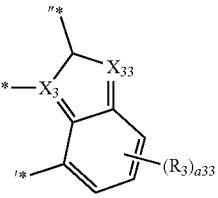

CY3-40 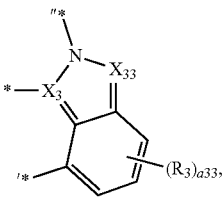

wherein, in Formulae CY3-1 to CY3-40, $X_3$ and $R_3$ are each independently the same as described in claim 1, $X_{31}$ is O, S, N($R_{31}$), C($R_{31}$)($R_{32}$), or Si($R_{31}$)($R_{32}$), $X_{33}$ is N or C($R_{31}$), $R_{31}$ to $R_{38}$ are each independently defined the same as $R_3$ in claim 1, a37 is an integer from 0 to 7, a35 is an integer from 0 to 5, a34 is an integer from 0 to 4, a33 is an integer from 0 to 3, a32 is an integer from 0 to 2, \* indicates a binding site to $X_7$ in Formula 1, \*″ indicates a binding site to $T_2$ in Formula 1, and \*′ indicates a binding site to $T_3$ in Formula 1.

12. The organometallic compound of claim 1, wherein i) $A_4$ is \*—O—\*′ or \*—S—\*′, and $T_3$ is a single bond, \*—N($R_7$)—\*′, \*—B($R_7$)—\*′, \*—P($R_7$)—\*′, \*—C($R_7$)($R_8$)—\*′, \*—Si($R_7$)($R_8$)—\*′, \*—Ge($R_7$)($R_8$)—\*′, or \*—C(=O)—\*′, ii) $A_4$ is represented by one selected from Formulae A4(1) to A4(6), and $T_3$ is a single bond, iii) n is 0, and $A_4$ is represented by one selected from Formulae CY4-1 to CY4-35, or iv) n is 1, and $A_4$ is represented by one selected from Formulae CY4-101 to CY4-124:

A4(1) 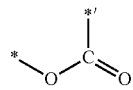

A4(2) 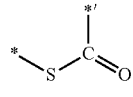

A4(3) 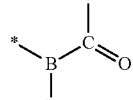

A4(4) 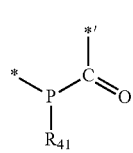

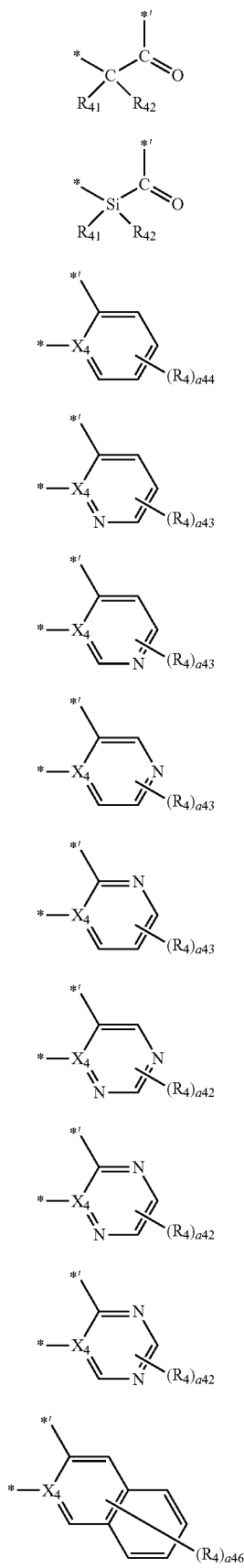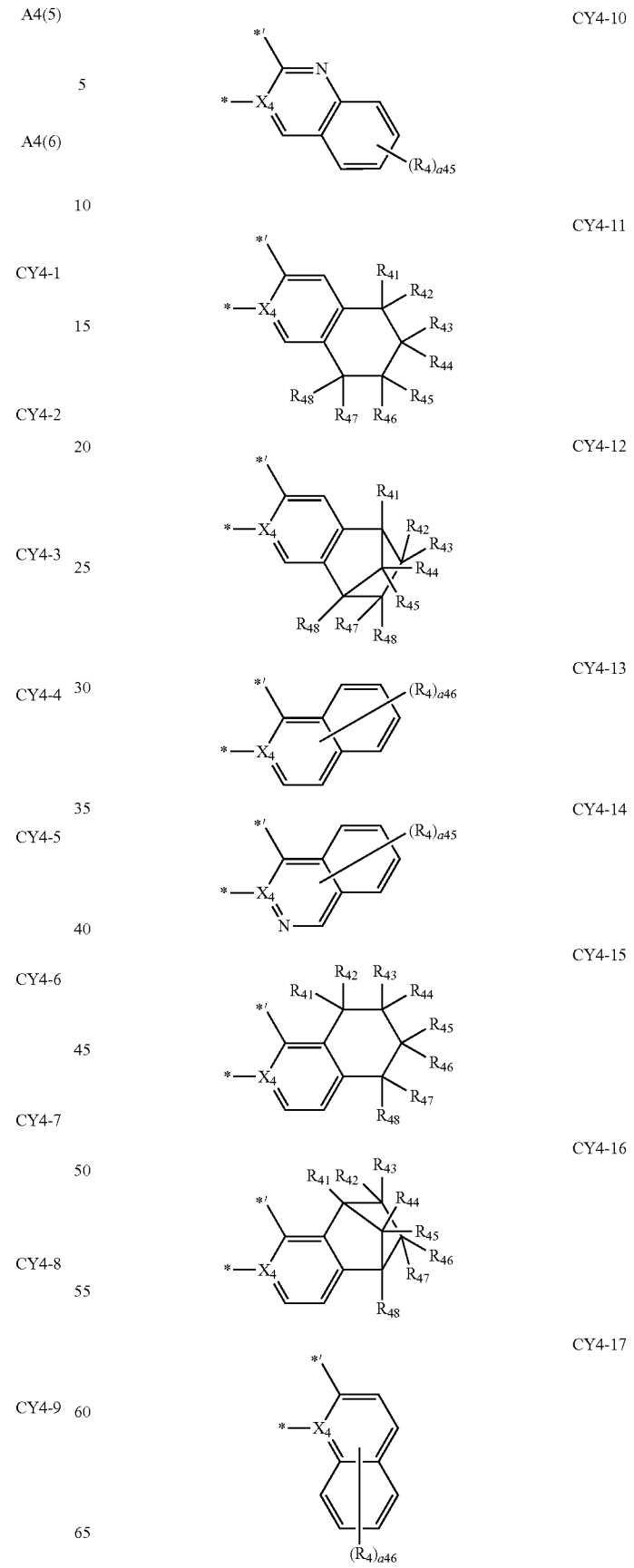

CY4-18
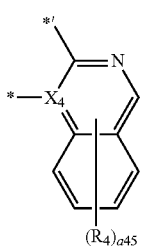
CY4-19
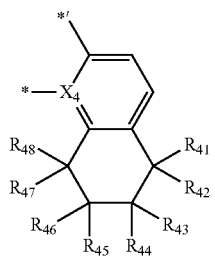
CY4-20
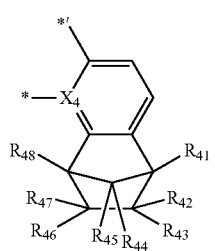
CY4-21
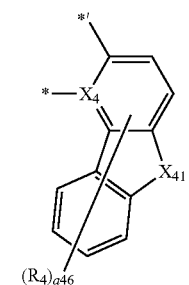
CY4-22
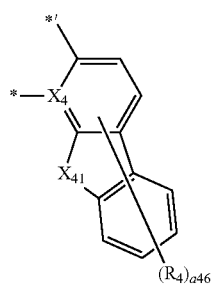
CY4-23
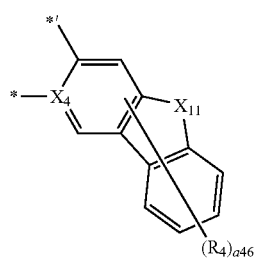
CY4-24
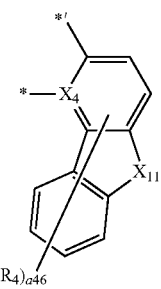
CY4-25
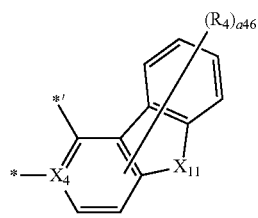
CY4-26
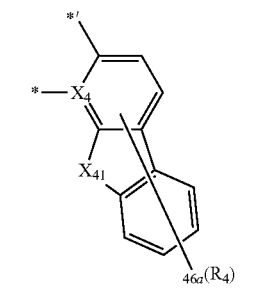
CY4-27
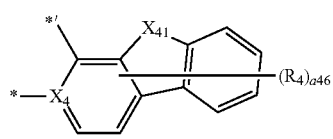
CY4-28
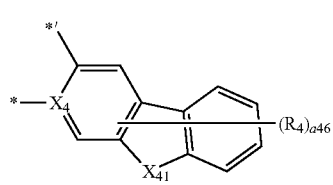
CY4-29
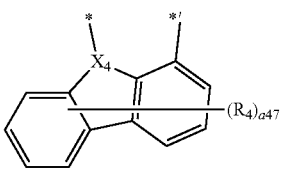
CY4-30
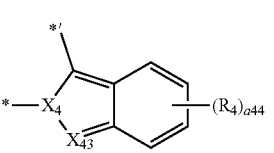
CY4-31
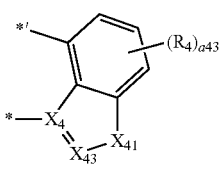

CY4-32 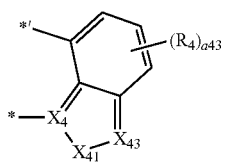
CY4-33 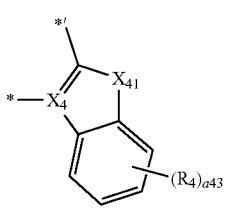
CY4-34 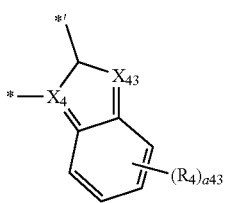
CY4-35 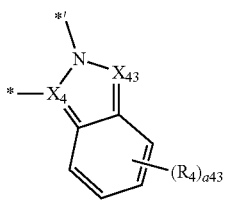
CY4-101 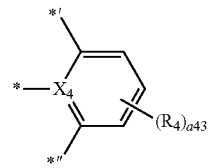
CY4-102 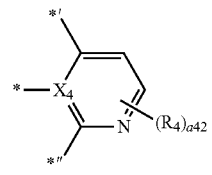
CY4-103 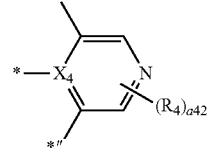
CY4-104 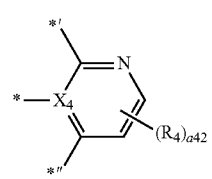
CY4-105 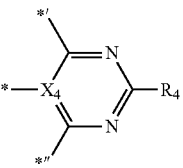
CY4-106 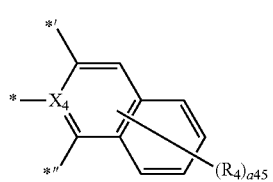
CY4-107 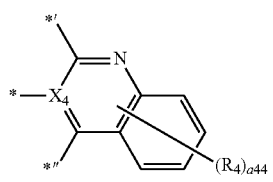
CY4-108 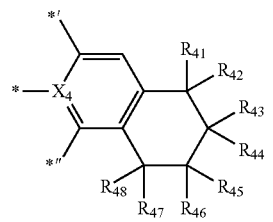
CY4-109 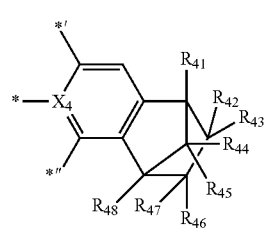
CY4-110 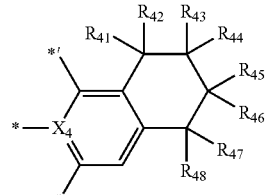
CY4-111 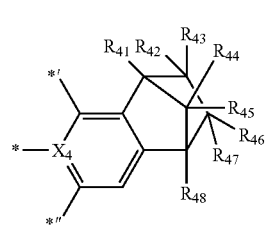

wherein, in Formulae A4(1) to A4(5), CY4-1 to CY4-35, and CY4-101 to CY4-124, $X_4$ and $R_4$ are each independently the same as described in claim 1, $X_{41}$ is O, S, N($R_{41}$), C($R_{41}$)($R_{42}$), or Si($R_{41}$)($R_{42}$), $X_{43}$ is N or C($R_{41}$), $R_{41}$ to $R_{48}$ are each independently defined the same as $R_4$ in claim 1, a47 is an integer from 0 to 7,
a46 is an integer from 0 to 6,
a45 is an integer from 0 to 5,
a44 is an integer from 0 to 4,
a43 is an integer from 0 to 3,
a42 is an integer from 0 to 2,

* indicates a binding site to $X_8$ in Formula 1,
*' indicates a binding site to $T_3$ in Formula 1, and
*" indicates a binding site to $T_4$ in Formula 1.

13. The organometallic compound of claim 1, wherein n is 0, and a moiety represented by

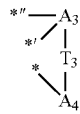

in Formula 1 is represented by Formula CY34-1, or n is 1, and a moiety represented by

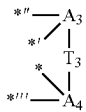

in Formula 1 is represented by Formula CY34-2:

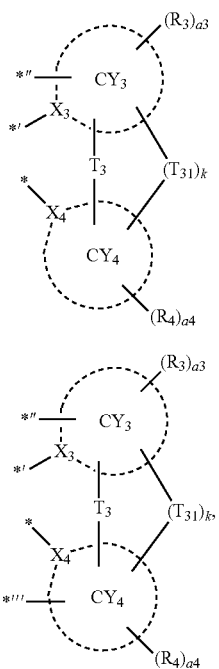

Formula CY34-1

Formula CY34-2 wherein, in Formulae CY34-1 and CY34-2,
$X_3$, $X_4$, $T_3$, $R_3$, $R_4$, a3, and a4 are each independently the same as described in claim 1, $T_{31}$ is a single bond, O, S, $N(R_{41})$, $C(R_{41})(R_{42})$, or $Si(R_{41})(R_{42})$,
k is 0, 1, 2, 3, 4, or 5, wherein, when k is 0, $T_{31}$ does not exist, and when k is two or more, two or more groups $T_{31}$ are identical to or different from each other,
$R_{41}$ and $R_{42}$ are each independently defined the same as $R_4$ in claim 1,
* indicates a binding site to $X_7$ in Formula 1,
*' indicates a binding site to $X_8$ in Formula 1,
*'' indicates a binding site to $T_2$ in Formula 1, and
*''' indicates a binding site to $T_4$ in Formula 1.

14. The organometallic compound of claim 1, wherein n is 0, and $A_1$ is represented by one selected from Formulae CY1(1) to CY1(24); or n is 1, and $A_1$ is represented by one selected from Formulae CY1(101) to CY1(116), $A_2$ is represented by one selected from Formulae CZ(1) to CZ(24),
$A_3$ is represented by one selected from Formulae CY3(1) to CY3(14), and
n is 0, and $A_4$ is represented by one selected from Formulae CY4(1) to CY4(13); or n is 1, and $A_4$ is represented by one selected from Formulae CY4(101) to CY4(110):

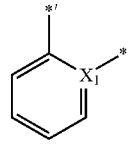

CY1(1)

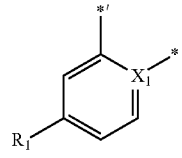

CY1(2)

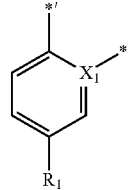

CY1(3)

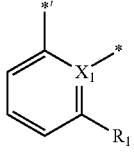

CY1(4)

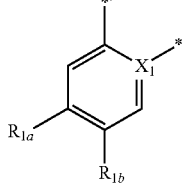

CY1(5)

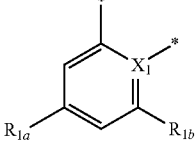

CY1(6)

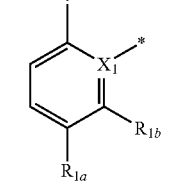

CY1(7)

-continued
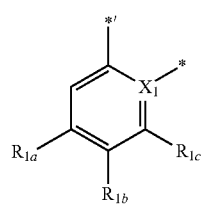 CY1(8)
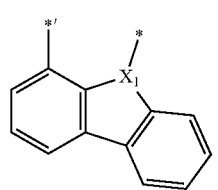 CY1(9)
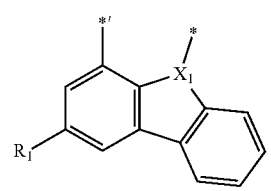 CY1(10)
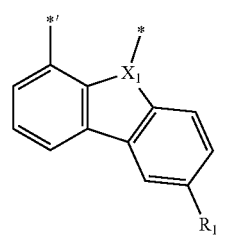 CY1(11)
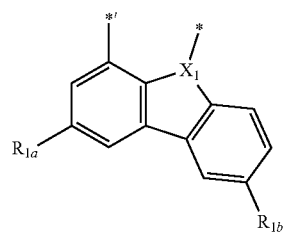 CY1(12)
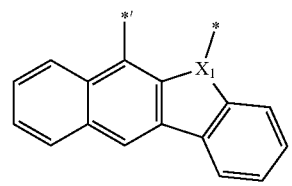 CY1(13)
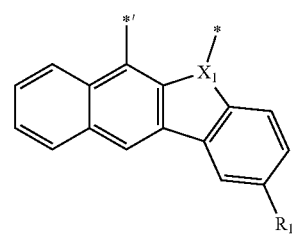 CY1(14)
-continued
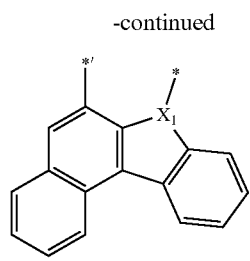 CY1(15)
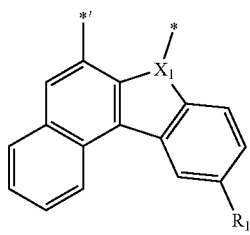 CY1(16)
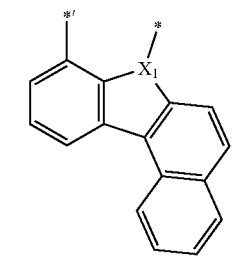 CY1(17)
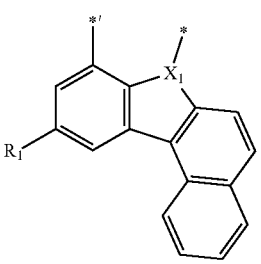 CY1(18)
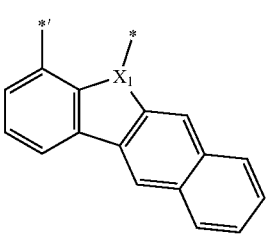 CY1(19)
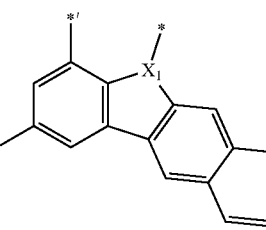 CY1(20)
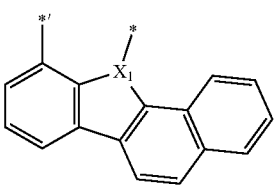 CY1(21)

CY1(22)
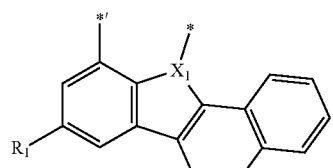
CY1(23)
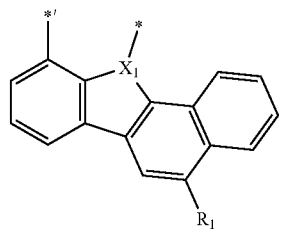
CY1(24)
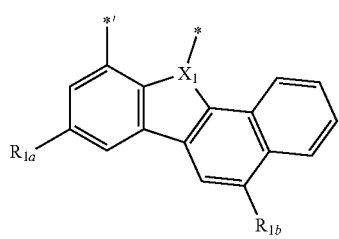
CY1(101)
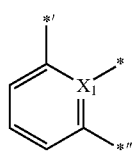
CY1(102)
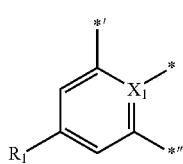
CY1(103)
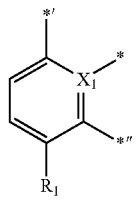
CY1(104)
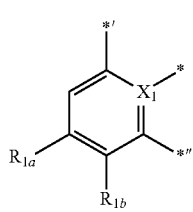
CY1(105)
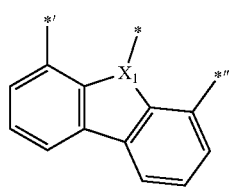
CY1(106)
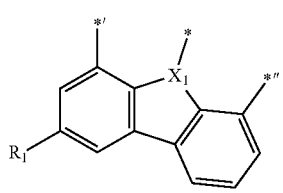
CY1(107)
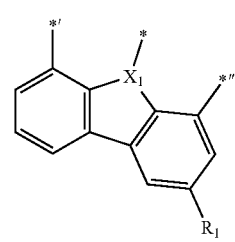
CY1(108)
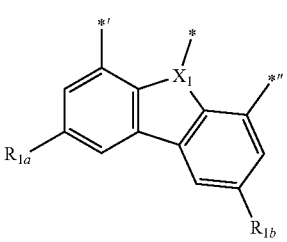
CY1(109)
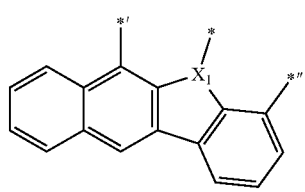
CY1(110)
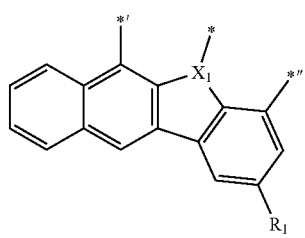
CY1(111)
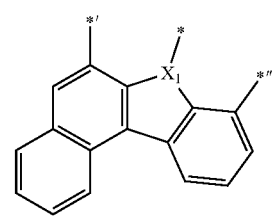
CY1(112)
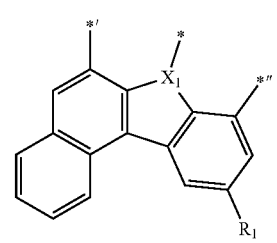

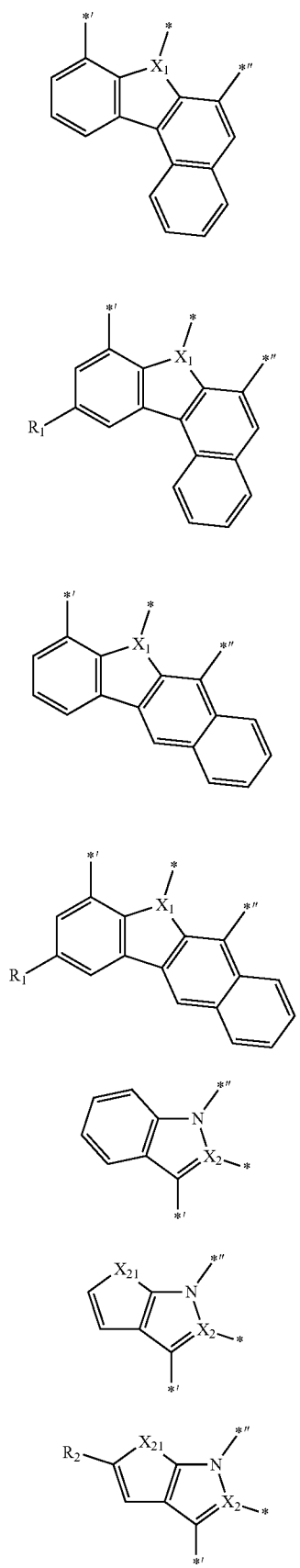

-continued
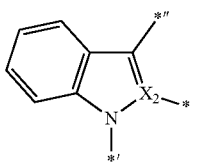 CZ(13)
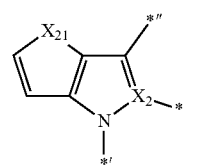 CZ(14)
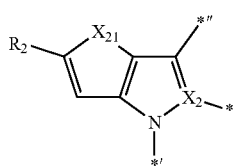 CZ(15)
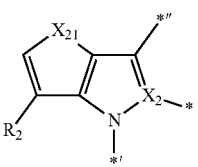 CZ(16)
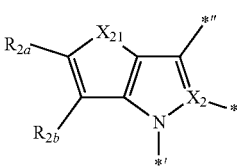 CZ(17)
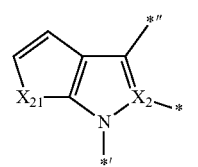 CZ(18)
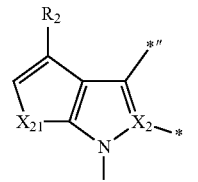 CZ(19)
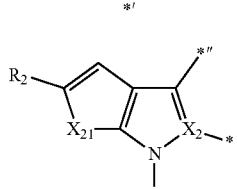 CZ(20)
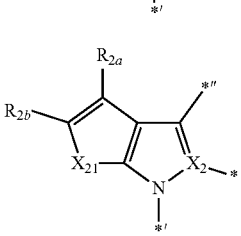 CZ(21)
-continued
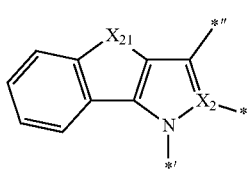 CZ(22)
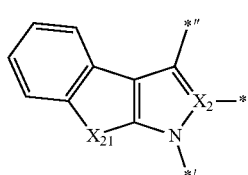 CZ(23)
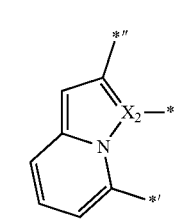 CZ(24)
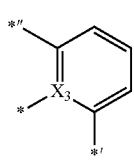 CY3(1)
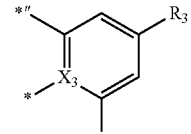 CY3(2)
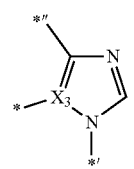 CY3(3)
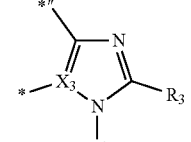 CY3(4)
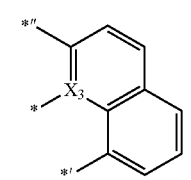 CY3(5)
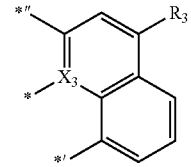 CY3(6)

-continued
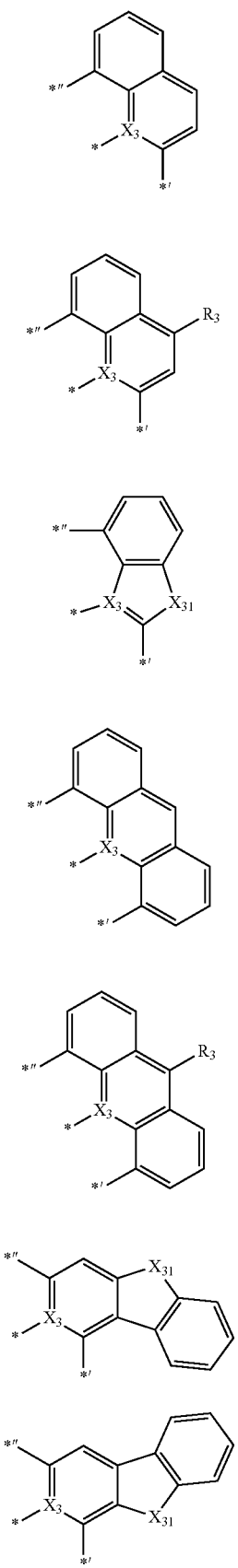
CY3(7)
CY3(8)
CY3(9)
CY3(10)
CY3(11)
CY3(12)
CY3(13)
-continued
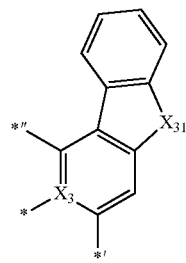
CY3(14)
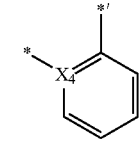
CY4(1)
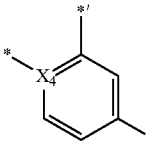
CY4(2)
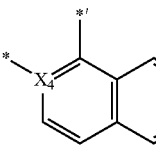
CY4(3)
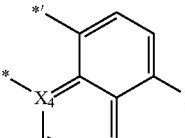
CY4(4)
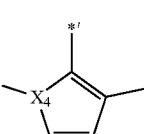
CY4(5)
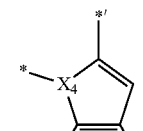
CY4(6)
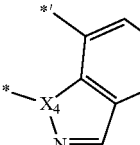
CY4(7)
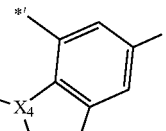
CY4(8)

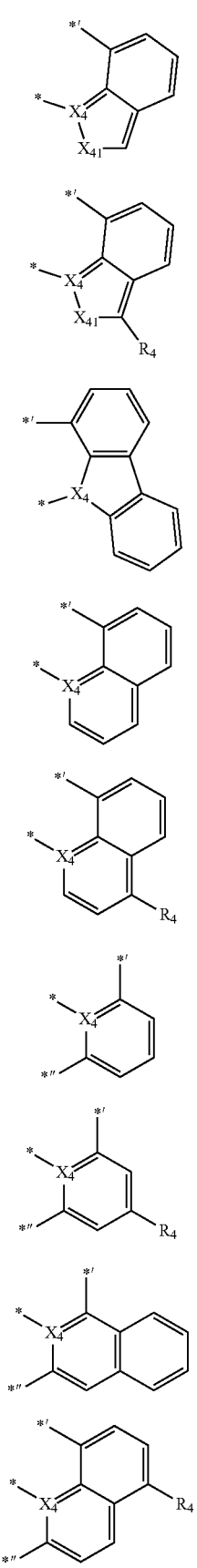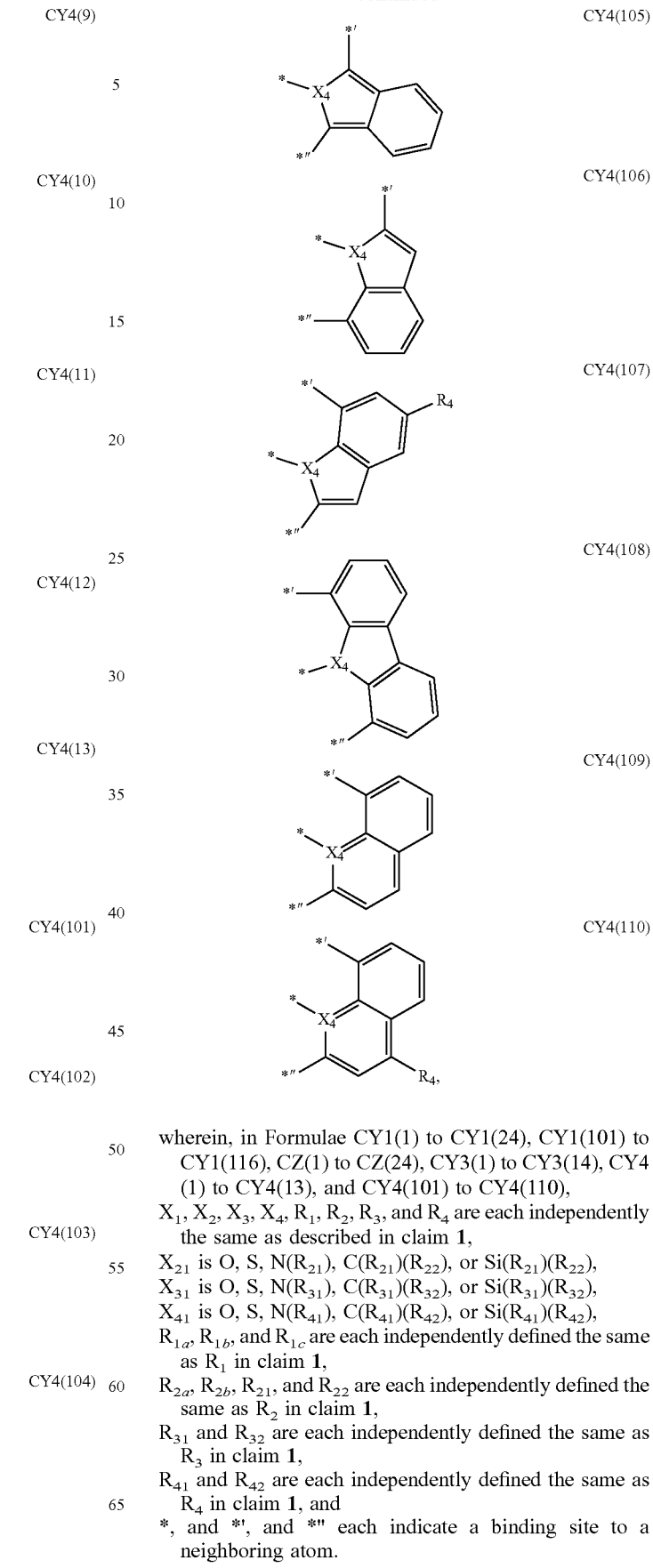

wherein, in Formulae CY1(1) to CY1(24), CY1(101) to CY1(116), CZ(1) to CZ(24), CY3(1) to CY3(14), CY4(1) to CY4(13), and CY4(101) to CY4(110), $X_1$, $X_2$, $X_3$, $X_4$, $R_1$, $R_2$, $R_3$, and $R_4$ are each independently the same as described in claim 1, $X_{21}$ is O, S, $N(R_{21})$, $C(R_{21})(R_{22})$, or $Si(R_{21})(R_{22})$, $X_{31}$ is O, S, $N(R_{31})$, $C(R_{31})(R_{32})$, or $Si(R_{31})(R_{32})$, $X_{41}$ is O, S, $N(R_{41})$, $C(R_{41})(R_{42})$, or $Si(R_{41})(R_{42})$, $R_{1a}$, $R_{1b}$, and $R_{1c}$ are each independently defined the same as $R_1$ in claim 1, $R_{2a}$, $R_{2b}$, $R_{21}$, and $R_{22}$ are each independently defined the same as $R_2$ in claim 1, $R_{31}$ and $R_{32}$ are each independently defined the same as $R_3$ in claim 1, $R_{41}$ and $R_{42}$ are each independently defined the same as $R_4$ in claim 1, and

*, and *', and *" each indicate a binding site to a neighboring atom.

15. The organometallic compound of claim 1, wherein the organometallic compound is selected from Compounds 1, 3-11, 13, 15-37, 39-40, 43-51, 53-54, 58, 60-86, and 88:
1
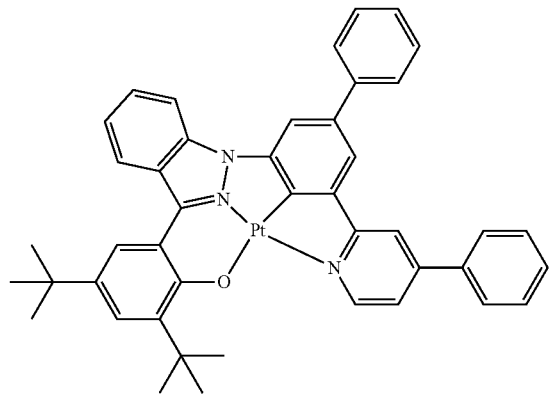
3
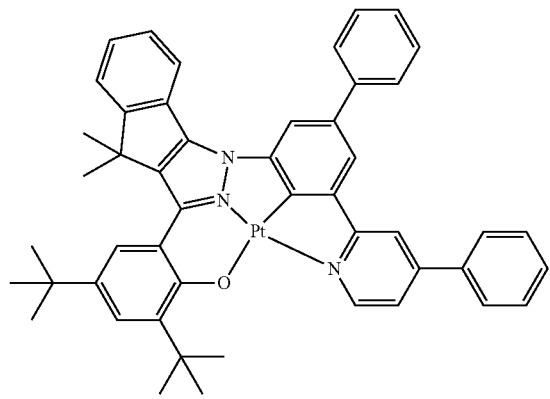
4
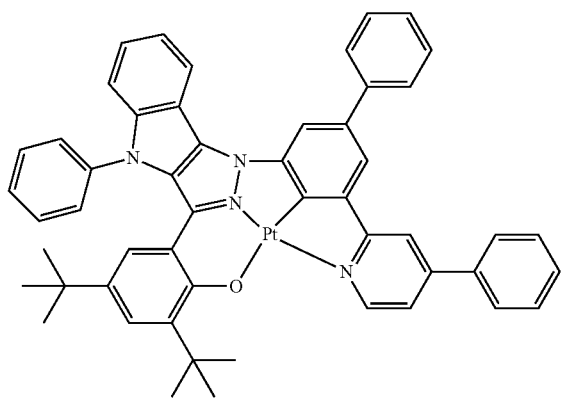
-continued
5
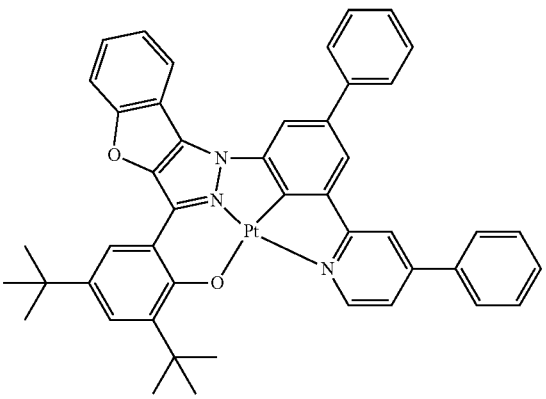
6
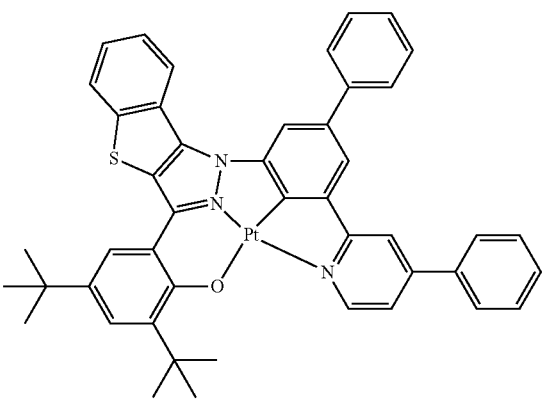
7
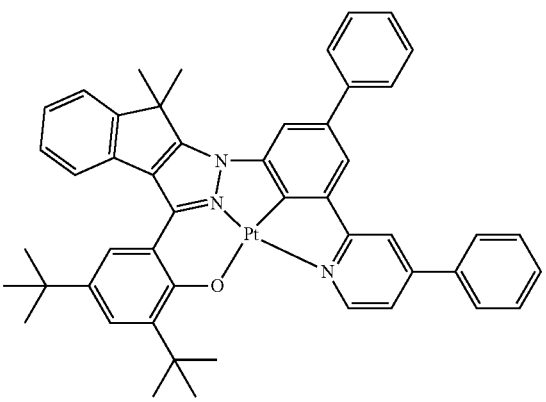

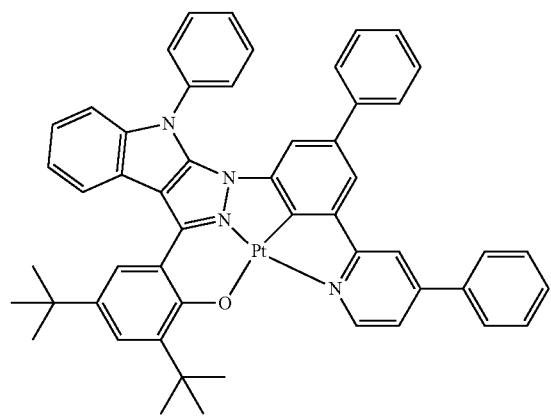
8
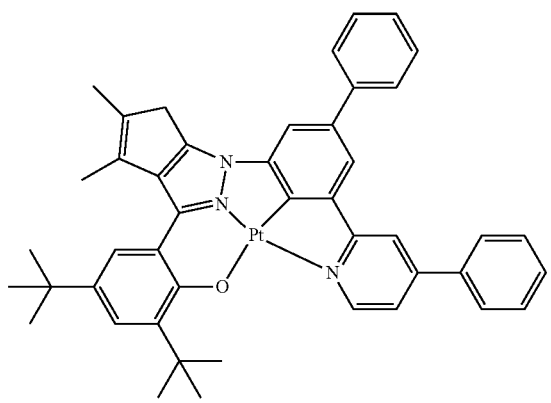
11
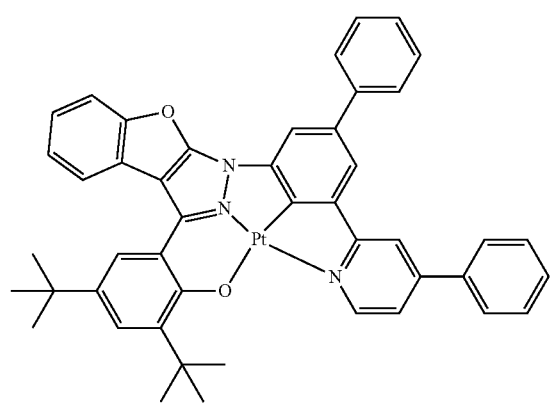
9
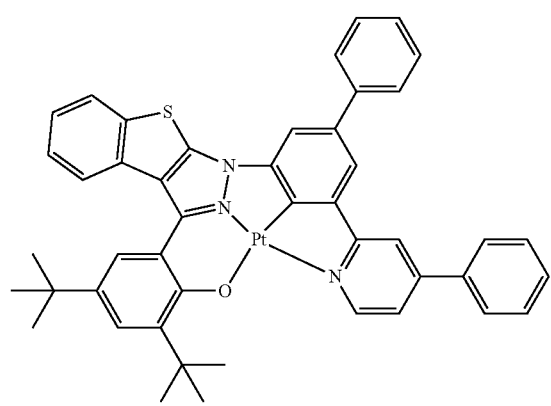
10
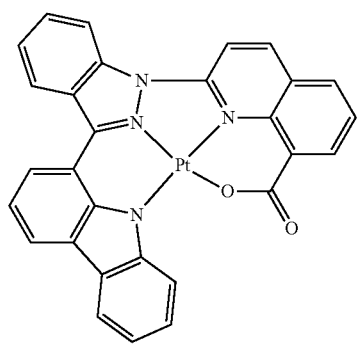
16

17
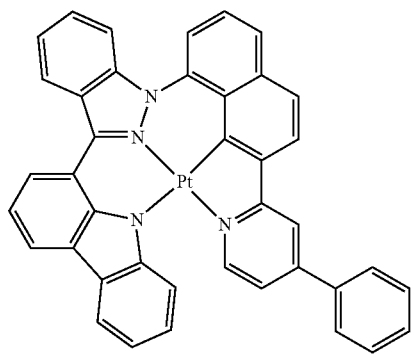
18
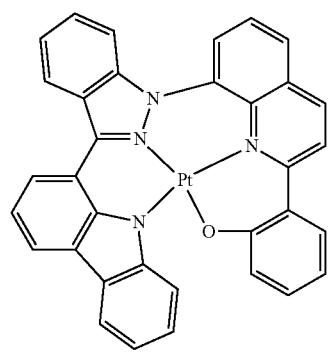
19
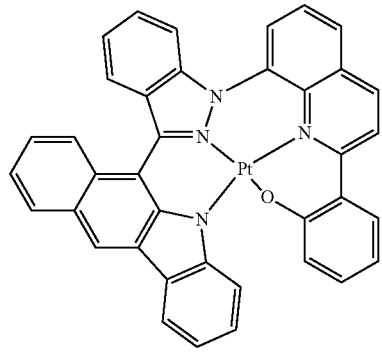
20
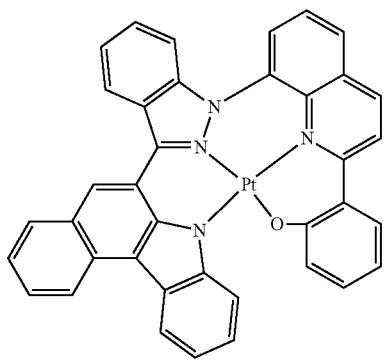
21
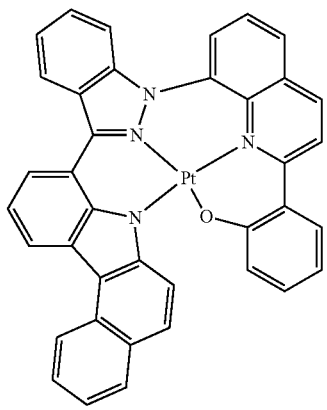
22
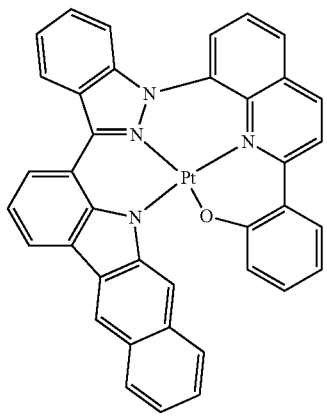
23
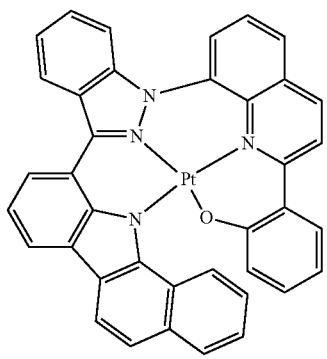
24
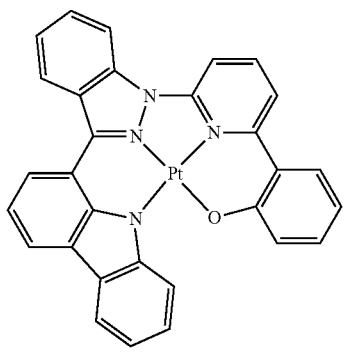

211
-continued
25
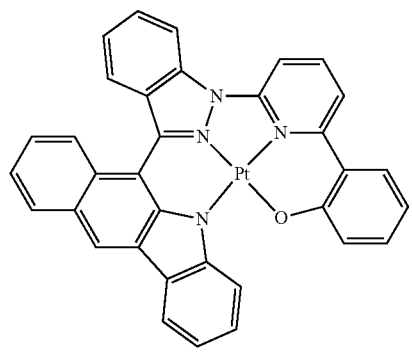
26
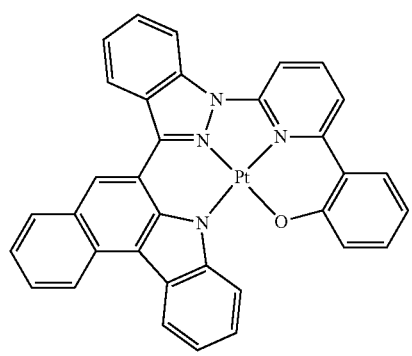
27
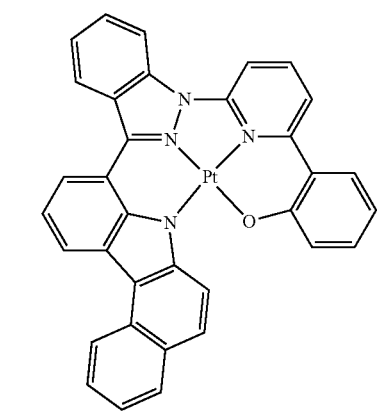
28
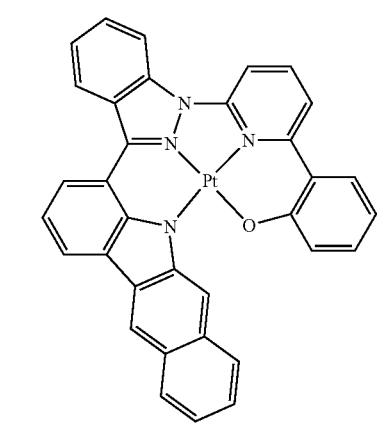
212
-continued
29
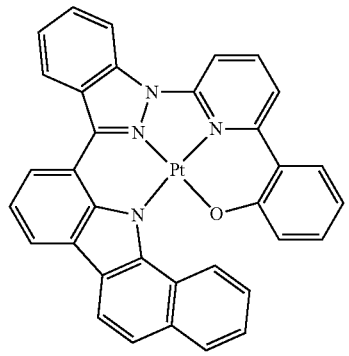
30
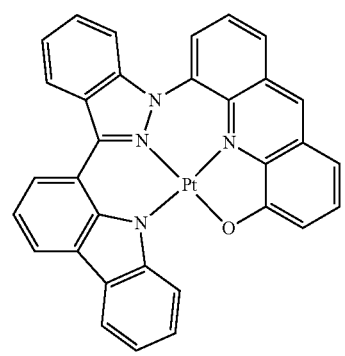
31
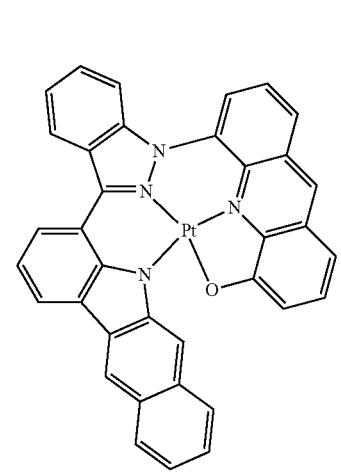
32
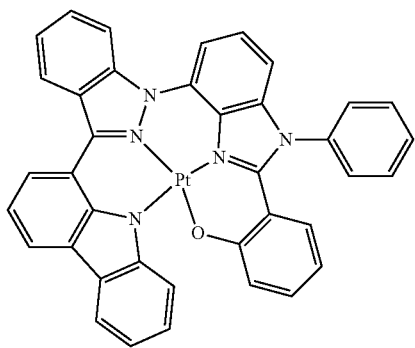

213
-continued
33
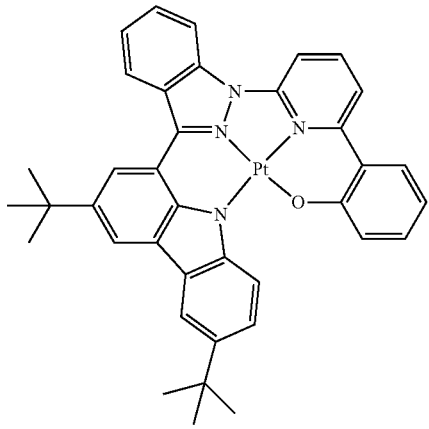
34
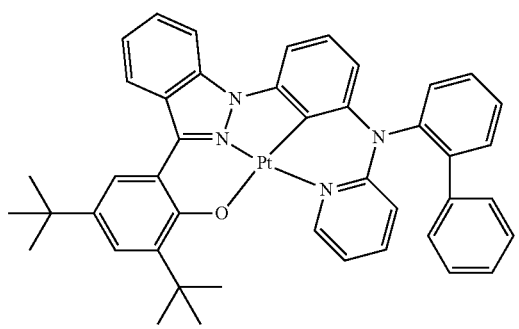
35
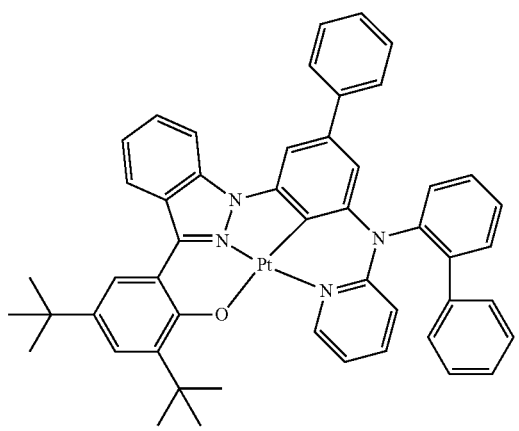
36
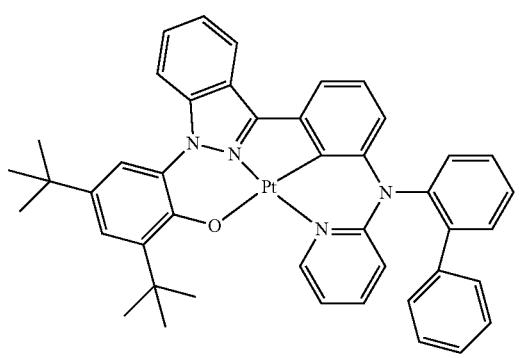
214
-continued
37
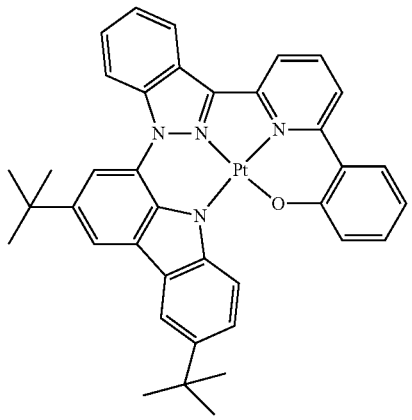
39
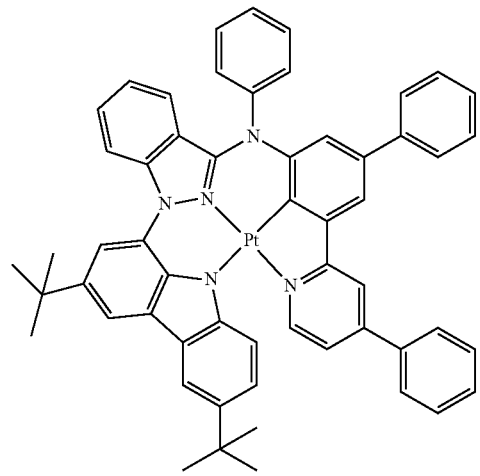
40
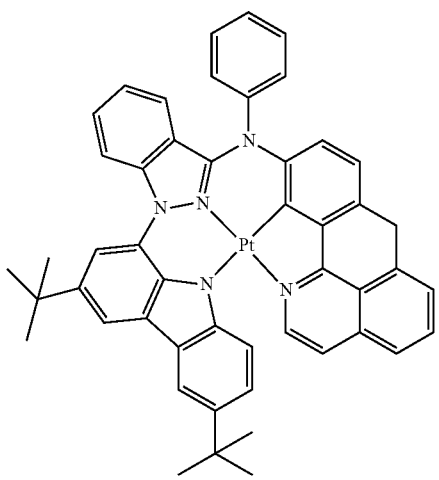

43
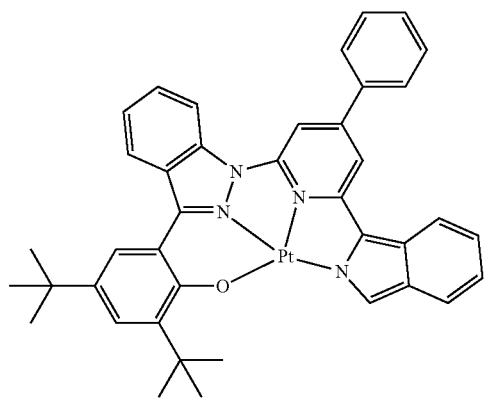
44
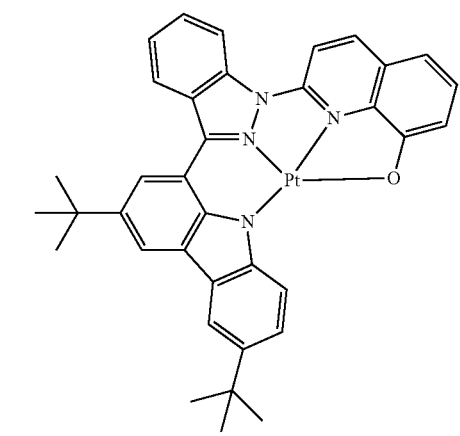
45
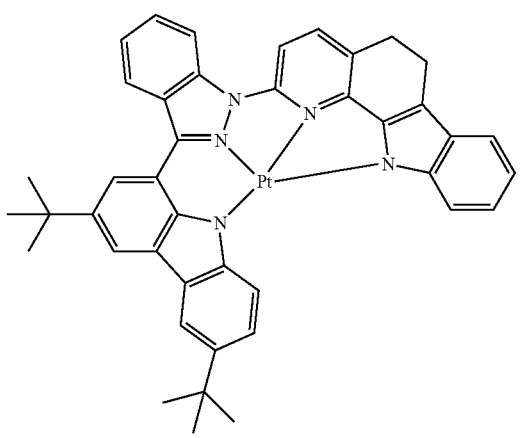
46
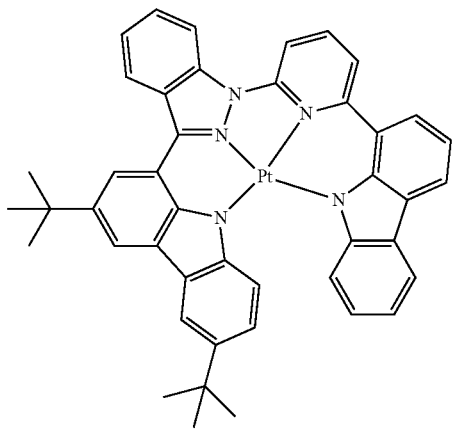
47
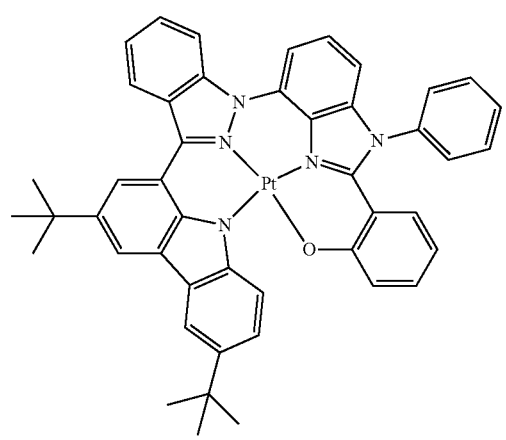
48
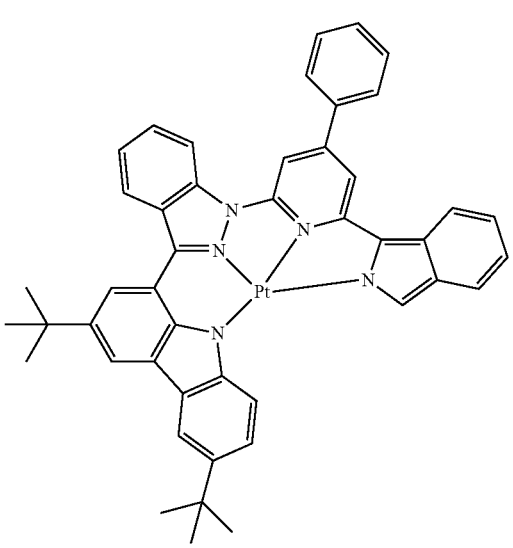

49
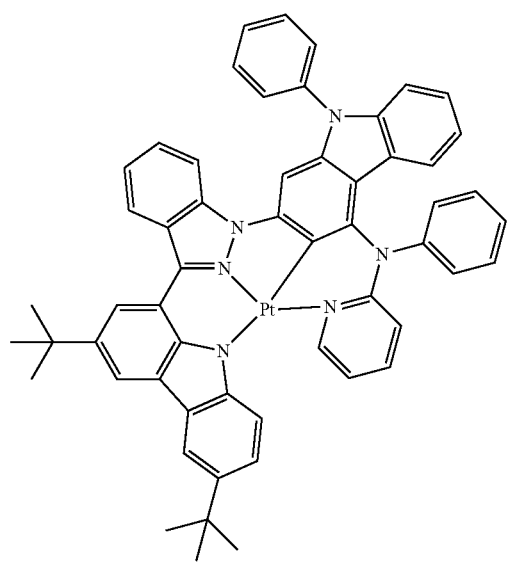
50
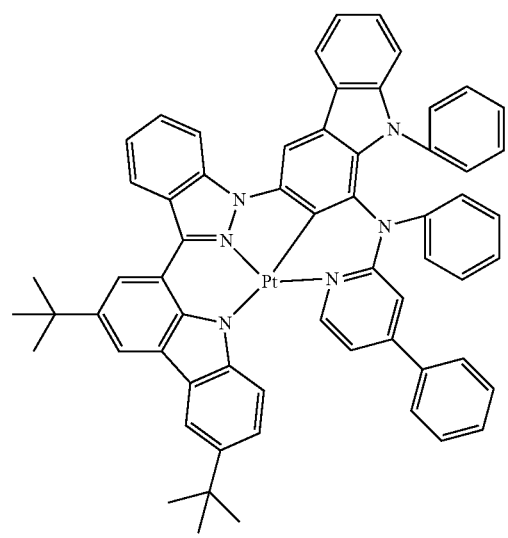
51
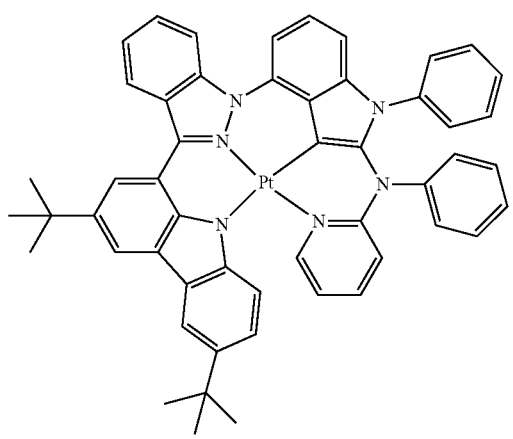
53
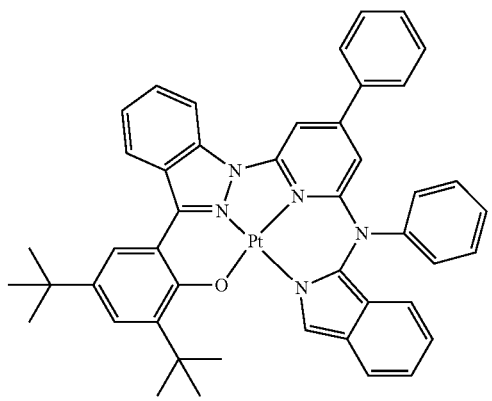
54
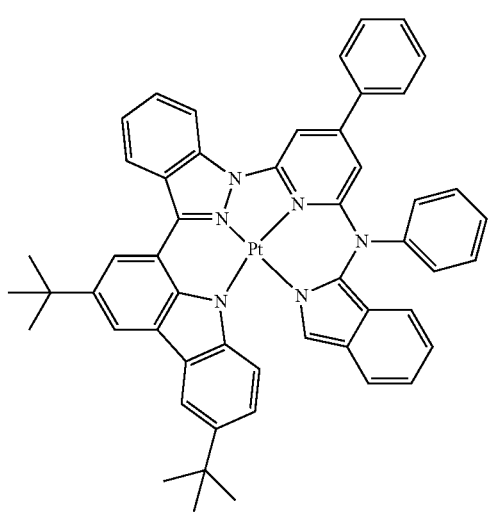
58
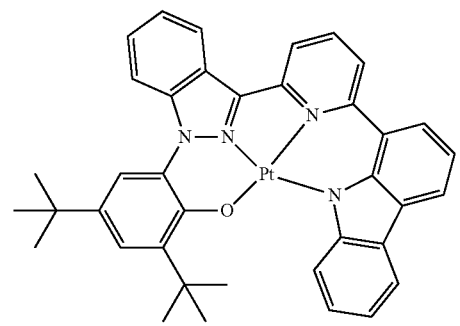
60
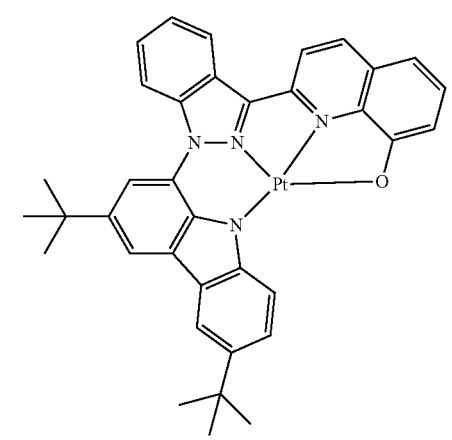

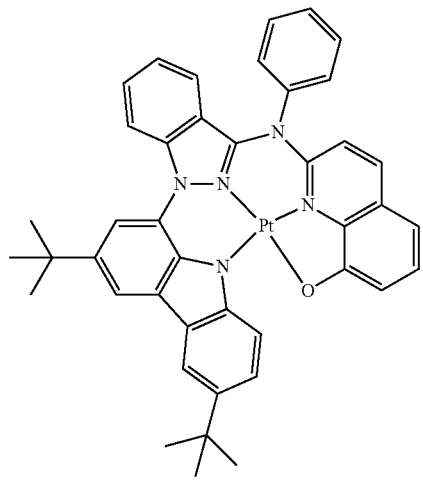
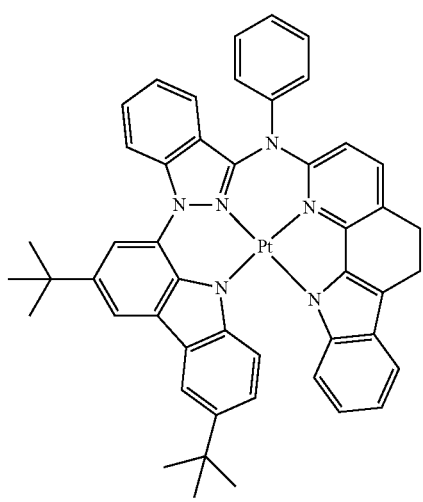
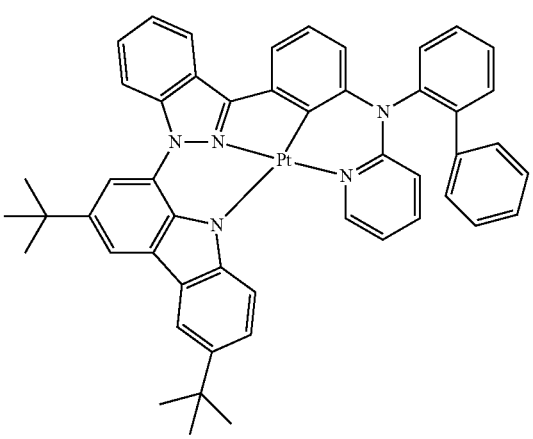
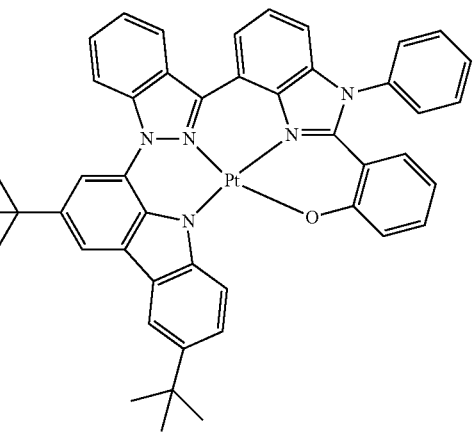

221
-continued
67
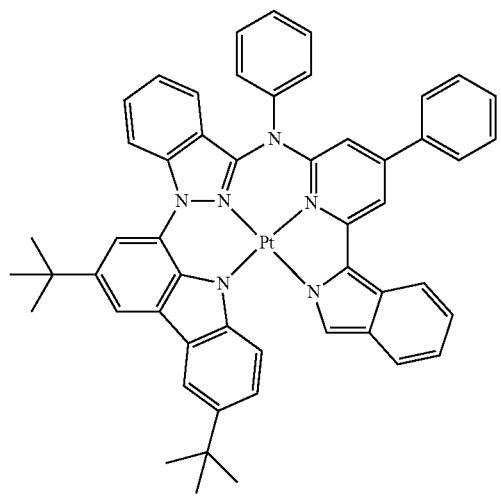
68
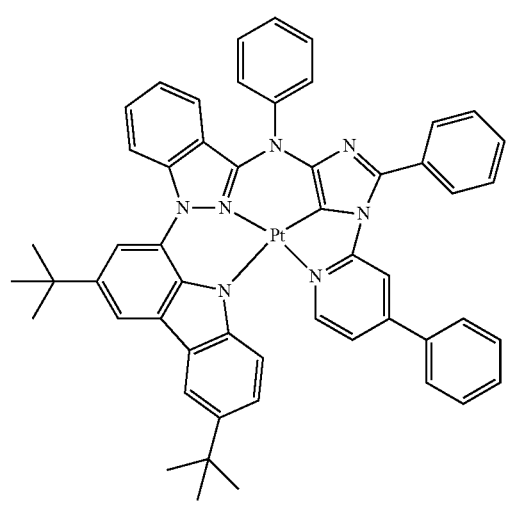
69
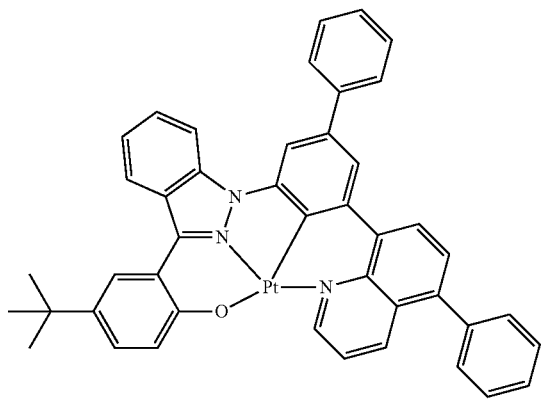
222
-continued
70
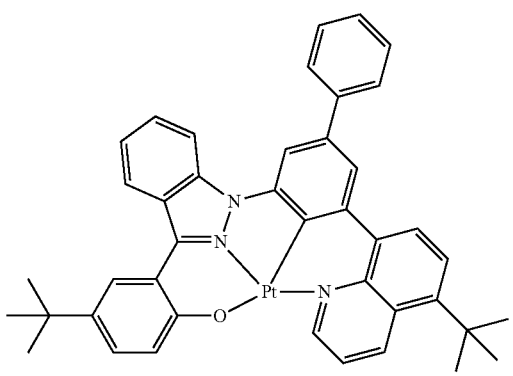
71
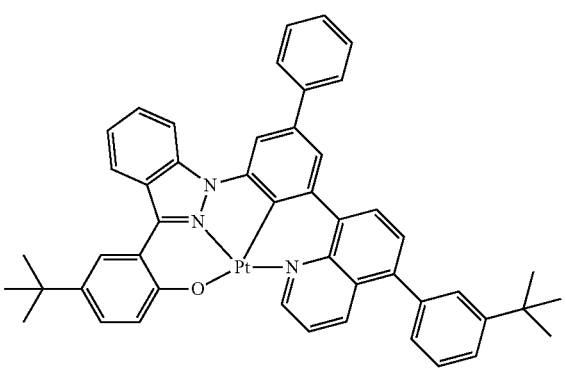
72
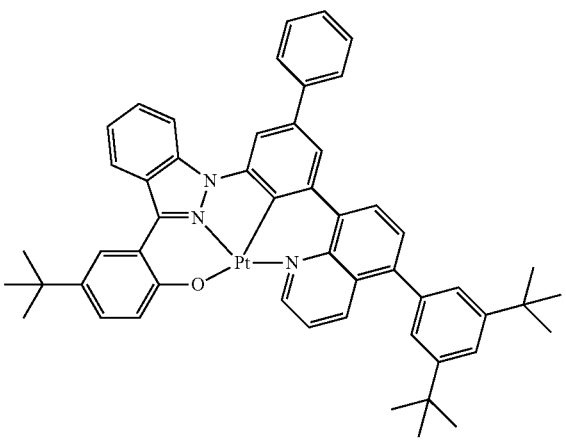
73
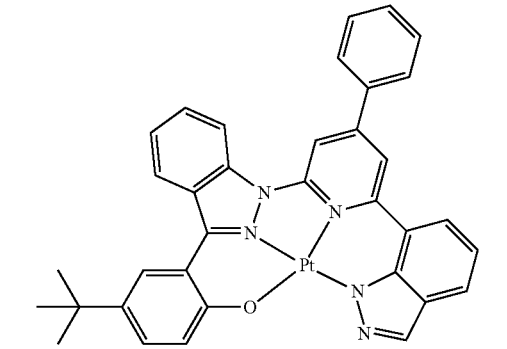

223
-continued
74
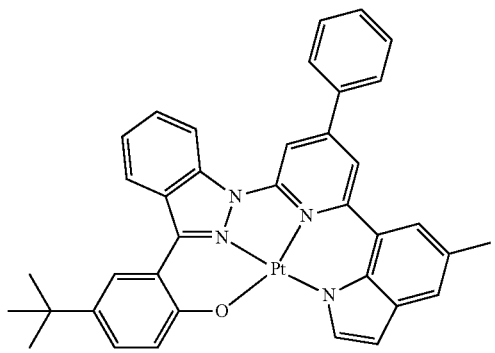
75
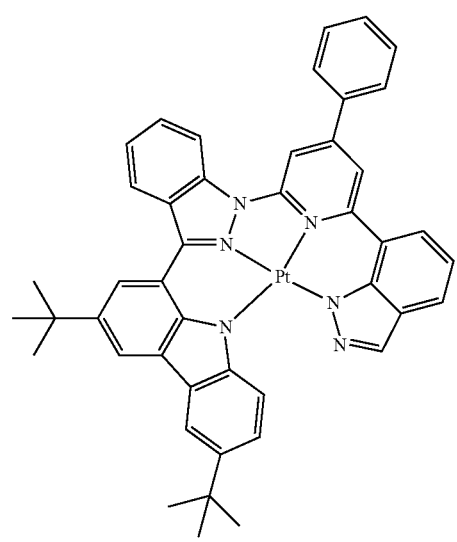
76
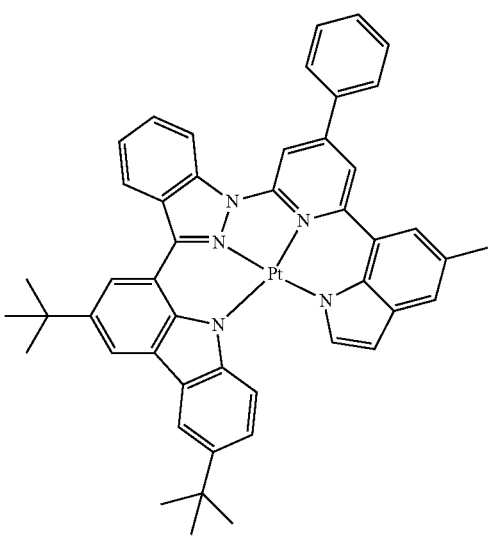
224
-continued
77
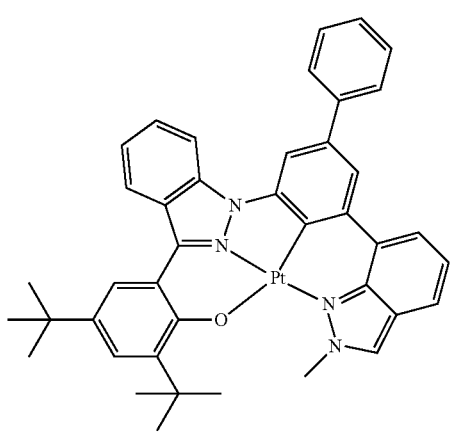
78
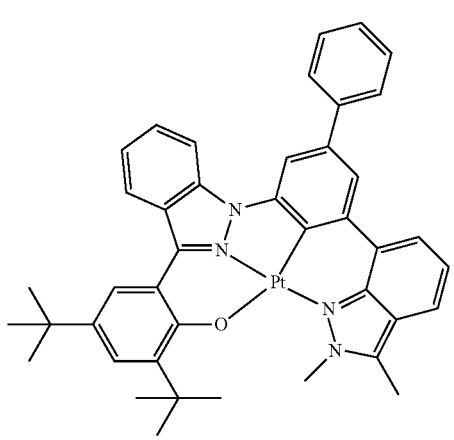
79
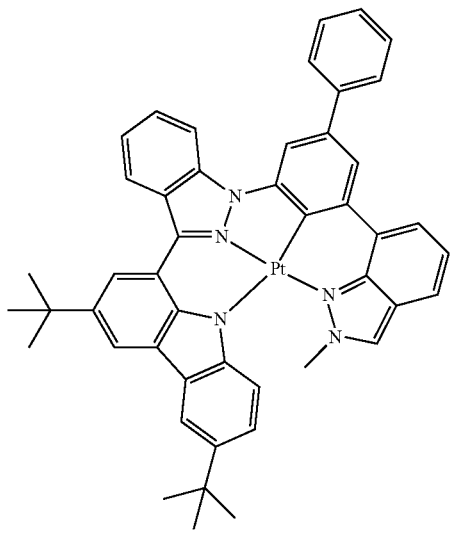

225
-continued
80
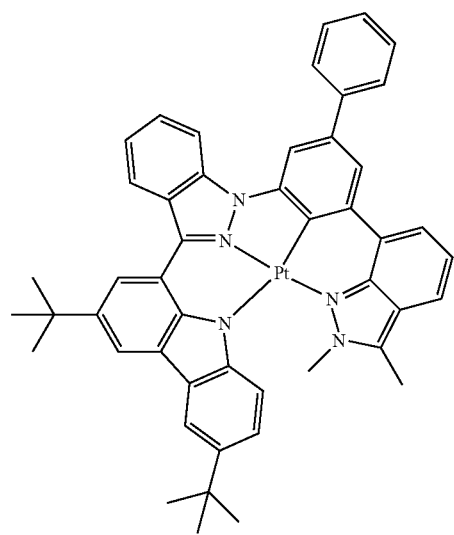
81
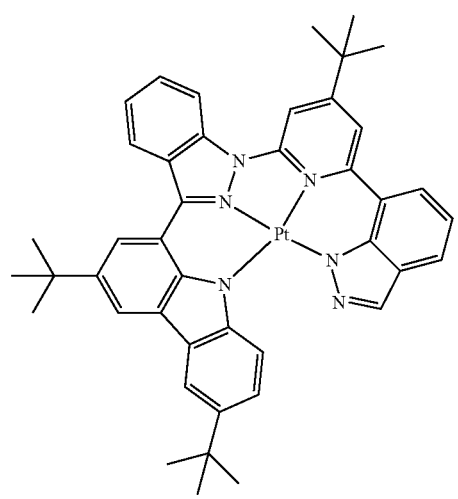
82
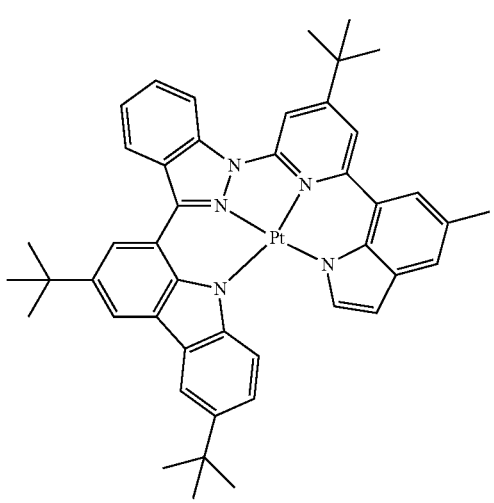
226
-continued
83
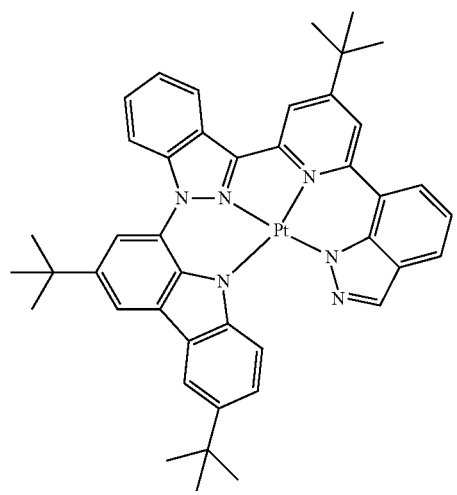
84
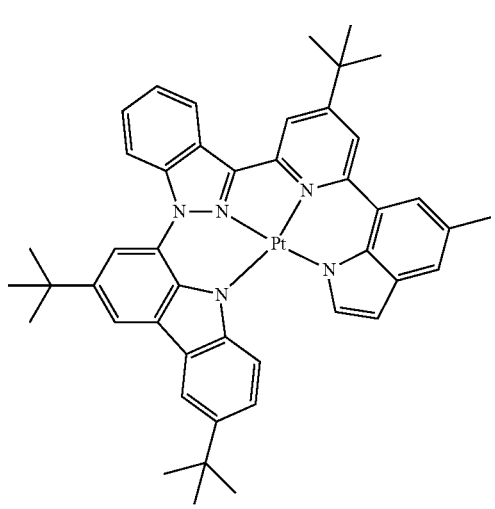
85
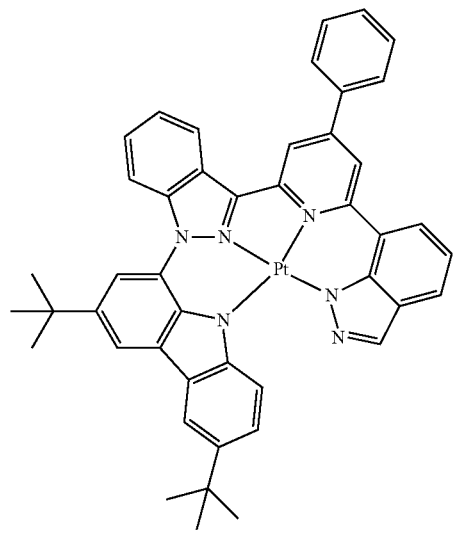

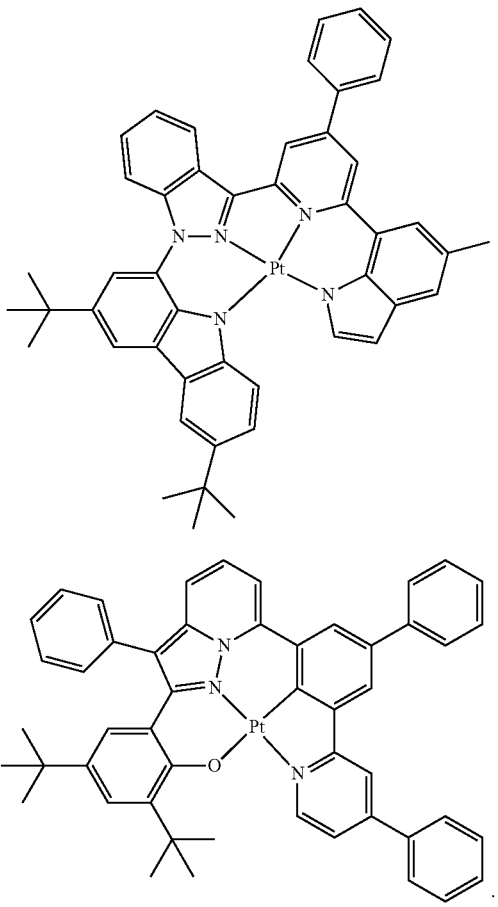

16. An organic light-emitting device comprising:
    a first electrode;
    a second electrode; and
    an organic layer disposed between the first electrode and the second electrode, wherein the organic layer comprises an emission layer, and
    wherein the organic layer further comprises at least one organometallic compound of claim 1.

17. The organic light-emitting device of claim 16, wherein
    the first electrode is an anode,
    the second electrode is a cathode,
    the organic layer further comprises a hole transport region disposed between the first electrode and the emission layer and an electron transport region disposed between the emission layer and the second electrode,
    wherein the hole transport region comprises a hole injection layer, a hole transport layer, an electron blocking layer, or any combination thereof, and
    wherein the electron transport region comprises a hole blocking layer, an electron transport layer, an electron injection layer, or any combination thereof.

18. The organic light-emitting device of claim 16, wherein the emission layer comprises the at least one organometallic compound.

19. The organic light-emitting device of claim 18, wherein the emission layer further comprises a host, and
    an amount of the host is larger than an amount of the organometallic compound.

20. A diagnostic composition comprising at least one organometallic compound of claim 1.

* * * * *